(12) United States Patent
Cleveland et al.

(10) Patent No.: US 11,458,019 B2
(45) Date of Patent: Oct. 4, 2022

(54) PROSTHETIC IMPLANTS INCLUDING A FRAME FOR FIXATION TO BONE AND RELATED METHODS

(71) Applicant: DePuy Ireland Unlimited Company, Ringaskiddy (IE)

(72) Inventors: Benjamin Cleveland, Bellingham, MA (US); Mollie Rosen, Boston, MA (US); James Brownhill, Norton, MA (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 273 days.

(21) Appl. No.: 16/451,720

(22) Filed: Jun. 25, 2019

(65) Prior Publication Data
US 2020/0405491 A1 Dec. 31, 2020

(51) Int. Cl.
*A61F 2/40* (2006.01)
*A61F 2/30* (2006.01)

(52) U.S. Cl.
CPC ........ *A61F 2/30749* (2013.01); *A61F 2/4081* (2013.01); *A61F 2002/305* (2013.01); *A61F 2002/30224* (2013.01); *A61F 2002/30331* (2013.01); *A61F 2002/30428* (2013.01); *A61F 2002/30507* (2013.01); *A61F 2002/4085* (2013.01)

(58) Field of Classification Search
CPC ...... A61F 2/30749; A61F 2/40; A61F 2/4081; A61F 2002/30428; A61F 2002/305; A61F 2/4261; A61F 2002/30507; A61F 2002/4085
See application file for complete search history.

(56) References Cited

U.S. PATENT DOCUMENTS

| | | | |
|---|---|---|---|
| 4,964,865 A | * | 10/1990 | Burkhead ............... A61F 2/40 623/19.11 |
| 7,922,769 B2 | | 4/2011 | Deffenbaugh et al. |
| 7,959,680 B2 | | 6/2011 | Stone et al. |
| 8,920,508 B2 | | 12/2014 | Iannotti et al. |
| 9,439,768 B2 | | 9/2016 | Iannotti et al. |
| 9,597,190 B2 | | 3/2017 | Chavarria et al. |
| 9,770,334 B2 | | 9/2017 | Wiley et al. |

(Continued)

FOREIGN PATENT DOCUMENTS

WO 2019/053576 A1 3/2019

OTHER PUBLICATIONS

Extended European Search Report for Application No. 20182087.5, dated Sep. 17, 2020 (8 pages).

*Primary Examiner* — Christopher D. Prone

(57) ABSTRACT

The present disclosure provides for prosthetic implants to be used in various surgical repairs, including for procedures like total shoulder arthroplasties and reverse total shoulder arthroplasties. The implants include two main parts—a frame and a prosthetic component. The frame includes an aperture that is configured to receive the prosthetic component, allowing the prosthetic component to make direct contact with bone at the surgical site. Various configurations are provided that allow the prosthetic component to be coupled to or otherwise engage with the frame, and at least some of the configurations are such that the reverse procedures can be done without having to fully re-tool and/or modify the bone. A variety of procedures resulting from the improved implants are also provided.

9 Claims, 30 Drawing Sheets

(56) References Cited

U.S. PATENT DOCUMENTS

| | | |
|---|---|---|
| 2005/0261775 A1* | 11/2005 | Baum .................. A61F 2/4081 |
| | | 623/19.12 |
| 2006/0020344 A1* | 1/2006 | Shultz ....................... A61F 2/40 |
| | | 623/19.12 |
| 2007/0156246 A1 | 7/2007 | Meswania et al. |
| 2011/0153023 A1 | 6/2011 | Deffenbaugh et al. |
| 2013/0066321 A1 | 3/2013 | Mannss et al. |
| 2013/0261753 A1* | 10/2013 | Lappin ................ A61F 2/30734 |
| | | 623/19.11 |
| 2017/0071749 A1 | 3/2017 | Lappin et al. |
| 2017/0304063 A1 | 10/2017 | Hatzidakis et al. |
| 2018/0092747 A1 | 4/2018 | Hopkins |
| 2018/0368982 A1 | 12/2018 | Ball |
| 2020/0030108 A1 | 1/2020 | Orphanos et al. |

\* cited by examiner

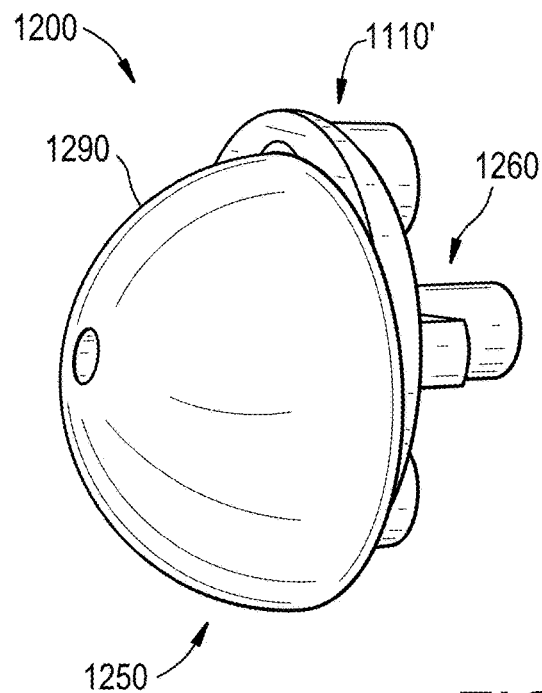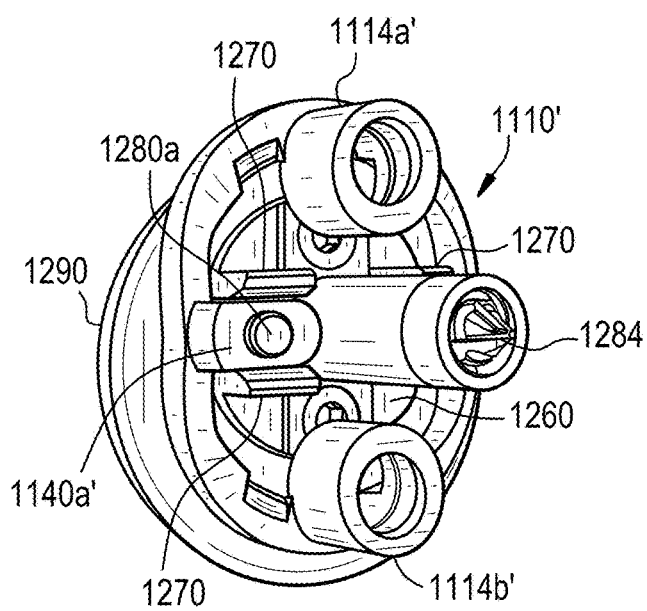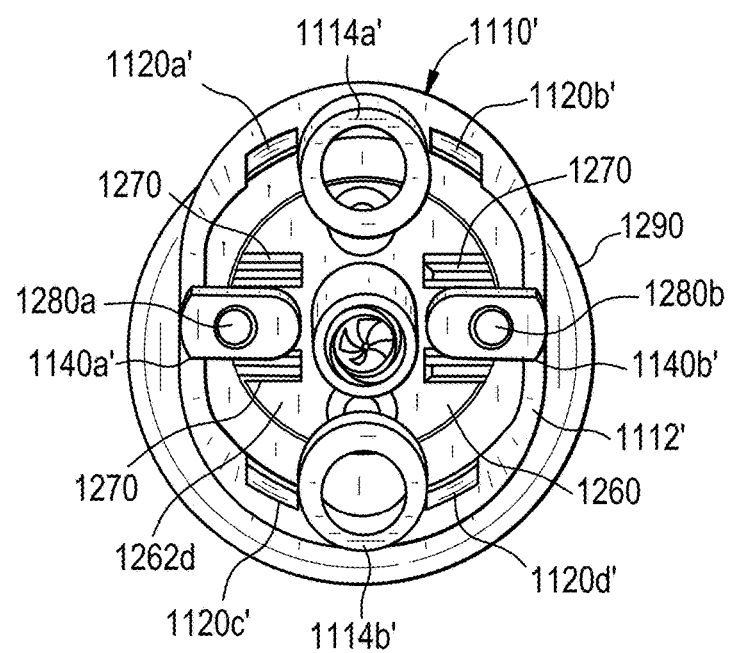

PROSTHETIC IMPLANTS INCLUDING A FRAME FOR FIXATION TO BONE AND RELATED METHODS

FIELD

The present disclosure relates generally to prosthetic implants, and more particularly to prosthetic implants including a frame for fixation to bone and related methods for deploying such implants in a patient.

BACKGROUND

During the lifetime of a patient, it may be necessary to perform a total shoulder arthroplasty on the patient because of disease or trauma, for example. As shown in FIG. 1A, in an anatomic total shoulder arthroplasty, a humeral prosthesis 10 can be used to replace the natural head of the patient's humerus. The humeral prosthesis 10 typically includes an elongated post component 12 that is implanted into the intramedullary canal of the patient's humerus and a hemispherical-shaped prosthetic head component 14 that is secured to the post component 12. Additionally, the natural glenoid surface of the scapula can be resurfaced or otherwise replaced with an anatomic glenoid implant 20. An anatomic glenoid implant 20 typically includes a concave bearing surface 24 upon which the prosthetic head component 14 of the humeral prosthesis 10 articulates. A peg or keel 22 can project from the distal end of the implant 20 and can be cemented into the glenoid cavity of the patient's scapula.

Anatomic glenoid implants are typically made of polyethylene. Polyethylene is a plastic material having relatively low strength, hardness, and rigidity, but relatively high ductility and impact strength. To improve durability and fixation to bone, some polyethylene implants are augmented with a metal back plate. For example, FIG. 1B shows an anatomic glenoid implant 20' having a metal back plate 30 disposed on a distal surface of a polyethylene component 32. Such metal back implants can have some drawbacks, such as increased wear rates, glenoid loosening, stress shielding, excessive glenoid bone loss or other osteolysis, and/or dissociation of the polyethylene component from the metal back plate. Attempts to address some of these drawbacks have included adjusting the thickness of the polyethylene component. However, making the polyethylene component too thin can cause accelerated wear of the implant. Conversely, making the polyethylene component too thick can cause over-tension of the rotator cuff and increased load on the polyethylene component.

In some clinical situations, it may be preferable to perform a reverse total shoulder arthroplasty to change the mechanics of the shoulder, e.g., when the patient's natural shoulder has degenerated to a severe degree of joint instability and pain. Reverse shoulder joint implants can be used to reverse the anatomy, or structure, of the healthy shoulder. For example, as shown in FIG. 1C, in a reverse total shoulder arthroplasty, a humeral prosthesis 50 can be used to replace the natural head of the patient's humerus. The humeral prosthesis 50 typically includes an elongated post component 52 that is implanted into the intramedullary canal of the patient's humerus and a concave-shaped prosthetic head component 54, known as a humeral cup, that is secured to the post component 52. Additionally, a reverse glenoid implant, e.g., a hemispherical-shaped glenosphere 60, can be secured to the glenoid bone of the patient's scapula. Such a reverse configuration allows the patient's deltoid muscle, which is one of the larger and stronger shoulder muscles, to raise the arm.

In some patients, an anatomic-to-reverse total shoulder arthroplasty can be performed to convert a previously reconstructed shoulder joint from an anatomic configuration to a reverse configuration. On the glenoid-side, the previously deployed anatomic glenoid implant (e.g., 20 or 20') can be replaced with a reverse glenoid implant (e.g., glenosphere 60). Such replacement typically involves a procedure that is complex and challenging due to the independent configurations and components of the respective implants. In some clinical situations, bone loss and/or further deterioration of glenoid bone can also occur during the procedure that can compromise the integrity of the anatomic-to-reverse conversion.

Accordingly, there is a need for improved prosthetic implants and related methods for fixing implants to bone in a manner that avoids the drawbacks of conventional metal back implants (such as the devices and methods described above with respect to anatomic shoulder joint reconstruction procedures). Additionally, there is a further need for improved prosthetic implants and related methods for performing anatomic-to-reverse total shoulder conversions in an efficient manner that can overcome these complexities.

SUMMARY

The present disclosure provides for a combination of a frame and prosthetic component that can be used in conjunction for superior implants, particularly for use in glenoid repair procedures, although a person skilled in the art will appreciate implants provided for herein, or otherwise derivable in view of the present disclosures, can be used in other applications and in other portions of a patient's body, such patients not being limited to humans (i.e., any animal). As described herein, a combination of a frame and prosthetic component are used to allow the prosthetic component to have direct contact with an implant site. The frame defines an aperture through which a distal-facing surface of the prosthetic components can pass to directly engage with bone at an implant site. The frames and prosthetic components provided for herein provide a variety of different configurations that allow the prosthetic component to be secured or otherwise coupled to the frame while also engaging the bone. The frame provides stability, and the prosthetic component provides desired direct contact with the bone. In many embodiments, the frame can be made of one or more metals and the prosthetic can be made of one or more plastic materials. Some non-limiting examples of configurations provided for having the prosthetic component engage with the frame include bone anchor pockets, anchoring pegs, snap-fit connector interfaces and components, and removable frame adaptors (e.g., T-bars). The present disclosures also allow for the benefit of being able to use some of the same components, such as the frame, for both a regular repair (e.g., a total shoulder arthroplasty) and a reverse repair (e.g., a reverse total shoulder arthroplasty).

In one exemplary embodiment, a prosthetic implant includes a prosthetic component and a frame. The prosthetic component has a proximal-bearing surface and a distal-facing surface, with the distal-facing surface being opposed to the proximal-bearing surface. The frame is configured to be anchored in bone. The frame defines an aperture through which a portion of the prosthetic component is configured to be disposed, and the fame includes one or more attachment interfaces. The one or more attachment interfaces are configured to couple the prosthetic component to the frame such that the distal-facing surface of the prosthetic component extends through the aperture of the frame to be in direct contact with bone.

The frame can include one or more metals. The frame can also include an annular-shaped body. The annular-shaped body can include a substantially planer proximal surface and a substantially convex-shaped distal surface. An inner wall of the annular-shaped body can define the aperture of the frame.

In some embodiments, the frame includes one or more bone anchor pockets for anchoring the frame to bone. Each of the one or more bone anchor pockets can define a through bore through which to insert a bone anchor into bone. The bone anchor pocket(s) can be accessible through the aperture of the frame. The frame can include a plurality of anchoring pegs for anchoring the frame to bone. The anchoring begs can extend distally from the frame.

The one or more attachment interfaces of the frame can include one or more snap-fit connector interfaces. In some such embodiments, the prosthetic component can include a body that itself includes one or more snap-fit connectors that can be configured to snap onto the one or more snap-fit connector interfaces of the frame. The distal-facing surface of the prosthetic component can be in direct contact with bone through the aperture of the frame when the snap-fit connector(s) of the prosthetic component are attached to the snap-fit connector interface(s) of the frame.

In addition to, or in lieu of, the frame including one or more metals, the prosthetic component can include one or more plastic materials. The prosthetic component can include a post that extends from the distal-facing surface of the prosthetic component. The post can be configured to engage a void formed in bone. In some embodiments the distal-facing surface of the prosthetic component can include a cross-sectional profile that is shaped to form a negative of a cross-sectional profile of the aperture of the frame.

The proximal-bearing and distal-facing surfaces can have a variety of shapes, including each being of a convex shape, each being of a concave shape, and one being of a convex shape while the other is of a concave shape. For example, in some exemplary embodiments, the distal-facing surface of the prosthetic component can include a convex shape, and the proximal-bearing surface of the prosthetic component can include a concave shape.

The one or more attachment interfaces of the frames can have a variety of configurations. For example, in some instances the one or more attachment interfaces of the frame can include a removable frame adaptor. The removable frame adaptor can define one or more locking screw holds, and the removable frame adaptor can be configured to extend across the aperture, between opposing legs of the frame. In some such embodiments, the frame can include a distal surface that defines opposing recesses that can be configured to guide the removable frame adaptor into alignment across the aperture of the frame between the opposing legs of the frame. The prosthetic component can define one or more through holes that can correspond to the one or more locking holes of the removable frame adaptor. Further, the prosthetic component can be configured to be coupled to the frame by inserting a locking screw through the one or more through holes of the prosthetic component and into the one or more locking screw holes of the removable frame adaptor. The distal-facing surface of the prosthetic component can define a recess for aligning the prosthetic component with the removable frame adaptor. In some embodiments, the implant can include a prosthetic head. The head can have a hemispherical shape and can be coupled to the proximal-bearing surface of the prosthetic component. The prosthetic component can include a post that extends from the distal-facing surface of the prosthetic component. The post can be configured to engage a void formed in bone.

By way of further example, the one or more attachment interfaces of the frame can include one or more locking screw pockets that can be accessible through the aperture. The locking screw pocket(s) can define one or more corresponding locking screw holes. In some embodiments, the locking screw pocket(s) can include at least two screw pockets that project into the aperture from opposing legs of the frame. The prosthetic component can define one or more through holes that can correspond to the one or more locking holes of the one or more locking screw pockets. Further, the prosthetic component can be configured to be coupled to the frame by inserting a locking screw through the one or more through holes of the prosthetic component and into the locking screw hole(s) of the locking screw pocket(s). The distal-facing surface of the prosthetic component can include one or more guide rails, which can be for aligning the prosthetic component with the locking screw pocket(s). In some embodiments, the implant can include a prosthetic head. The head can have a hemispherical shape and can be coupled to the proximal-bearing surface of the prosthetic component. In some such embodiments, the prosthetic head can define an opening through which to insert a locking screw through the one or more through holes of the prosthetic component and into the locking screw hole(s) of the locking screw pocket(s). The prosthetic component can include a post that extends from the distal-facing surface of the prosthetic component. The post can be configured to engage a void formed in bone.

By way of still further example, the one or more attachment interfaces of the frame can include a plurality of anchoring pegs. The anchoring pegs can protrude from the frame and can be for anchoring the frame to bone. One or more of such pegs can define one or more bores in them. The prosthetic component can define one or more holes that can correspond to the one or more bores defined in the anchoring peg(s). Further, the prosthetic component can be configured to be coupled to the frame by inserting a locking screw through the hole(s) of the prosthetic component and into the one or more bores defined in the anchoring peg(s). In some such embodiments, the distal-facing surface of the prosthetic component can have a cross-sectional profile shaped to form a negative of a cross-sectional profile of the aperture of the frame. An unthreaded bore can be defined in at least one of the anchoring pegs of the frame. In some such embodiments, the prosthetic component can include an anti-rotation peg that projects from the distal-bearing surface of the prosthetic component. The anti-rotation peg can be configured to mate with the unthreaded bore. In some embodiments, the implant can include a prosthetic head. The head can have a hemispherical shape and can be coupled to the proximal-bearing surface of the prosthetic component. The prosthetic component can include a post that extends from the distal-facing surface of the prosthetic component. The post can be configured to engage a void formed in bone.

In some embodiments, the implant can include a bone screw. The bone screw can be configured to be disposed within the post of the prosthetic component to anchor the prosthetic component to bone.

The one or more attachment interfaces can include at least two attachment interfaces. In some such embodiments, a first attachment interface can be configured to attach a prosthetic glenoid component to the frame, and the second attachment interface can be configured to attach a prosthetic glenosphere component to frame.

In one exemplary method of inserting a prosthetic implant into a patient, the method includes anchoring a frame to bone and coupling a prosthetic component to the frame. The frame defines an aperture, and the prosthetic component is coupled to the frame such that the prosthetic component is in direct contact with bone through the aperture of the frame.

The method can further include removing the prosthetic component from the frame and coupling a different prosthetic component to the frame while the frame remains anchored to bone. The different prosthetic component can be a component of a similar configuration as the initial prosthetic component, or it can have a different configuration.

The action of coupling a prosthetic component to the frame can be performed in a variety of manners. For example, in some instances, it can involve pressing the prosthetic component into the aperture of the frame such that the prosthetic component snaps onto one or more snap-fit connector interfaces of the frame. Alternatively, or additionally, it can involve inserting a removable frame adaptor into the aperture of the frame, and manipulating the frame adaptor to extend across the aperture between opposing legs of the frame. The frame adaptor can define one or more screw holes, and the method can further entail aligning one or more through holes of the prosthetic component with the one or more screw holes of the frame adaptor. A locking screw can be inserted through the one or more through holes of the prosthetic component and into the one or more screw holes of the frame adaptor.

By way of further non-limiting example, coupling a prosthetic component to the frame can include aligning one or more through holes of the prosthetic component with one or more screw holes defined in one or more locking screw pockets that project into the aperture from the frame. The method can further include inserting a locking screw through the bore(s) of the prosthetic component and into the one or more screw holes of the locking screw pocket(s) of the frame. By way of still further non-limiting example, coupling a prosthetic component to the frame can include aligning one or more through holes of the prosthetic component with one or more bores defined in one or more of a plurality of anchoring pegs that distally project from the frame. The method can further include inserting a locking screw through the through hole(s) of the prosthetic component and into the one or more bores of the one or more bores defined in the anchoring peg(s).

In some embodiments, the prosthetic component can be one of an anatomic glenoid component and a reverse glenoid component. The frame can include one or more metals. The prosthetic component can include one or more plastic materials.

BRIEF DESCRIPTION OF THE DRAWINGS

The accompanying drawings, which are incorporated herein and constitute part of this specification, illustrate exemplary embodiments, and together with the general description given above and the detailed description given below, explain the features of the various embodiments:

FIG. 14A is a front perspective view of one exemplary embodiment of a reverse shoulder joint implant, the implant including a frame similar to the frame of FIG. 11A;

FIG. 14B is a rear perspective view of the reverse shoulder joint implant of FIG. 14A;

FIG. 14C is a rear view of the reverse shoulder joint implant of FIG. 14A;

DETAILED DESCRIPTION

Figure 1A:
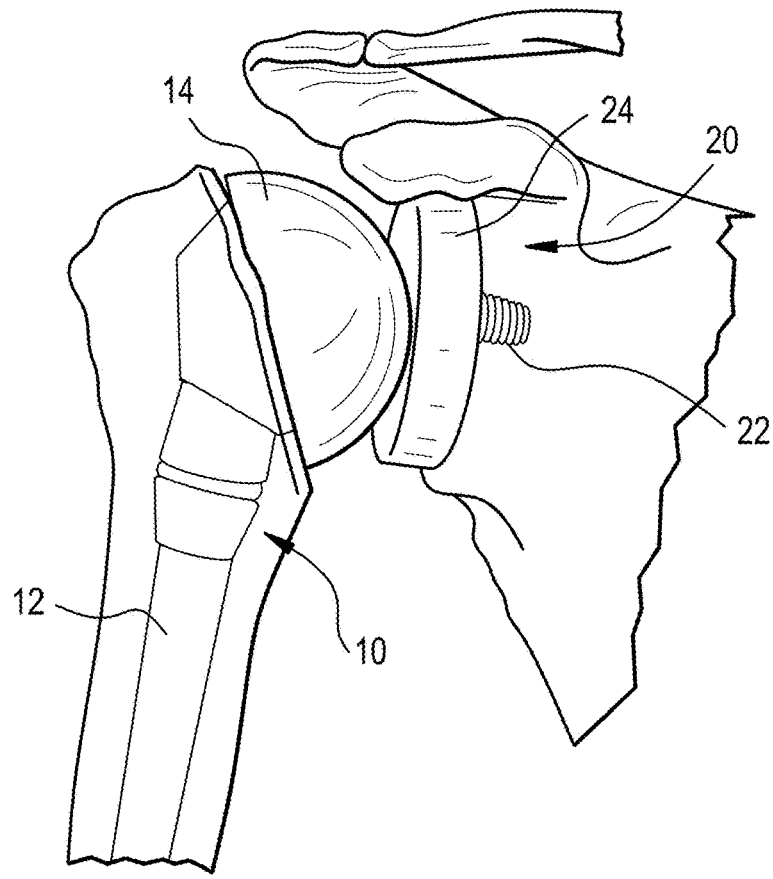
FIG. 1A is a side, partially transparent view of one example of an anatomic shoulder joint reconstruction, including an anatomic glenoid implant of the prior art coupled to a scapula.
Figure 1B:
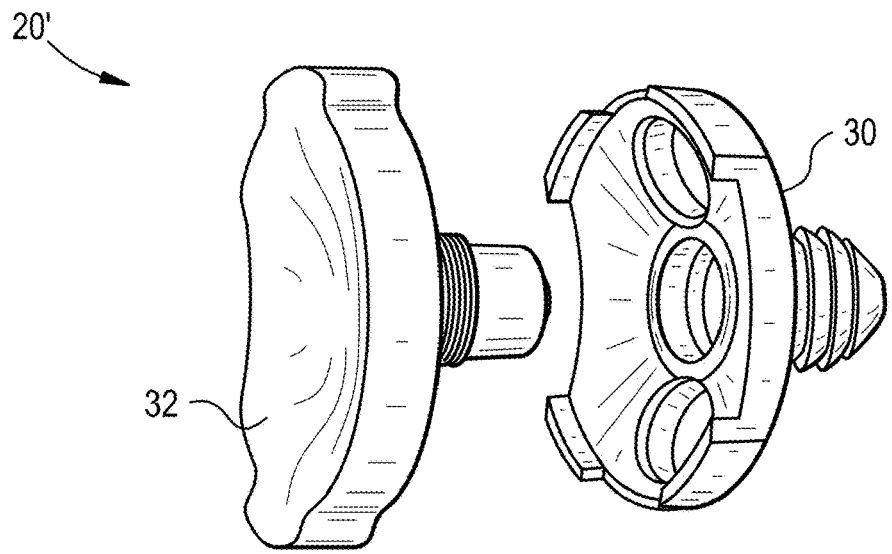
FIG. 1B is a side, perspective view of one example of an anatomic glenoid implant of the prior art having a metal back plate.
Figure 1C:
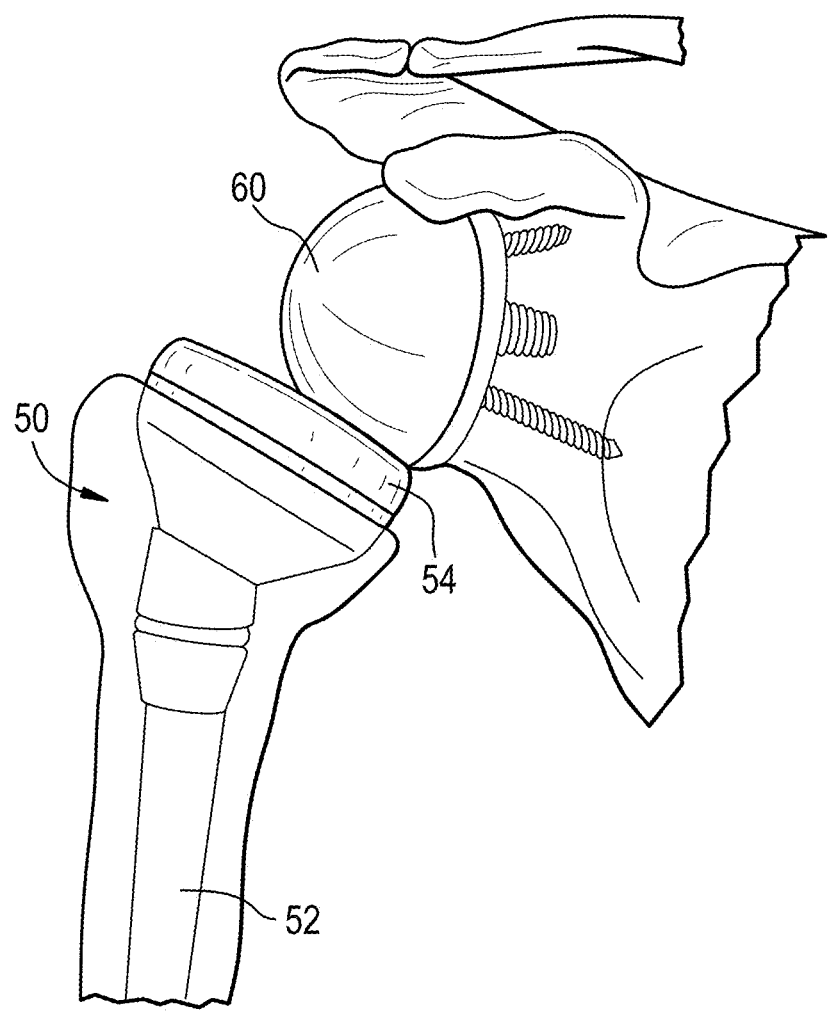
FIG. 1C is a side, partial transparent view of one example of reverse shoulder joint reconstruction, including a reverse glenoid implant of the prior art coupled to a scapula.
Figure 2A:
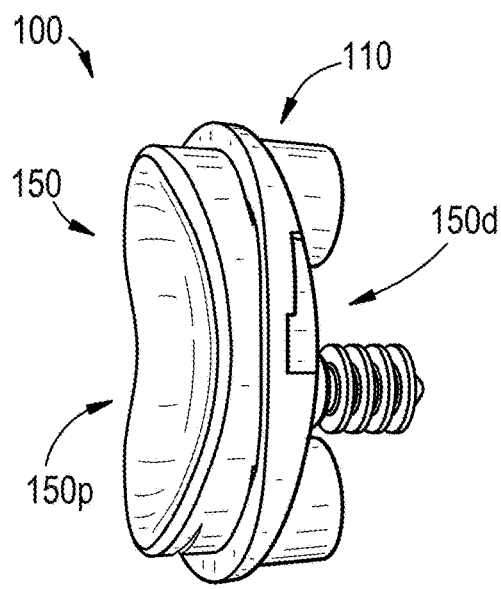
FIG. 2A is front perspective view of one exemplary embodiment of an anatomic shoulder joint implant.
Figure 2B:
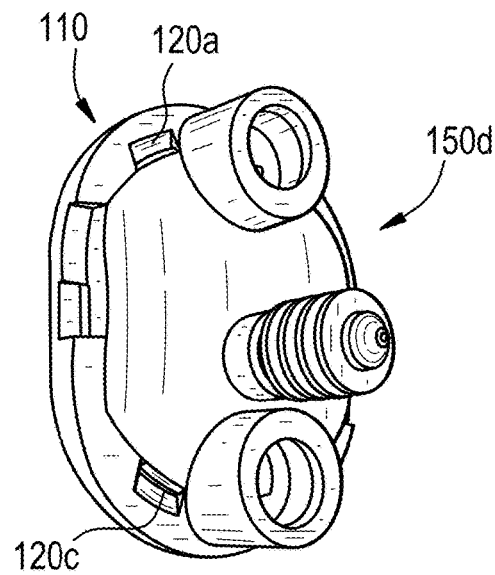
FIG. 2B is rear perspective view of the anatomic shoulder joint implant of FIG. 2A.
Figure 2C:
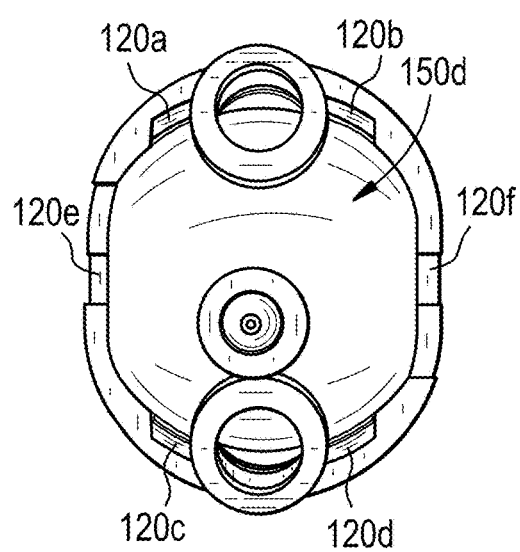
FIG. 2C is rear view of the anatomic shoulder joint implant of FIG. 2A.
Figure 2D:
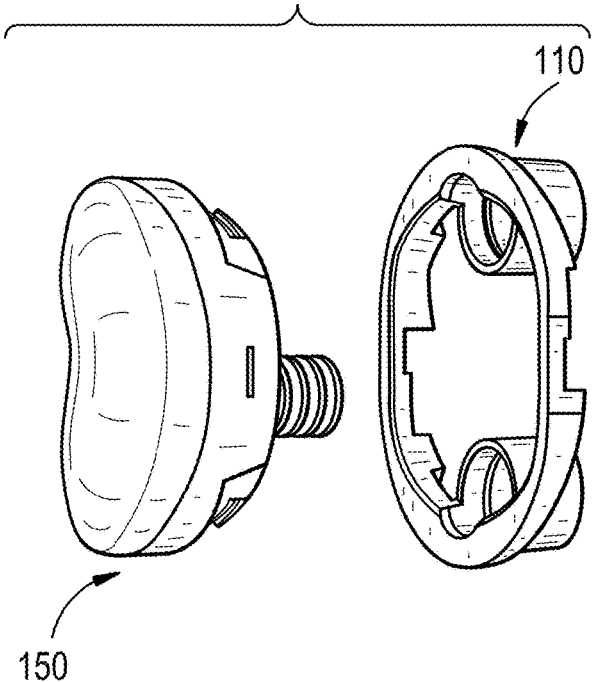
FIG. 2D is a perspective exploded view of components of the anatomic shoulder joint implant of FIG. 2A, the components including an anatomic glenoid component and a frame.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Sizes and shapes of the devices, and the components thereof, can depend on a variety of factors, including but not limited to an anatomy and tendencies of the subject (i.e., patient) in which the devices will be used, the size and shape of components with which the devices will be used, the methods and procedures in which the devices will be used, and the preferences of the surgeon operating the devices and/or otherwise performing the related procedure(s). For example, in at least some illustrated embodiments, a shape of a frame of a prosthetic implant is substantially elliptical, but a person skilled in the art will recognize that the frame may be configured to have other shapes (e.g., circular, rectangular), depending, at least in part, on the shape, size, and configuration of other components with which the frame is used (e.g., a prosthetic component), the anatomy in which the frame is being disposed (e.g., various bones), and the preferences of the surgeon, among other factors.

In the present disclosure, like-named components of the embodiments generally have similar features and/or purposes, unless stated otherwise. Additionally, several terms may be used throughout the disclosure interchangeably but will be understood by a person skilled in the art. Further, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can be easily determined for any geometric shape (e.g., references to widths and diameters being easily adaptable for circular and linear dimensions, respectively, by a person skilled in the art). Still further, to the extent that terms are used in the disclosure to describe a direction, orientation, and/or relative position of the disclosed prosthetic devices and components thereof and/or for performing a disclosed method of assembly and/or implantation of such devices, such terms are not intended to be limiting. For example, a person skilled in the art will recognize that terms of direction, orientation, and/or relative position (e.g., proximal, distal, medial, lateral, etc.) can be used interchangeably depending, at least in part, on the perspective view of the surgeon or other operator.

The present disclosure is generally related to prosthetic implants for augmenting or replacing a glenoid surface of a shoulder joint, and provides improvements over existing designs of such implants. As discussed in greater detail below, the provided for embodiments of the prosthetic implants generally include a frame or rim made of metal or other suitable material that is anchored to bone and allows a prosthetic glenoid component to attach to it. For example, in some embodiments, an anatomic glenoid component made of polyethylene can be configured to removably snap onto the frame. Among its benefits, the frame can improve fixation of such plastic components to bone as compared to conventional fixation techniques. The frame also allows a distal surface of the polyethylene component to have direct plastic-to-bone contact through an aperture of the frame, which can reduce stress shielding, glenoid loosening, and overall wear, among other benefits.

In some embodiments, the frame of the prosthetic implant can include, or be adapted to include, more than one attachment interface to convert from one type of glenoid component to another, while the frame remains anchored to bone. For example, as discussed in greater detail below, the frame can be utilized to facilitate an anatomic-to-reverse conversion of the shoulder joint by removing an anatomic glenoid component from a first attachment interface (e.g., a set of snap-fit connector interfaces) and attaching a reverse glenoid component to a second attachment interface (e.g., a removable frame adaptor, locking screw pockets, and/or anchoring pegs). Accordingly, the frame can allow a shoulder joint implant to be easily converted from an anatomic configuration to a reverse configuration.

Although the various embodiments disclosed herein involve an implant that includes a frame for fixing prosthetic components to the glenoid side of a shoulder joint, a person skilled in the art will understand how the disclosures provided for herein can be adapted to utilize a frame for fixing prosthetic components, e.g., a prosthetic head or cup, to the humeral side of the shoulder joint. A person skilled in the art will also understand how the disclosures provided for herein can be adapted for use with devices and procedures associated with other joints, such as but not limited to elbow, ankle, hip, and/or knee joints, without departing from the spirit of the present disclosure.

Figure 3A:
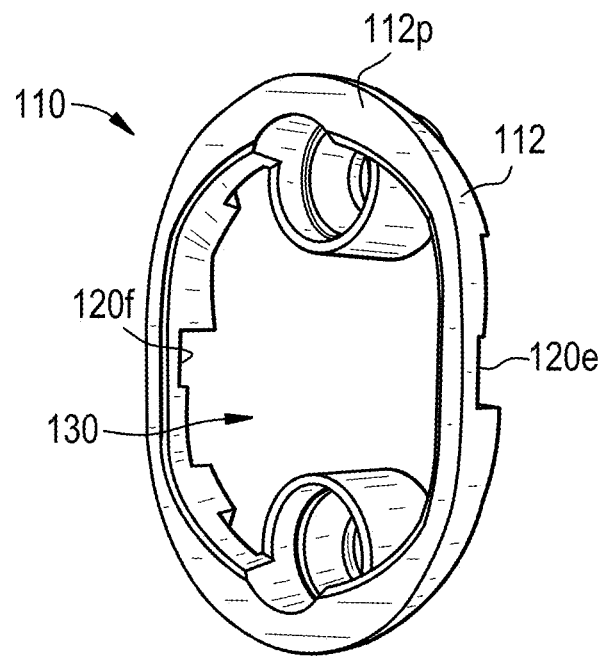
FIG. 3A is a front perspective view of the frame of FIG. 2D.
Figure 3B:
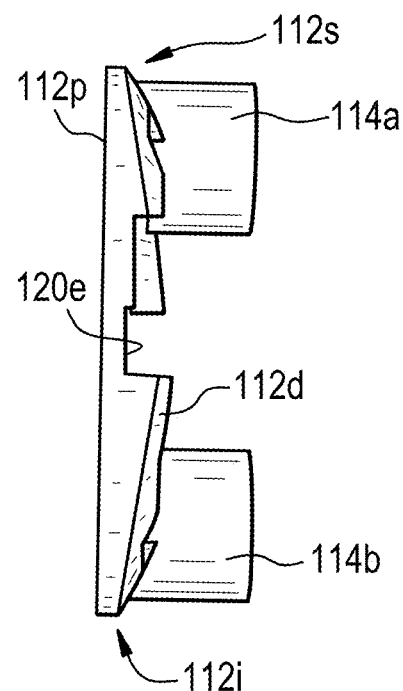
FIG. 3B is a side view of the frame of FIG. 3A.
Figure 3C:
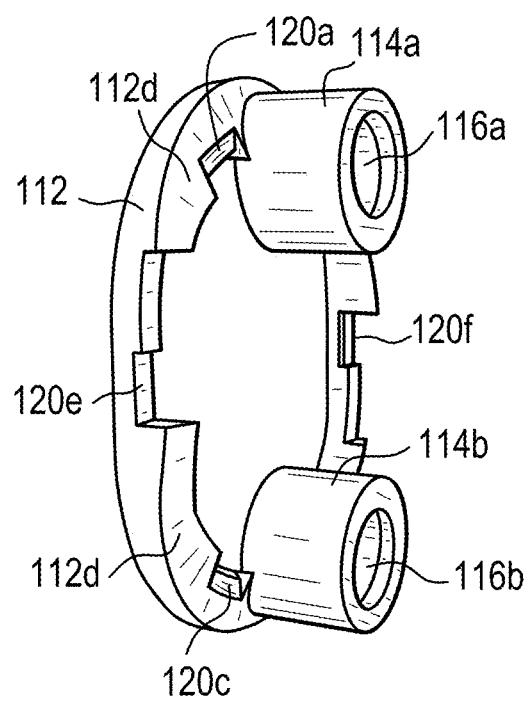
FIG. 3C is a rear perspective view of the frame of FIG. 3A.

FIGS. 2A-2D illustrate one exemplary embodiment of an anatomic shoulder joint implant 100. The prosthetic implant 100 can include a frame 110 and an anatomic glenoid component 150. The frame 110 can be anchored to bone and include multiple attachment interfaces 120 for attaching the glenoid component 150 to the frame. Additionally, the frame 110 can define an aperture 130 (see FIG. 3A) through which a distal portion 150d of the glenoid component 150 can have direct contact to bone when attached to the frame. As discussed in greater detail below, in some embodiments, the frame 110 can modified with a removable frame adaptor configured to allow the shoulder joint implant 100 to be converted to a reverse shoulder joint implant.

In the illustrated embodiment, the frame 110 is made of metal. Exemplary metals that can be used to manufacture the frame include, by way of non-limiting examples, titanium alloys (e.g., Ti-6Al-4V), tantalum, stainless steels (e.g., 316L), cobalt chrome, combinations thereof (or in combination with other materials), and/or any metal composite/alloy thereof. However, persons skilled in the art will recognize that other materials can be used to manufacture the frame including, without limitation, ceramics, polyethylenes, polycarbonate, polyetheretherketone, or any combinations involving these materials. The anatomic glenoid component 150 can be made of plastic or plastic material. Exemplary plastic materials that can be used to manufacture the anatomic glenoid component 150 can include, by way of non-limiting examples, polyethylene, polyethylenes, polycarbonate, polyetheretherketone, and combinations thereof (or in combination with other materials). However, persons skilled in the art will recognize that other materials can be used to manufacture the anatomic glenoid component, including without limitation titanium alloys (e.g., Ti-6Al-4V), tantalum, stainless steels (e.g., 316L), cobalt chrome, ceramics, coatings for hardness of frictional advantages, or any combination involving these materials.

As shown in greater detail in FIGS. 3A-3D, the frame 110 can have a generally annular shaped body 112. In the illustrated embodiment, the frame shape is substantially elliptical. However, a person skilled in the art will recognize that the frame may be configured to have other shapes (e.g., circular, rectangular), depending, at least in part, on the shape, size, and configuration of other components with which the frame is used (e.g., a prosthetic component), the anatomy in which the frame is being disposed (e.g., various bones), and the preferences of the surgeon, among other factors. The annular frame body 112 can have a substantially planar proximal surface 112p that provides a platform on which a proximal portion 150p of the anatomic glenoid component 150 can bear against when attached to the frame 110. The distal surface 112d of the annular frame body 112 can have a substantially convex shape configured to mate directly with a substantially concave surface of glenoid bone in a patient's scapula. One skilled in the art will recognize that the proximal surface 112p and the distal surface 112d of the annular frame body 112 can have different shapes or surface topologies, e.g., depending on the opposing surfaces of the prosthetic component and/or bone intended to engage the frame, among other factors.

The frame 110 can also include one or more bone anchor pockets used for anchoring the frame to bone. In the illustrated embodiment, a pair of bone anchor pockets 114a and 114b (collectively 114) are configured to project distally from substantially opposite ends of the annular fame body 112. As shown, the bone anchor pocket 114a can be disposed at a superior end 112s of the frame body 112 and the bone anchor pocket 114b can be disposed at an inferior end 112i. Each of the bone anchor pockets 114 can have a substantially tubular shape that defines a threaded or unthreaded through hole 116a and 116b (collective, 116). A poly-axial screw or other bone anchor (not shown) can be driven distally, or otherwise inserted, through the hole 116 for anchoring the frame 110 to bone. As shown, the bone anchor pockets 114 can be accessible through the aperture 130. Although a pair of bone anchor pockets 114 are shown, the frame can include more or less than two bone anchor pockets for anchoring the frame to bone. Alternatively, in some embodiments, the bone anchor pockets can be accessed outside the perimeter of the annular frame body 112, albeit at a cost of increasing the areal footprint of the frame.

The aperture 130 of the frame 110 can be defined by an inner wall of the annular frame body 112. In the illustrated embodiment, the aperture has a cross sectional profile with a generally elliptical shape, and can even, as shown for example in FIG. 3A, include a stepped configuration such that the aperture has a plurality of diameters depending on the depth within the aperture. Such a stepped configuration can assist in allowing a screw or the like to sit in an unobtrusive manner within the inner walls of the aperture, the stepped configuration being shaped to agree with a shape of the distal-facing surface of the screw. Alternatively, in some embodiments, the frame can define the aperture to have a cross sectional profile with a different shape(s), including without limitation, a rectangular, polygonal, circular, or bespoke shape, or a plurality of apertures in these possible shapes. The dimensions of the frame aperture 130 can be configured to maximize the contact surface area directly between the glenoid component 150 and bone. For example, in some embodiments, the frame aperture 130 can be configured to have a cross-sectional area approximately in the range of about 20 square millimeters to about 2400 square millimeters. In some embodiments, the cross-sectional area of the frame aperture 130 can be equal to a percentage of a total cross-sectional area or footprint encompassed by the frame 110 approximately in the range of about 10 percent to about 99 percent. In some embodiments, the cross-sectional profile of the frame aperture 130 can have a maximum length 130L approximately in the range of about 20 millimeters to about 60 millimeters and a maximum width 130W approximately in the range of about 20 millimeters to about 40 millimeters.

Figure 3D:
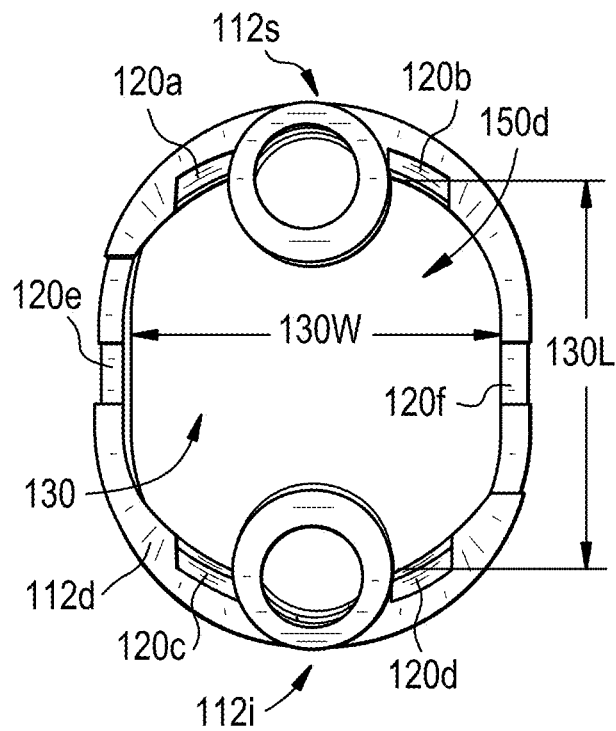
FIG. 3D is a rear view of the frame of FIG. 3A.

In the illustrated embodiment, the frame 110 includes multiple snap-fit connector interfaces 120a, 120b, 120c, 120d, 120e, and 120f (collectively 120) for attaching the anatomic glenoid component 150 to the frame 110. As shown in FIG. 3D, the snap-fit connector interfaces 120 can be defined in the distal surface 112d of the annular frame body 112. The snap-fit connector interfaces 120 can be configured as slots, grooves, or other recesses, and can sometimes be referred to as female coupling components, connectors, or interfaces. As described in more detail with respect to FIGS. 4A-4D, the snap-fit connector interfaces 120 can be configured to allow corresponding snap-fit connectors of the anatomic glenoid component 150 to interlock or otherwise engage the frame 110 when pressed together.

The snap-fit connector interfaces 120 of the frame 110 can be evenly distributed about the distal surface 112d of the annular body. For example, in the illustrated embodiment, two snap-fit connector interfaces 120a and 120b are defined at the superior end 112s of the annular frame body 112 adjacent to the bone anchor pocket 114a, two snap-fit connector interfaces 120c and 120d are defined at the inferior end 112i of the annular frame body adjacent to the bone anchor pocket 114b, and two snap-fit connector interfaces 120e and 120f are defined on opposing legs of the annular frame body between the superior and inferior ends. Although the figures show the frame 110 as including six snap-fit connector interfaces 120, the frame can include more or less than six snap-fit connector interfaces (e.g., 1, 2, 3, 4, 5, 7, 8, 9, 10, etc.) defined at various locations in the distal surface 112d of the annular body 112. Alternatively, or additionally, in some embodiments, one or more of the snap-fit connector interfaces 120 can be defined in the proximal surface 112p of the annular body 112.

As shown in FIGS. 4A-4D, the anatomic glenoid component 150 can have a generally disc-shaped body that includes a proximal portion 150p and a distal portion 150d. The proximal portion 150p can have a proximal-bearing surface 152 upon which a prosthetic head (e.g., 14 of FIG. 1A) of a humeral prosthesis (e.g., 10 of FIG. 1A) can articulate. The proximal-bearing surface 152 can have a substantially concave shape that substantially mimics the concavity of healthy glenoid bone. The proximal portion 150p can define a distal-facing ridge 154 at an interface between the proximal and distal portions 150p, 150d of the glenoid component 150. The ridge 154 can serve as a stop that bears against the proximal surface 112p of the frame 110 when the glenoid component 150 is attached to the frame 100. In the illustrated embodiment, the ridge 154 projects outward at a superior end 150s and at an inferior end 150i of the component 150.

The distal portion 150d of the anatomic glenoid component 150 can have a bespoke shape configured for insertion into the aperture 130 of the frame 110. For example, in the illustrated embodiment, the bespoke shape of the distal portion 150d has a cross sectional profile configured to generally form a negative of the cross-sectional profile of the frame aperture 130. The distal portion 150 can also define recesses (or cut-away portions) 150r configured to circumscribe (or at least partially circumscribe) the bone anchor pockets 114 and thus prevent the pockets from interfering during attachment of the glenoid component 150 to the frame 110. The distal portion 150d can have a generally convex-shaped distal bearing surface 156 configured to mate directly with a substantially concave surface of glenoid bone in a patient's scapula and thus maximize the contact surface area between the glenoid component 150 and glenoid bone.

One skilled in the art will recognize that the distal bearing surface 156 of the anatomic glenoid component 150 can have a different shape or surface topology, e.g., depending on the opposing surface topology of the target bone. In some embodiments, the distal portion 150d of glenoid component 150 can include a bone engaging post 158 that projects outward from the distal bearing surface 156. As described in greater detail below, the bone engaging post 158 can be configured to engage a hole or void drilled into glenoid bone. Although one bone engaging post 158 is shown in the figures, more or less than one bone engaging post can be configured to project from the distal bearing surface 156 of the anatomic glenoid component 150 (e.g., 0, 2, 3, 4 or more posts).

Figure 4A:
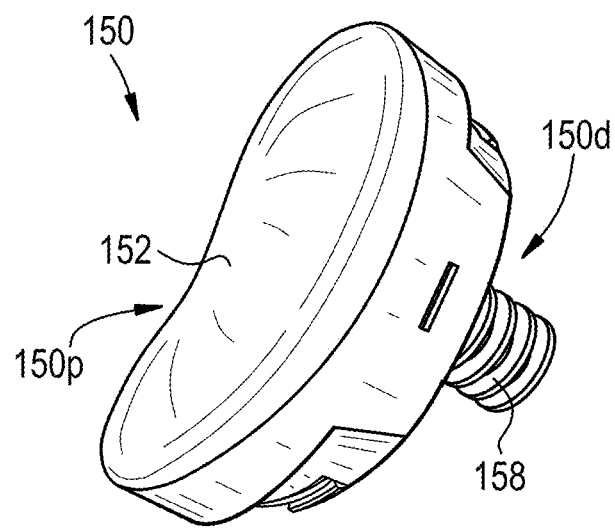
FIG. 4A is a front perspective view of the anatomic glenoid component of FIG. 2D.
Figure 4B:
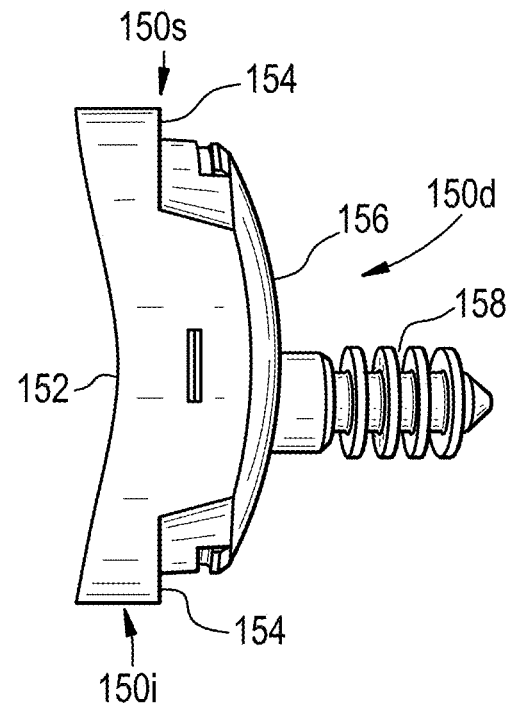
FIG. 4B is a side view of the anatomic glenoid component of FIG. 4A.
Figure 4C:
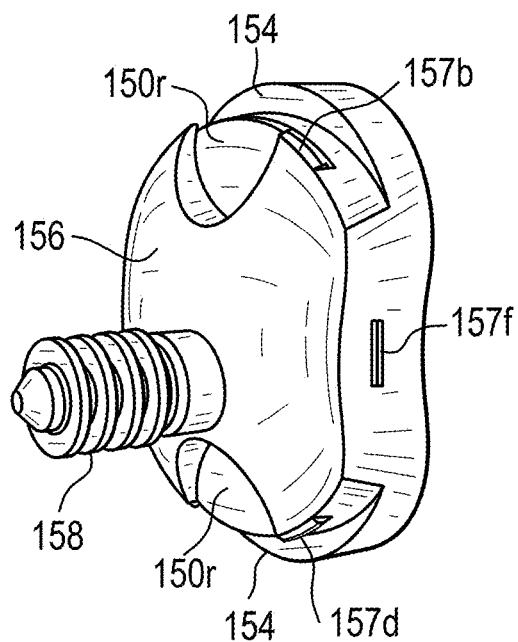
FIG. 4C is a rear perspective view of the anatomic glenoid component of FIG. 4A.
Figure 4D:
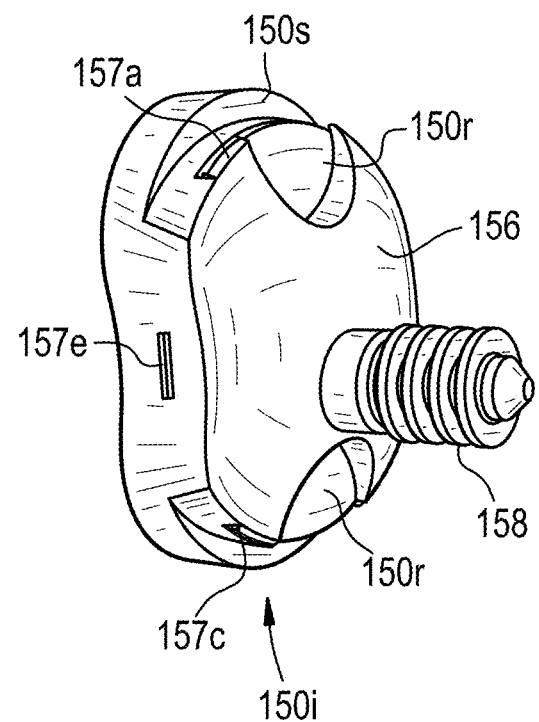
FIG. 4D is a second rear perspective view of the anatomic glenoid component of FIG. 4A.

As discussed above, the frame 110 can include multiple snap-fit connector interfaces 120 for attaching the anatomic glenoid component 150 to the frame. Referring to FIGS. 4C and 4D, the anatomic glenoid component 150 can include multiple snap-fit connectors 157a, 157b, 157c, 157d, 157e, and 157f (collectively 157) configured to interlock or otherwise engage the corresponding snap-fit connector interfaces 120a, 120b, 120c, 120d, 120e, and 120f (collectively 120) of the frame 110. In the illustrated embodiment, each of the snap-fit connectors 157 can be a tongue or protrusion projecting laterally from the distal portion 150d of the prosthetic component 150 and configured to snap into the frame 110 at the locations of the snap-fit connector interfaces 120. The connectors 157 can sometimes be referred to as male coupling components, connectors, or interfaces. Persons skilled in the art will recognize that the snap-fit connectors 157 can have alternative shapes and/or configurations for engaging the snap-fit connector interfaces 120 when the anatomic glenoid component 150 is pressed onto the frame 110. By way of non-limiting example, the male and female connections can be reversed between the two components 110, 150.

Figure 5A:
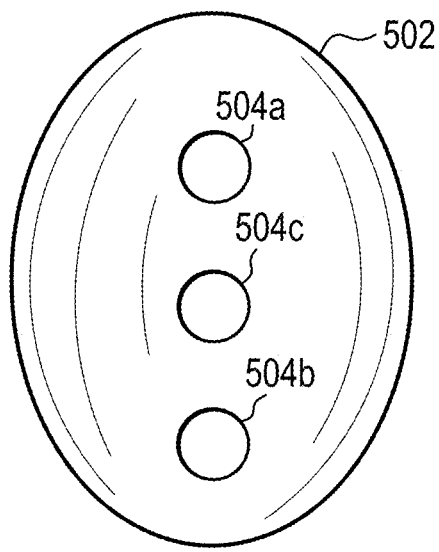
FIGS. 5A, 5B, and 5C are schematic illustrations of one exemplary embodiment of a method of deploying an anatomic shoulder joint implant into a patient, like the anatomic shoulder joint implant of FIG. 2A.
Figure 5B:
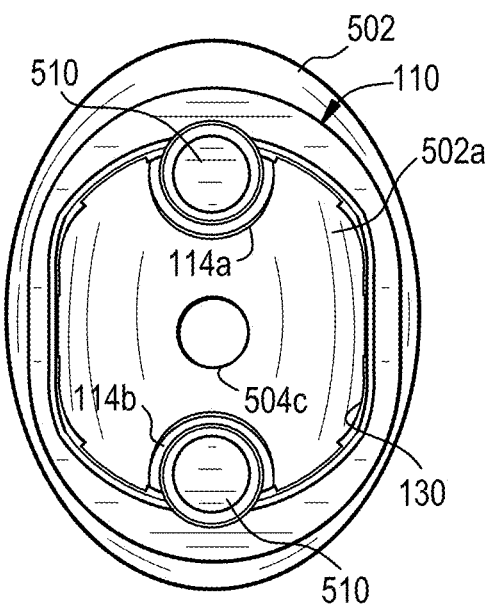
Figure 5C:
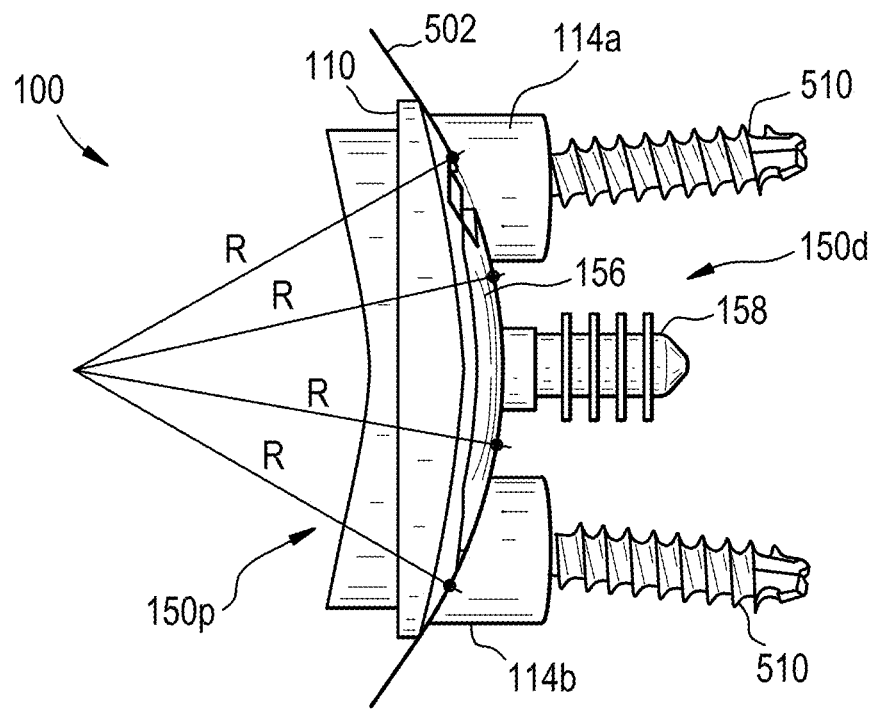
Figure 6A:
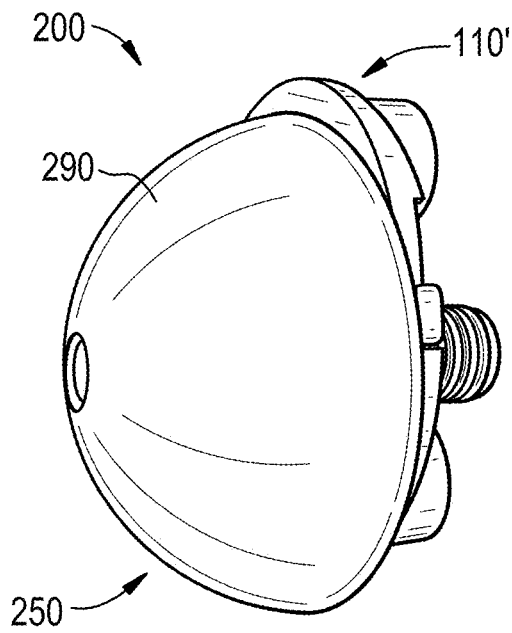
FIG. 6A is a front perspective view of one exemplary embodiment of a reverse shoulder joint implant, the implant including a frame similar to the frame of FIG. 3A.
Figure 6B:
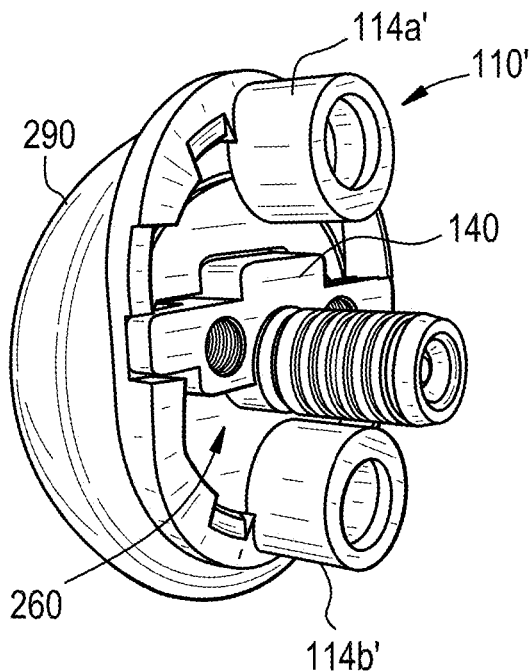
FIG. 6B is a rear perspective view of the reverse shoulder joint implant of FIG. 6A.
Figure 6C:
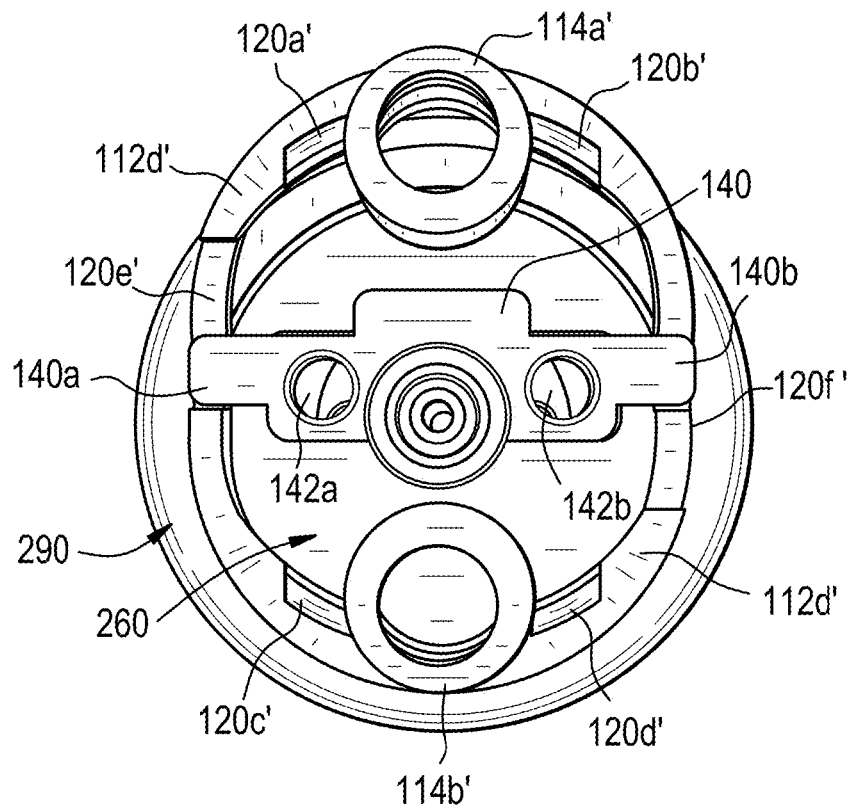
FIG. 6C is a rear view of the reverse shoulder joint implant of FIG. 6A.
Figure 6D:
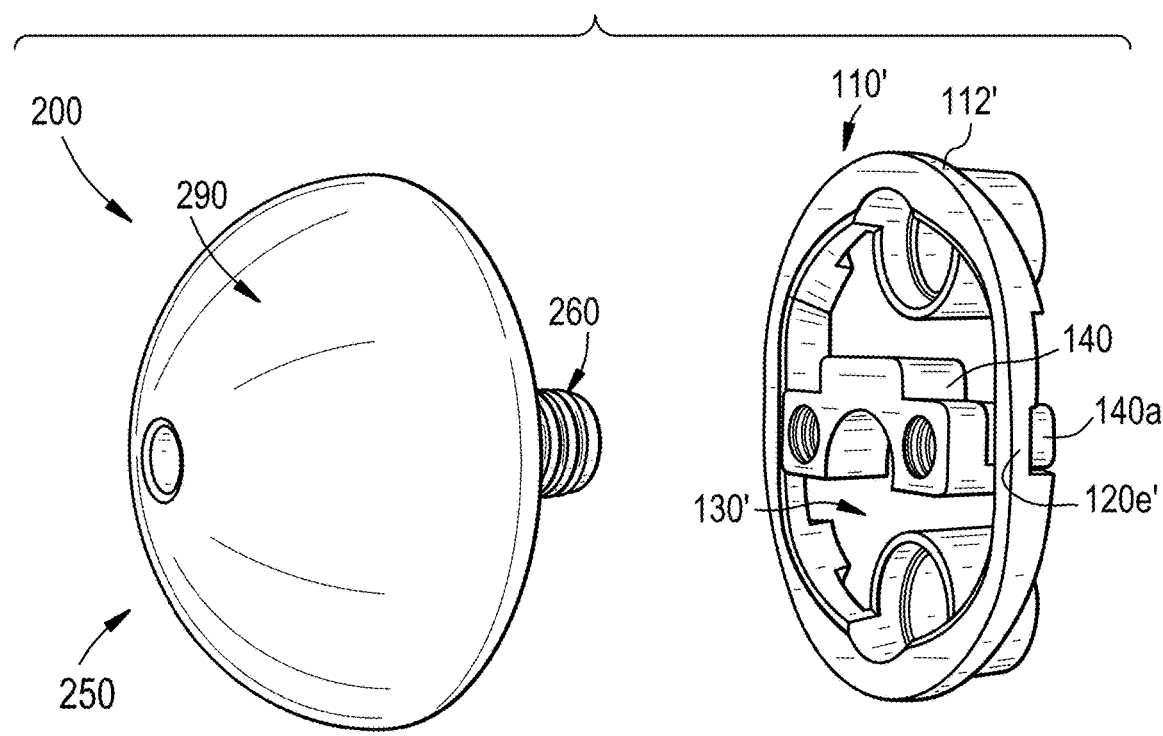
FIG. 6D is a perspective exploded view of components of the reverse shoulder joint implant of FIG. 6A, the components including the frame of FIG. 6A, a removable attachment bar, and a reverse glenoid component.

FIGS. 5A-5C are schematic illustrations of an exemplary embodiment of a method of deploying the anatomic shoulder joint implant 100 in a patient's scapula. In the illustrated embodiment, the anatomic shoulder joint implant 100 can be implanted as part of anatomic total shoulder joint arthroplasty procedure, such that the implant 100 is secured to glenoid bone of the patient's scapula to provide a corresponding concave bearing surface for a prosthetic head of a humeral prosthesis (e.g., 14 of FIG. 1A). Although the illustrated method uses the implant 100 described above, at least some of the components associated with or otherwise used in conjunction with the implant 100 may not be easily visible. In view of the disclosures provided for herein, and their related illustrations, a person skilled in the art will understand how the various components of the implant 100 engage the various portions of the patient's anatomy, and/or the components of the implant 100 and related tool(s) used in conjunction with the procedures disclosed with respect to FIGS. 5A-5C.

Referring to FIG. 5A, glenoid bone 502 of a patient's scapula can be prepared to have an approximately smooth, concave surface for mounting the implant 100. Persons skilled in the art will recognize that a reamer (not shown) or other tool(s) can be used to prepare the concave surface of the glenoid bone 502 to mate with the convex-shaped distal surfaces of the frame 110 and the anatomic glenoid component 150. Additionally, one or more holes or voids 504a, 504b, 504c can be drilled into the glenoid bone 502 for mounting the implant 100 (as shown, three). For example, the holes 504a and 504b can be configured to receive the tubular-shaped bone anchor pockets 114a and 114b of the frame 110, and the hole 504c can be configured to receive the bone engaging post 158 of the anatomic glenoid component 150. In some embodiments, a person skilled in the art will recognize a stop drill aligned with a guide pin and/or a guide plate (not shown) can be used to drill the holes, among other tool(s).

Referring to FIG. 5B, the frame 110 can be anchored to the glenoid bone 502. For example, in the illustrated embodiment, the frame 110 can be anchored to bone by inserting the bone anchor pockets 114a and 114b into the drilled holes 504a and 504b. Thereafter, a poly-axial bone screw 510 or other bone anchor can be driven distally, or otherwise inserted, into the glenoid bone 502 through each pocket. In some embodiments, a screw driver (not shown) can be used to drive the bone screws 510 into the glenoid bone. Once the frame 110 is anchored to the bone, the frame aperture 130 can expose a concave-shaped portion 502a of the glenoid bone 502 that includes the hole 504c.

Referring to FIG. 5C, the anatomic glenoid component 150 can be attached to the frame 110 such that the distal portion 150d of the glenoid component is in direct contact with the glenoid bone 502a through the frame aperture 130. For example, as shown, the convex-shaped distal surface 156 and the post 158 of the glenoid component can be in direct contact with the glenoid bone 502a through the frame aperture 130. By configuring the convex-shaped distal surface 156 of the glenoid component 150 and the convex-shaped distal surface 112d of the frame 110 to have the same, or substantially the same, radius of curvature R, direct component-to-bone contact surface area can be maximized.

In some embodiments, the anatomic glenoid component 150 can be attached to the frame 110 by inserting the post 158 into the drilled hole 504c through the aperture 130 and distally pressing the component through the aperture 130 until it snaps onto the frame. For example, the anatomic glenoid component 150 can snap onto the frame when the snap-fit connectors 157 of the component (not visible) interlock with or otherwise engage the snap-fit connector interfaces 120 (not visible) of the frame 110. The post 158 can be slightly oversized relative to the diameter of the drilled hole 504c, which can enable a press fit.

As discussed above, in some clinical situations, it may be necessary to perform a reverse total shoulder arthroplasty that involves reversing the anatomy or structure of a patient's shoulder joint. For example, on the glenoid side, a reverse glenoid implant including a hemispherical-shaped glenosphere (i.e., the "ball" in a ball-and-socket joint) can be secured to the glenoid bone of the patient's scapula. In some patients, an anatomic-to-reverse conversion may be necessary to replace a previously deployed anatomic glenoid implant with a reverse glenoid implant. Such replacement typically involves a procedure that is complex and challenging due to the independent configurations and components of the respective implants. Thus, as described in more detail with respect to FIGS. 6A-6D, a reverse shoulder joint implant is provided for herein that can be configured to re-use a previously anchored frame (e.g., 110) of an anatomic shoulder joint implant (e.g., 100) to facilitate anatomic-to-reverse conversions in a manner that can avoid such complexities.

FIGS. 6A-6D illustrate an exemplary embodiment of a reverse shoulder joint implant 200. The prosthetic implant 200 can include a frame 110', a frame adaptor 140, and a reverse glenoid component 250. In the illustrated embodiment, the frame 110' includes an annular shaped body 112', bone anchor pockets 114a' and 114b' (collectively 114'), and snap-fit connector interfaces 120a', 120b', 120c', 120d', 120e', and 120f' (collectively 120') defined in the annular frame body. Except as described below or as will be readily appreciated by a person skilled in the art, the frame 110' is the same or substantially the same as the frame 110 described above. Thus, a detailed description of the structure and function of the frame 110' is omitted here for the sake of brevity.

In some embodiments, the frame adaptor 140 can be a removable attachment bar configured to extend substantially horizontal across the frame aperture 130' between the opposing legs of the of the frame 110'. For example, in the illustrated embodiment, the frame adaptor 140 is configured to extend across the frame aperture 130' such that the terminal ends 140a and 140b of the frame adaptor 140 are received within corresponding recesses 120e' and 120f' defined in distal surface 112d' of the annular frame body 112'. In some embodiments, the recesses 120e' and 120f' can be the same as the snap-fit connector interfaces 120e and 120f described above with respect to FIGS. 3A-3D.

The frame adaptor 140 can define a pair of locking screw holes 142a and 142b (collectively, 142) configured to receive corresponding locking screws (not shown) for attaching the reverse glenoid component 250 to the frame 110'. Although two locking screw holes 142 are shown in the figures, more or less than two locking screw holes (e.g., 1, 3, 4, 5, 6 or more locking screw holes) can be defined in the frame adaptor 140. In some embodiments, the frame adaptor 140 can have a cross-sectional shape that allows the frame adaptor to serve as an alignment key. For example, in the illustrated embodiment, the frame adaptor 140 has a T-shaped cross section configured to be received within a corresponding T-shaped recess (e.g., 262r of FIG. 7B) defined in the reverse glenoid component 250.

Figure 7A:
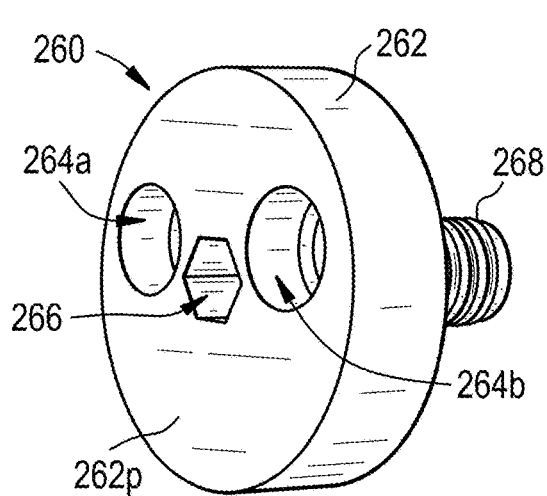
FIG. 7A is a front perspective view of a part of the reverse glenoid component of FIG. 6C, sometimes referred to herein as a metaglene.
Figure 7B:
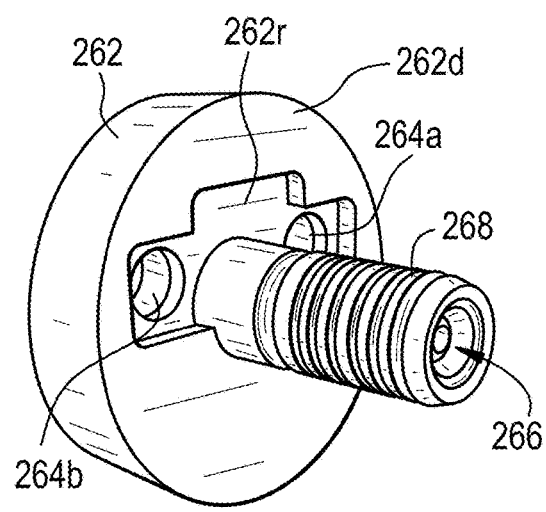
FIG. 7B is a rear perspective view of the metaglene of FIG. 7A.

The reverse glenoid component 250 can include a baseplate 260 and a hemispherical-shaped prosthetic head 290 coupled to the baseplate. A person skilled in the art, in view of the present disclosure, will understand the reverse glenoid component 250 to be a prosthetic component as provided for herein, with the baseplate 260 being part of, or coupled to, a distal-facing surface of the prosthetic component, and the hemispherical-shaped prosthetic head 290 being part of, or coupled to, a proximal-bearing surface of the prosthetic component. As shown in FIGS. 7A and 7B, the baseplate 260, sometimes referred to herein as a "metaglene," can include a generally disc-shaped platform 262 and a cylindrical-shaped post 268 extending outwardly from its distal surface 262d. One or more through holes can be defined to extend through the proximal and distal surfaces 262p and 262d of the metaglene platform 262. In the illustrated embodiment, a pair of through holes 264a and 264b (collectively, 264) are defined in the metaglene platform 262 and configured to align with the corresponding locking screw holes 142a and 142b of the frame adaptor 140. Although two through holes 264 are shown in the figures, more or less than two through holes can be defined in the metaglene platform 262 (e.g., 1, 3, 4, 5, 6 or more through holes), e.g., depending on the number of locking screw holes defined in the frame adaptor.

In some embodiments, the distal surface 262d of the metaglene platform 262 can define a recess 262r having a cross sectional shape that generally forms a negative of the cross-sectional shape of frame adaptor 140. In the illustrated embodiment, the recess 262r has a T-shaped cross section configured to receive the T-shaped frame adaptor 140. In some embodiments, the through holes 264 of the metaglene platform 262 can be aligned with the locking screw holes 142 of the frame adaptor 140 by orienting the recess 262r to mate with the frame adaptor.

The cylindrical-shaped post 268 can be configured to project substantially normal to the distal surface 262d of the metaglene platform 262. The post 268 can be configured to be implanted into a hole or void formed in bone, e.g., glenoid bone of patient's scapula. In some embodiments, a central bore 266 can be defined to extend through the metaglene platform 262 and at least partially along the length of the post 268. As discussed in more detail below, the central bore 266 can be configured to receive a coupling element for securing the prosthetic head 290 to the metaglene 260.

Figure 8A:
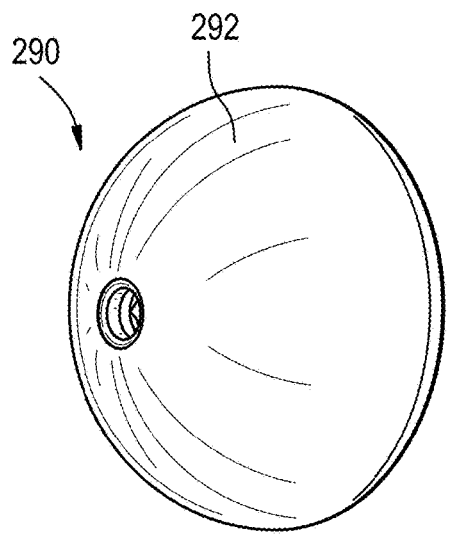
FIG. 8A is a front perspective view of another part of the reverse glenoid component of FIG. 6C, sometimes referred to herein as a glenosphere.
Figure 8B:
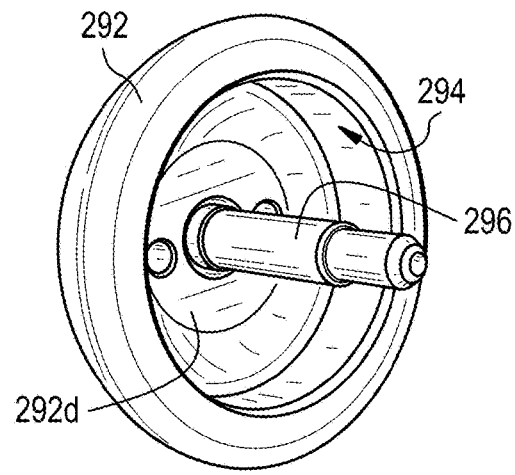
FIG. 8B is a rear perspective view of the glenosphere of FIG. 8A.

As shown in FIGS. 8A and 8B, the prosthetic head 290, sometimes referred to herein as a "glenosphere," can have a substantially hemispherical-shaped body 292. To attach the glenosphere 290 to the metaglene 260, the glenosphere body 292 can define an open-ended cavity 294 that is configured to mate with the disc-shaped metaglene platform 262. In some embodiments, the glenosphere 290 and the metaglene 260 can be configured to form a taper lock when the metaglene platform 262 is received within the cavity 294.

Alternatively, or additionally, a coupling element 296 for attaching the glenosphere 290 to the metaglene 260 can distally project from a distal-facing surface 292d of the glenosphere body 292. As shown in the illustrated embodiment, the coupling element 296 can be a threaded or unthreaded shaft configured to lock within the bore 266 of the metaglene 260. For example, in some embodiments, the glenosphere 290 can be manipulated to screw or press-fit the coupling element 296 into the bore 266 of the metaglene 260. Persons skilled in the art will recognize the glenosphere and the metaglene can be attached together using other techniques and/or mechanisms for securing one component with respect to another.

In some embodiments, any and all of the metaglene 260 and the glenosphere 290 can be made from any number of implantable metallic materials or other biocompatible materials to form the implant. Some non-limiting examples of materials suitable for forming the various components implant can include titanium, tantalum, cobalt-chrome, stainless steel, and other metals known to those skilled in the art, and some plastic materials, such as but not limited to, polyetheretherketone (PEEK) and Ultra High Molecular Weight Polyethylene (UHMWPE). In some instances, the various components (e.g., the metaglene 260 and the glenosphere 290) can be made from the same material, while in other embodiments one or more components can be made from different materials. Additionally, a person skilled in the art will recognize that a number of different material blends can be used to form any component of the implants provided for herein or otherwise derivable from the present disclosures.

FIGS. 9A-9D are schematic illustrations of an exemplary embodiment of a method of deploying the reverse shoulder joint implant 200 in a patient's scapula. In the illustrated embodiment, the reverse shoulder joint implant 200 can be deployed as part of anatomic-to-reverse conversion of a total shoulder joint arthroplasty in which the anatomic glenoid component 150 of the anatomic shoulder joint implant 100 is removed and replaced with the reverse glenoid component 250. Although the illustrated embodiment describes an anatomic-to-reverse conversion, a person skilled in the art will recognize that the reverse shoulder implant 200 provided for herein can be deployed without having to previously deploy an anatomic glenoid implant.

Figure 9A:
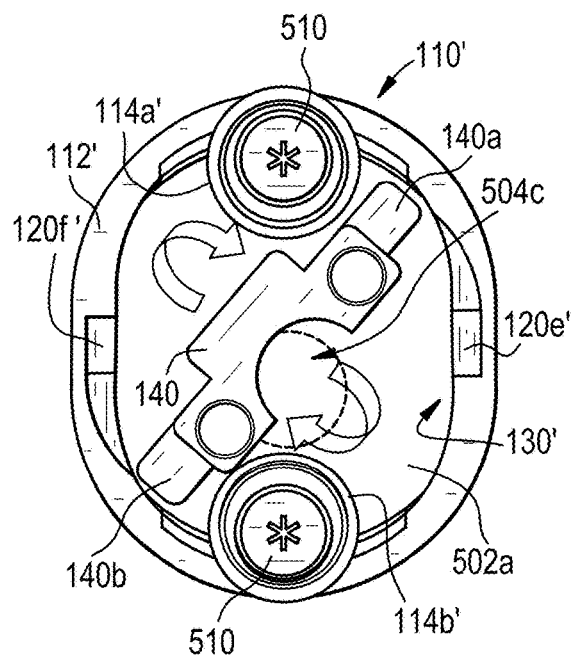
FIGS. 9A, 9B, 9C, and 9D are schematic illustrations of one exemplary embodiment of a method of deploying a reverse shoulder joint implant into a patient, like the reverse shoulder joint implant of FIG. 6A.
Figure 9B:
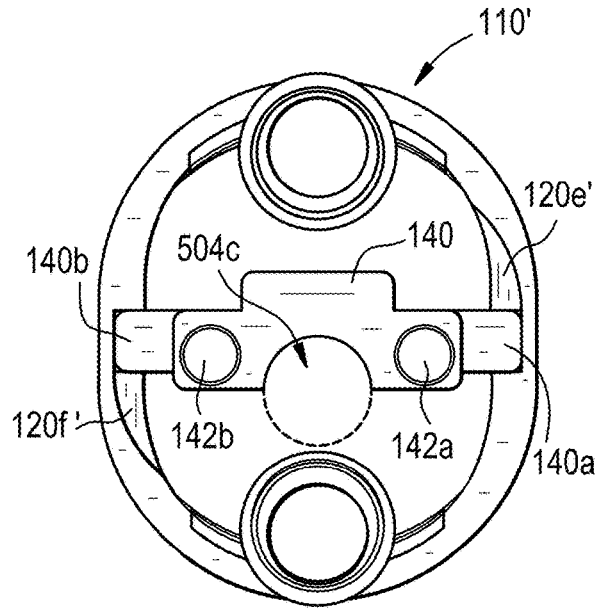

Referring to FIGS. 9A and 9B, the frame 110' is shown anchored to glenoid bone 502 and exposing a concave-shaped portion 502a of the glenoid bone, including a drilled hole 504c'. In the illustrated embodiment, the frame 110' is anchored to bone by poly-axial bone screws 510 inserted through the bone anchor pockets 114a, 114b. In the illustrated anatomic-to-reverse conversion, the anchored frame 110' can be the same as the frame (e.g., 110) previously deployed as part of an anatomic total shoulder arthroplasty described above with respect to FIGS. 5A-5C. An anatomic glenoid component 150 (not shown) of a previously deployed anatomic glenoid implant can be removed in a prior processing step.

The frame adaptor 140 can be inserted into the aperture 130' of the frame 110' (shown in partial transparency). Once inserted, the frame adaptor 140 can be manipulated such that the adaptor extends substantially horizontal across the frame aperture 130' between the opposing legs of the of the frame 110'. For example, as shown in the illustrated embodiment, the frame adaptor 140 can be manipulated within the frame aperture 130' such that the terminal ends 140a and 140b of the frame adaptor 140 are received within corresponding recesses 120e' and 120f' defined in distal surface of the annular frame body 112'. In some embodiments, the recesses 120e' and 120f' can be defined to provide clearance for the frame adaptor 140 as it is rotated into horizontal alignment within the frame 110'. In some embodiments, the cross-sectional profile of the frame adaptor 140 can be configured to at least partially circumscribe the hole 504c' when the adaptor is aligned in the opposing recesses 120e' and 120f' of the frame 110.

Figure 9C:
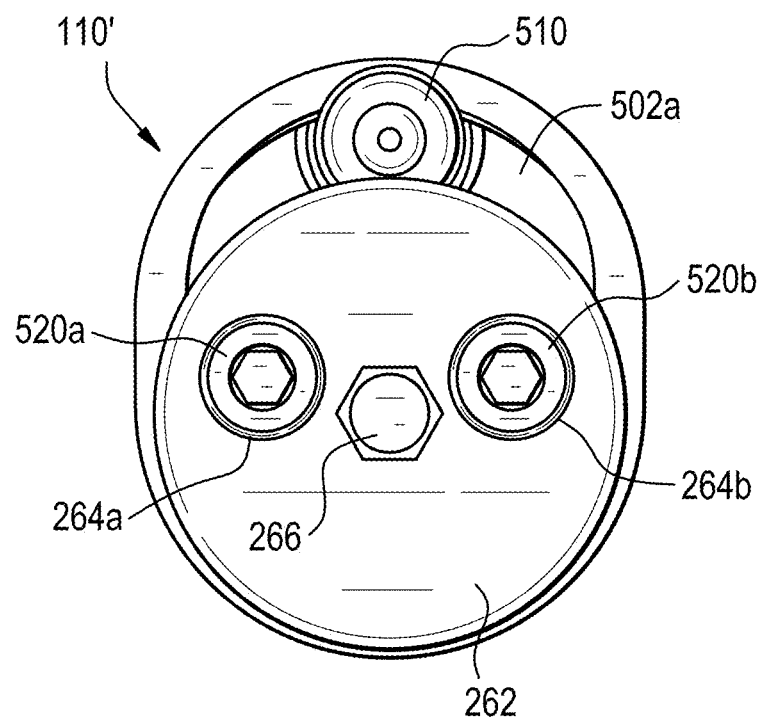

Referring to FIG. 9C, the metaglene 260 can be mounted on the frame 110 such that the post 268 (shown in FIG. 9D) is inserted into the drilled hole 504c and through holes 264a and 264b are aligned with the locking screw holes 142a and 142b of the frame adaptor 140. In some embodiments, the through holes 264 of the metaglene 260 and the locking screw holes 142 of the frame adaptor 140 can be aligned by orienting the metaglene platform 262 such that a recess 262r (see FIG. 7B) defined in its distal surface mates with the frame adaptor 140. Locking screws 520a and 520b (collectively 520) can be driven distally, or otherwise inserted, into the through holes 264 of the metaglene platform 262 and into the locking screw holes 142 of the frame adaptor 140. As the locking screws 520 are inserted into the frame adaptor 140, the metaglene platform 262 and the frame adaptor 140 can move towards one another such that they are pressed against the annular frame body 112'.

Figure 9D:
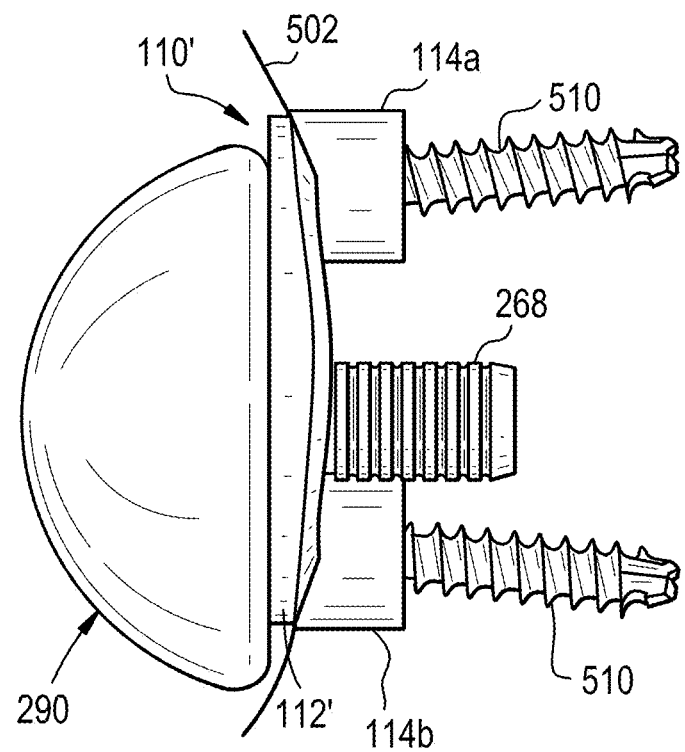
Figure 10A:
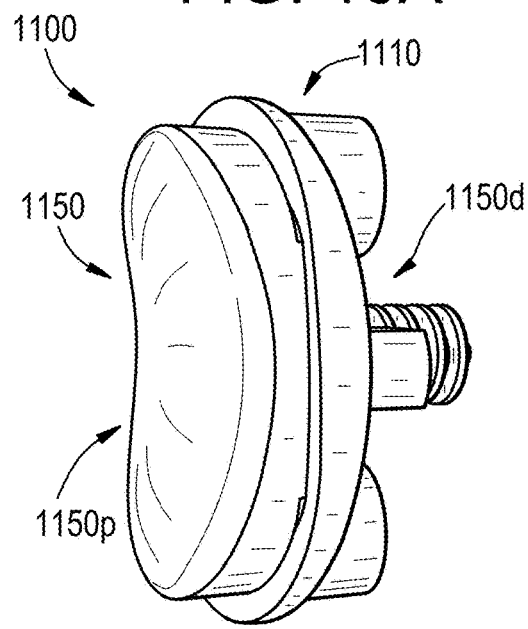
FIG. 10A is a front perspective view of another exemplary embodiment of an anatomic shoulder joint implant.
Figure 10B:
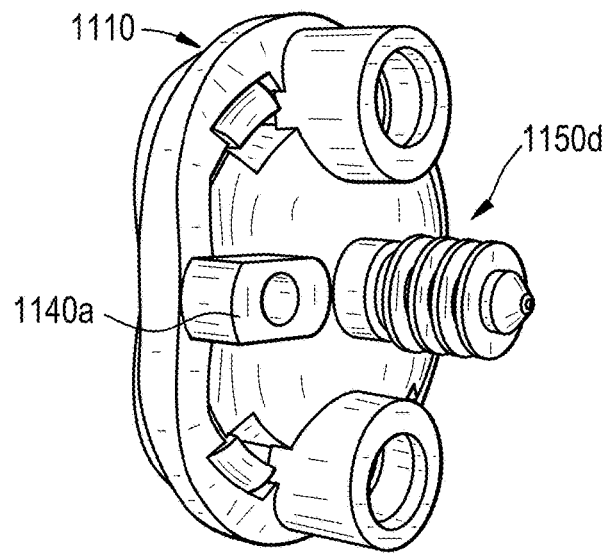
FIG. 10B is a rear perspective view of the anatomic shoulder joint implant of FIG. 10A.
Figure 10C:
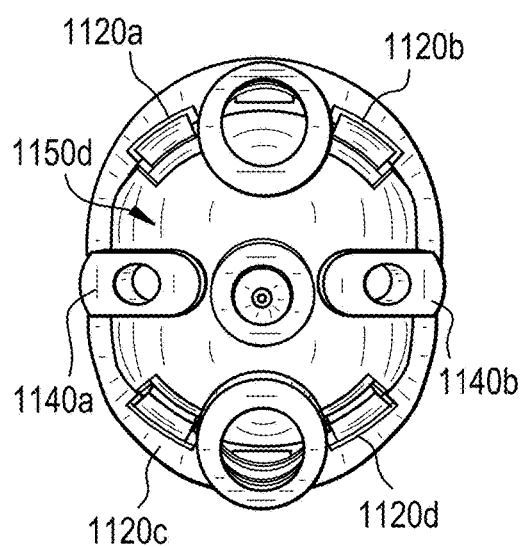
FIG. 10C is a rear view of the anatomic shoulder joint implant of FIG. 10A.
Figure 10D:
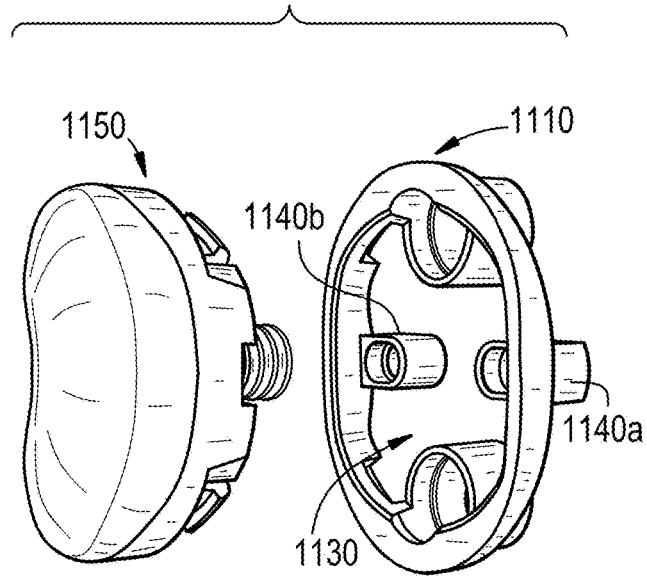
FIG. 10D is a perspective exploded view of components of the anatomic shoulder joint implant of FIG. 10A, the components including an anatomic glenoid component and a frame.
Figure 11A:
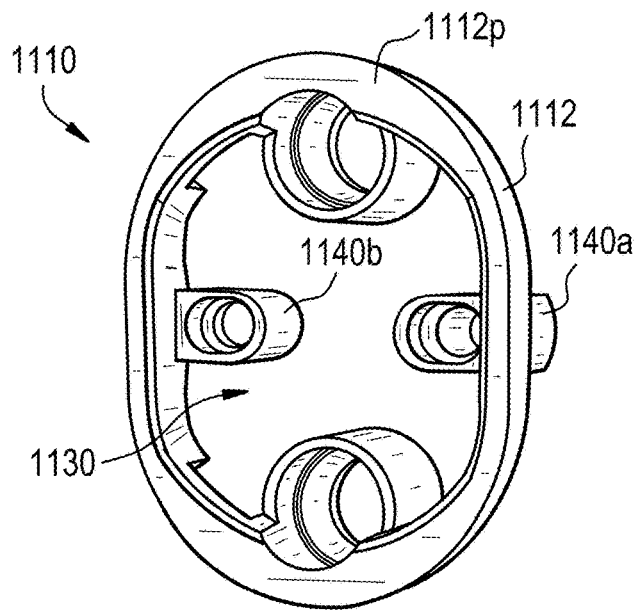
FIG. 11A is a front perspective view of the frame of FIG. 10C.
Figure 11B:
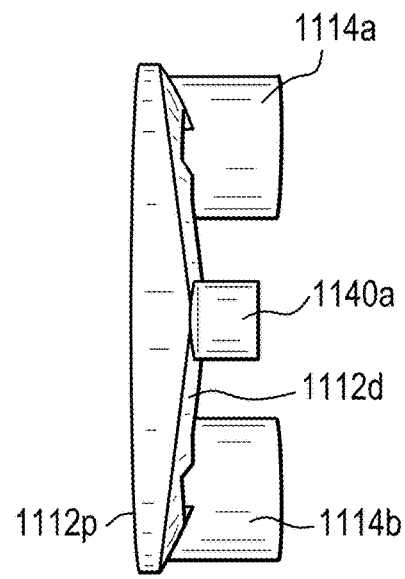
FIG. 11B is a side view of the frame of FIG. 11A.
Figure 11C:
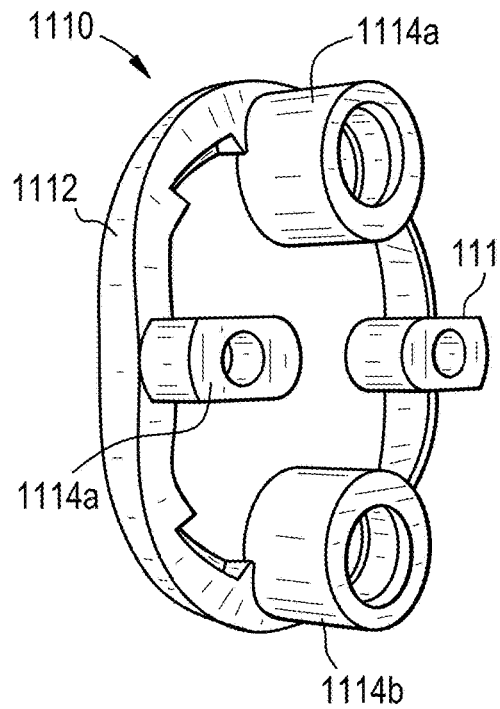
FIG. 11C is a rear perspective view of the frame of FIG. 11A.
Figure 11D:
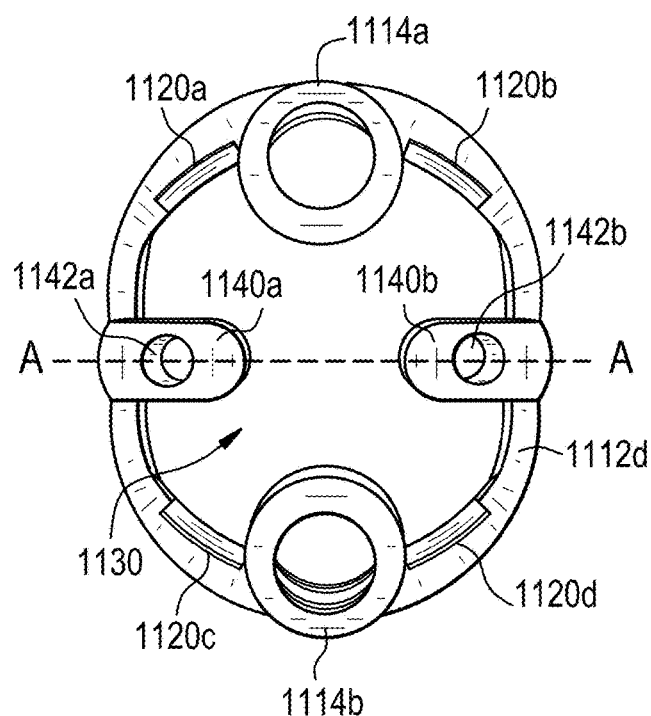
FIG. 11D is a rear view of the frame of FIG. 11A.
Figure 12A:
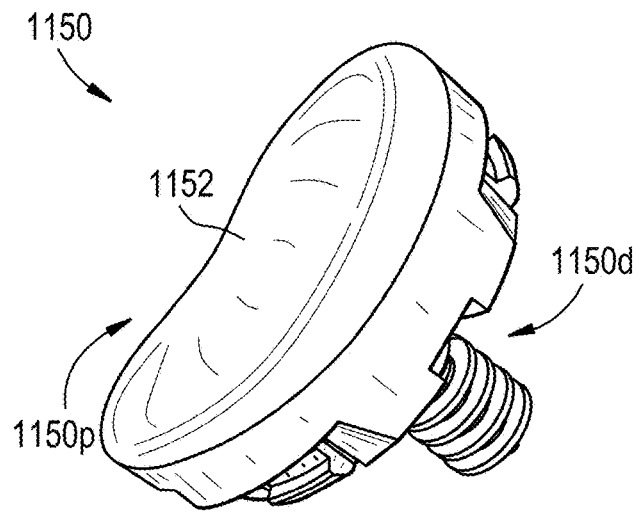
FIG. 12A is a front perspective view of the anatomic glenoid component of FIG. 10C.
Figure 12B:
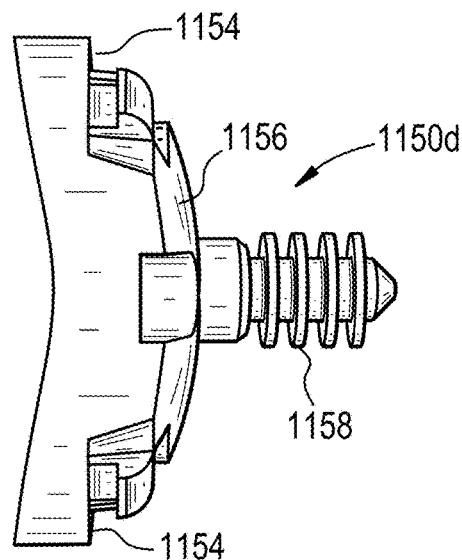
FIG. 12B is a side view of the anatomic glenoid component of FIG. 12A.
Figure 12C:
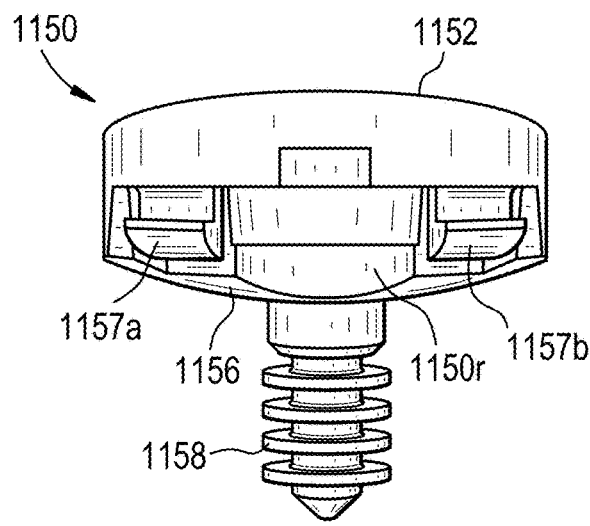
FIG. 12C is a front view of the anatomic glenoid component of FIG. 12A (the rear view of the anatomic glenoid component is a mirror image of the front view as shown)
Figure 12D:
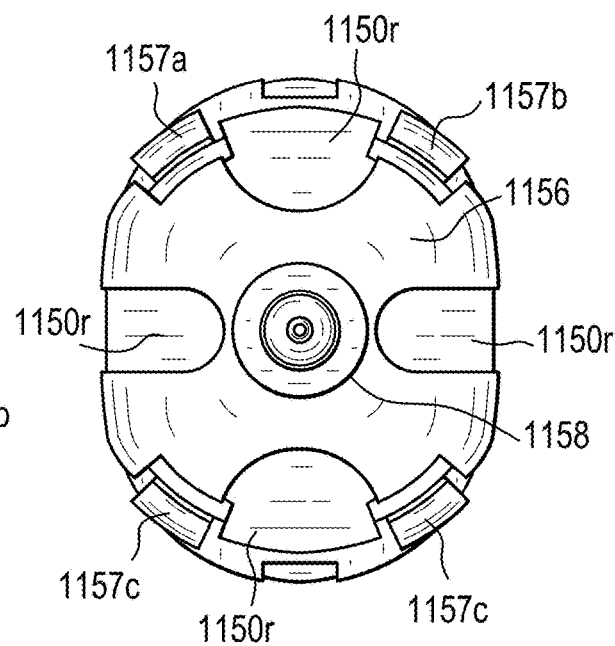
FIG. 12D is a rear view of the anatomic glenoid component of FIG. 12A.

Referring to FIG. 9D, the glenosphere 290 can be attached to the metaglene 260. For example, in some embodiments, a coupling element 296 (not visible) of the glenosphere body 292 can be screwed or press fit into a central bore 266 (FIG. 9C) of the metaglene 260. Additionally, or alternatively, the glenosphere 290 and the metaglene 260 can form a taper lock when the disc-shaped metaglene platform 262 is received within a cavity 294 (not visible) defined in the glenosphere body 292.

FIGS. 10A-10D illustrate another exemplary embodiment of an anatomic shoulder joint implant 1100. The prosthetic implant 1100 can include a frame 1110 and an anatomic glenoid component 1150. The frame 1110 can be anchored to bone and include multiple attachment interfaces 1120 for attaching the anatomic glenoid component 1150 to the frame. In addition, the frame 1110 can define an aperture 1130 through which a distal portion 1150d of the glenoid component 1150 can have direct contact with bone when attached to the frame. As discussed in greater detail below, in some embodiments the frame 1110 can be configured to allow the shoulder joint implant 1100 to be converted to a reverse shoulder joint implant.

As shown in FIGS. 11A-11D, the frame 1110 can include an annular shaped body 1112 defining an aperture 1130, bone anchor pockets 1114a and 1114b (collectively 1114), snap-fit connector interfaces 1120a, 1120b, 1120c, and 1120d (collectively 1120), and locking screw pockets 1140a and 1140b (collectively 1140). Except as described below or as will be readily appreciated by a person skilled in the art, the frame 1110, the annular shaped frame body 1112, bone anchor pockets 1114, the snap-fit connector interfaces 1120, and the aperture 1130 are the same or substantially the same as the frame 110, annular shaped frame body 112, bone anchor pockets 114, the snap-fit connector interfaces 120, and the aperture 130 described above. Thus, a detailed description of the structure and function thereof is omitted here for the sake of brevity.

In some embodiments, the locking screw pockets 1140 can be cantilevered blocks configured to extend inward from opposing legs of the annular frame body 1112 such that the pockets are accessible through the frame aperture 1130. In some embodiments, the locking screw pockets 1140 can be aligned along a central horizontal axis A-A of the frame 1110. The locking screw pockets 1140 can define respective threaded holes 1142a and 1142b (collectively, 1142) configured to receive a corresponding locking screw (not shown). For example, as described in more detail with respect to FIGS. 14A-14C, the locking screw pockets 1140 can be used to attach a reverse glenoid component to the frame 1110, and thereby avoiding the need for a separate frame adaptor. Although two locking screw pockets 1140 are shown in the figures, more or less than two locking screw pockets (e.g., 1, 3, 4, 5, 6 or more locking screw pockets) can be included as part of the frame 1110.

As shown in FIGS. 12A-12D, the anatomic glenoid component 1150 can have a generally disc-shaped body that includes a proximal portion 1150p and a distal portion 1150d. The proximal portion 1150p can include a concave-shaped proximal-bearing surface 1152 and a distal-facing ridge 1154. The distal portion 1150d of the component 1150 can have a convex-shaped distal surface 1156 and a cylindrical-shaped post 1158 that projects substantially normal from the distal surface. Except as described below or as will be readily appreciated by a person skilled in the art, the anatomic glenoid component 1150, including but not limited to its proximal portion 1150p and distal portion 1150d, are the same or substantially the same as the anatomic glenoid component 150, including but not limited to its proximal portion 150p and distal portion 150d, described above. Thus, a detailed description of the structure and function thereof is omitted here for the sake of brevity.

The distal portion 1150d of the anatomic glenoid component 1150 can have a bespoke shape configured for insertion into the aperture 1130 of the frame 1110. For example, in the illustrated embodiment, the bespoke shape of the distal portion 1150d has a cross-sectional profile configured to generally form a negative of the cross-sectional profile of the frame aperture 1130. The distal portion 1150 can also define multiple recesses (or cut-away portions) 1150r configured to circumscribe (or at least partially circumscribe) the bone anchor pockets 1114 and the locking screw pockets 1140, and thus prevent the pockets from interfering during attachment of the glenoid component 1150 to the frame. As indicated above, the distal portion 1150d can have a generally convex-shaped distal bearing surface 1156 configured to mate directly with a substantially concave surface of glenoid bone in a patient's scapula and thus can maximize the contact surface area between the glenoid component 1150 and bone.

As discussed above, the frame 1110 can include multiple snap-fit connector interfaces 1120 for attaching the anatomic glenoid component 1150 to the frame. Referring to FIGS. 12A-12D, the anatomic glenoid component 1150 can include multiple snap-fit connectors 1157a, 1157b, 1157c, and 1157d (collectively 1157) configured to interlock or otherwise engage the corresponding snap-fit connector interfaces 1120a, 1120b, 1120c, and 1120d (collectively 1120) of the frame 1110. In the illustrated embodiment, each of the snap-fit connectors 1157 can be shaped like a hook or a clamp that projects distally from the ridge 1154 of the proximal portion 1150p of the glenoid component. In some embodiments, the snap-fit connectors 1157 can be configured to snap onto the frame 1110 at the location of the snap-fit connector interfaces 1120 defined in the annular frame body 1112. Persons skilled in the art will recognize that the snap-fit connectors 1157 can have alternative shapes and/or configurations for engaging the snap-fit connector interfaces 1120 when the anatomic glenoid component 1150 is pressed onto the frame 1110. Likewise, the disclosures more generally applicable to male interfaces (e.g., 157, 1157) and female interfaces (e.g., 120, 1120) provided for above with respect to the connectors 157 and interfaces 120 are applicable to the connectors 1157 and interfaces 1120.

Figure 13A:
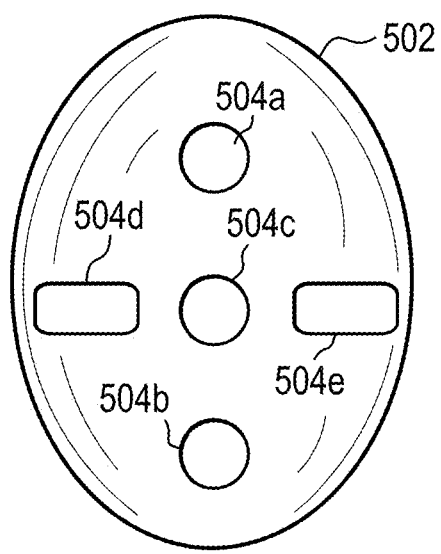
FIGS. 13A, 13B, and 13C are schematic illustrations of one exemplary embodiment of a method of deploying an anatomic shoulder joint implant into a patient, like the anatomic shoulder joint implant of FIG. 10A.
Figure 13B:
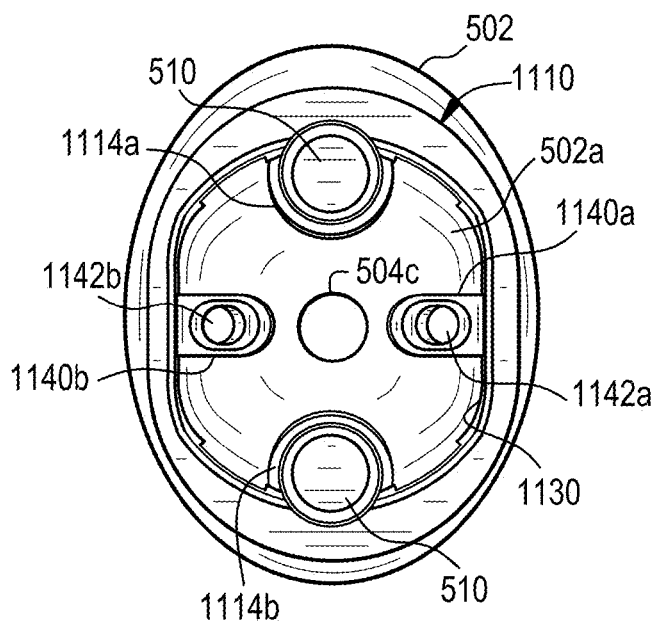
Figure 13C:
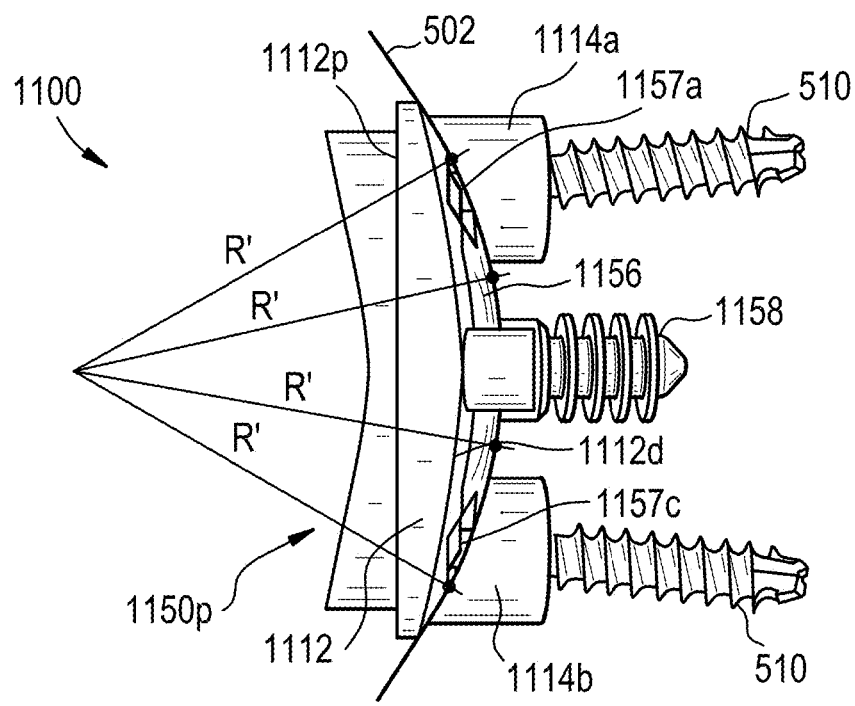

FIGS. 13A-13C are schematic illustrations of an exemplary embodiment of a method of deploying the anatomic shoulder joint implant 1100 in a patient's scapula. In the illustrated embodiment, the anatomic shoulder joint implant 1100 can be implanted as part of anatomic total shoulder joint arthroplasty procedure such that the implant 1100 is secured to glenoid bone of the patient's scapula to provide a corresponding concave bearing surface for a prosthetic head of a humeral prosthesis (e.g., 14 of FIG. 1A). Although the illustrated configuration uses the implant 1100 described above, at least some of the components associated with or otherwise used in conjunction with the implant 1100 may not be easily visible. In view of the disclosures provided for herein, and their related illustrations, a person skilled in the art will understand how the various components of the implant 1100 engage the various portions of the patient's anatomy, and/or the components of the implant 1100 and related tool(s) used in conjunction with the procedures disclosed with respect to FIGS. 13A-13C.

Referring to FIG. 13A, glenoid bone 502 of a patient's scapula can be reamed such that a surface of the glenoid bone 502 substantially conforms to the convex-shaped distal surfaces 1112d, 1156 of the frame 1110 and the anatomic glenoid component 1150, respectively. A person skilled in the art will recognize that a reamer (not shown) or other tool(s) can be used to prepare the glenoid bone 502 to have an approximately smooth, concave surface having the same, or substantially the same, radius of curvature as the convex surfaces of the frame 1110 and glenoid component 1150.

Further, as shown in FIG. 13A, one or more holes can be drilled into the glenoid bone 502 for receiving components of the implant 1100 that are configured to project distally into bone. As discussed above with respect to FIG. 5A, holes 504a and 504b can be drilled with a diameter to receive the bone anchor pockets 1114a and 1114b of the frame 1110 and a hole 504c can be drilled to receive the bone engaging post 1158 of the anatomic glenoid component 150. Additionally, in the illustrated embodiment, holes 504d and 504e can be drilled into bone for receiving the locking screw pockets 1140a and 1140b. A person skilled in the art will recognize a stop drill or other bone reaming tool(s) can be used to drill the holes into bone. In some embodiments, one or more guide plates (not shown) and/or other alignment tools can be used to drill the holes at the proper locations.

Referring to FIG. 13B, the frame 1110, which defines an aperture 1130, can be anchored to the glenoid bone 502. For example, in the illustrated embodiment, the frame 1110 can be mounted onto the glenoid bone 502 such that the four pockets (i.e., bone anchor pockets 1114 and locking screw pockets 1142) are inserted into the holes 504a, 504b, 504d, and 504e (not visible). After mounting the frame 1110 onto the glenoid bone 502, the frame can be anchored to bone by distally driving, or otherwise inserting, a poly-axial bone screw 510 or other bone anchor through each of the bone anchor pockets 1114. In some embodiments, a screw driver (not shown) can be used to drive the bone screws 510 into the glenoid bone. Once anchored to bone, the aperture 1130 of the frame 1110 exposes a concave-shaped portion 502a of the glenoid bone 502, including the drilled hole 504c'.

Referring to FIG. 13C, the anatomic glenoid component 1150 can be attached to the frame 1110 such that the distal portion 1150d of the glenoid component is in direct contact with the glenoid bone 502a through the frame aperture 130. For example, as shown, the convex-shaped distal surface 1156 and the post 1158 of the glenoid component 1150 can be in direct contact with the glenoid bone 502a through the frame aperture 1130. By configuring the convex-shaped distal surface 1156 of the glenoid component 1150 and the convex-shaped distal surface 1112d of the frame 1110 to have the same, or substantially the same, radius of curvature R', direct component-to-bone contact surface area can be maximized.

In some embodiments, the anatomic glenoid component 1150 can be attached to the frame 1110 by inserting the post 1158 into the drilled hole 504c' through the aperture 1130 and distally pressing the component through the aperture 1130 until it snaps onto the frame. For example, the anatomic glenoid component 1150 can snap onto the frame when the snap-fit connectors 1157 of the component (not visible) interlock with or otherwise engage the snap-fit connector interfaces 1120 (not visible) of the frame 1110. The post 1158 can be slightly oversized relative to the diameter of the drilled hole 504c', which can enable a press fit.

As described in more detail below, a reverse shoulder joint implant is provided for herein that can be configured to re-use the anchored frame 1110 of a previously deployed anatomic shoulder joint implant 1100 to facilitate anatomic-to-reverse conversions. For example, the locking screw pockets 1140 of the frame 1110 can be used to attach a reverse glenoid component to the frame, and thereby avoid the need for a separate frame adaptor.

Figure 14D:
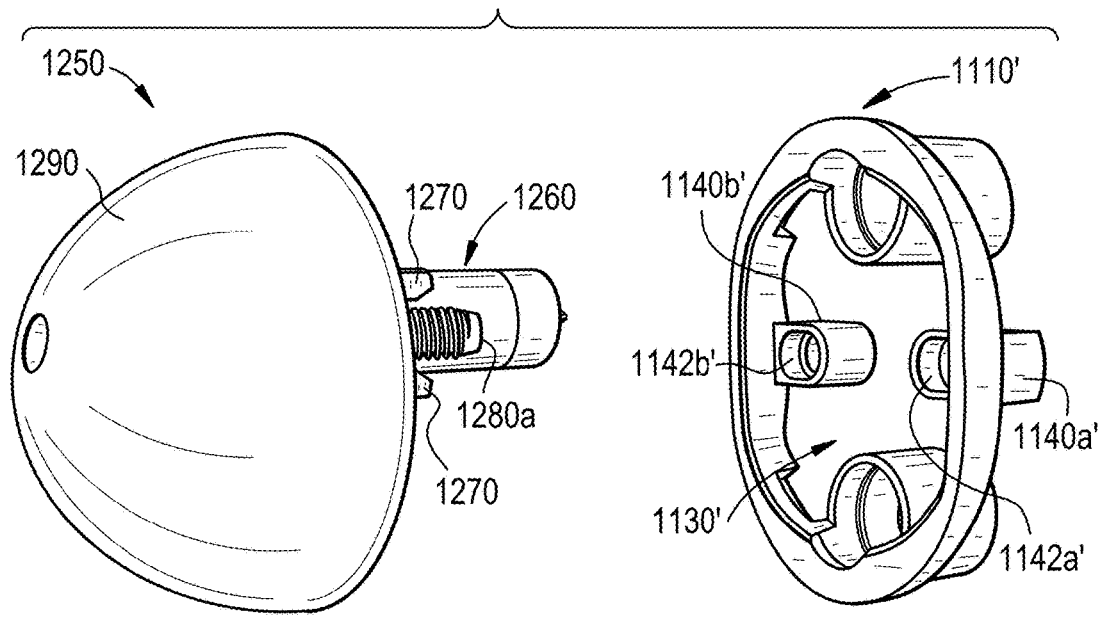
FIG. 14D is a perspective exploded view of components of the reverse shoulder joint implant of FIG. 14A, the components including the frame of FIG. 14A and a reverse glenoid component.

FIGS. 14A-14C illustrate an exemplary embodiment of a reverse shoulder joint implant 1200. The prosthetic implant 1200 can include a frame 1110' and a reverse glenoid component 1250. As shown, the reverse glenoid component 1250 can be attached directly to the frame 1110' by mounting the component on the frame and driving, or otherwise inserting, locking screws 1280a and 1280b (collectively 1280) distally through the component the threaded holes 1142a and 1142b (collectively, 1142) defined in the locking screw pockets 1140a' and 1140b' (collectively, 1140') of the frame.

As shown in the illustrated embodiment, the frame 1110' can include an annular shaped body 1112', bone anchor pockets 1114a' and 1114b' (collectively 1114'), snap-fit connector interfaces 1120a', 1120b', 1120c', and 1120d' (collectively 1120'), and locking screw pockets 1140'. Except as described below or as will be readily appreciated by a person skilled in the art, the frame 1110' is the same or substantially the same as the frame 1110 described above. Thus, a detailed description of the structure and function of the frame 1110' is omitted here for the sake of brevity.

Figure 15A:
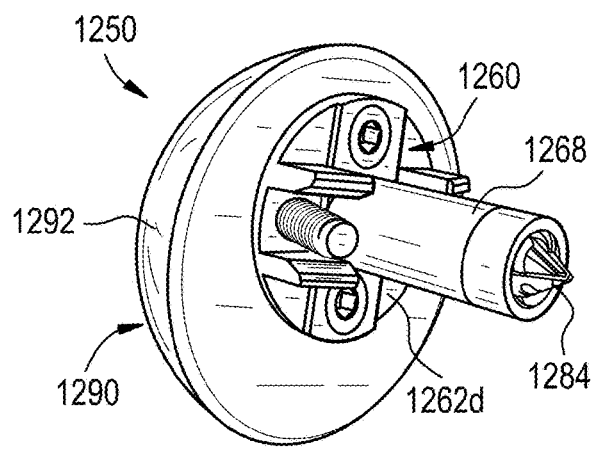
FIG. 15A is a rear perspective view of the reverse glenoid component of FIG. 14A.
Figure 15B:
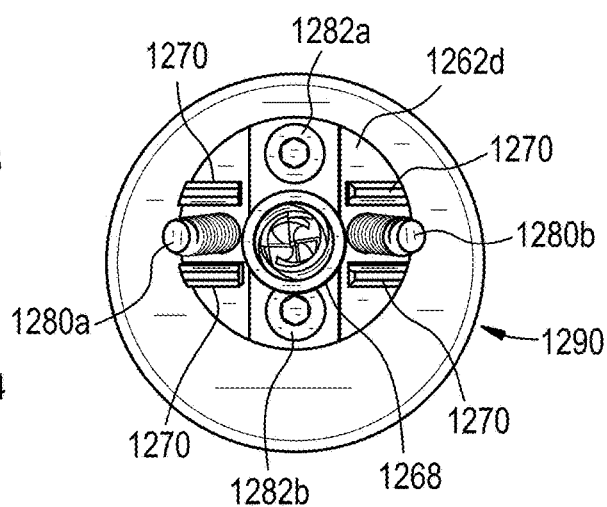
FIG. 15B is a rear view of the reverse glenoid component of FIG. 15A.
Figure 15C:
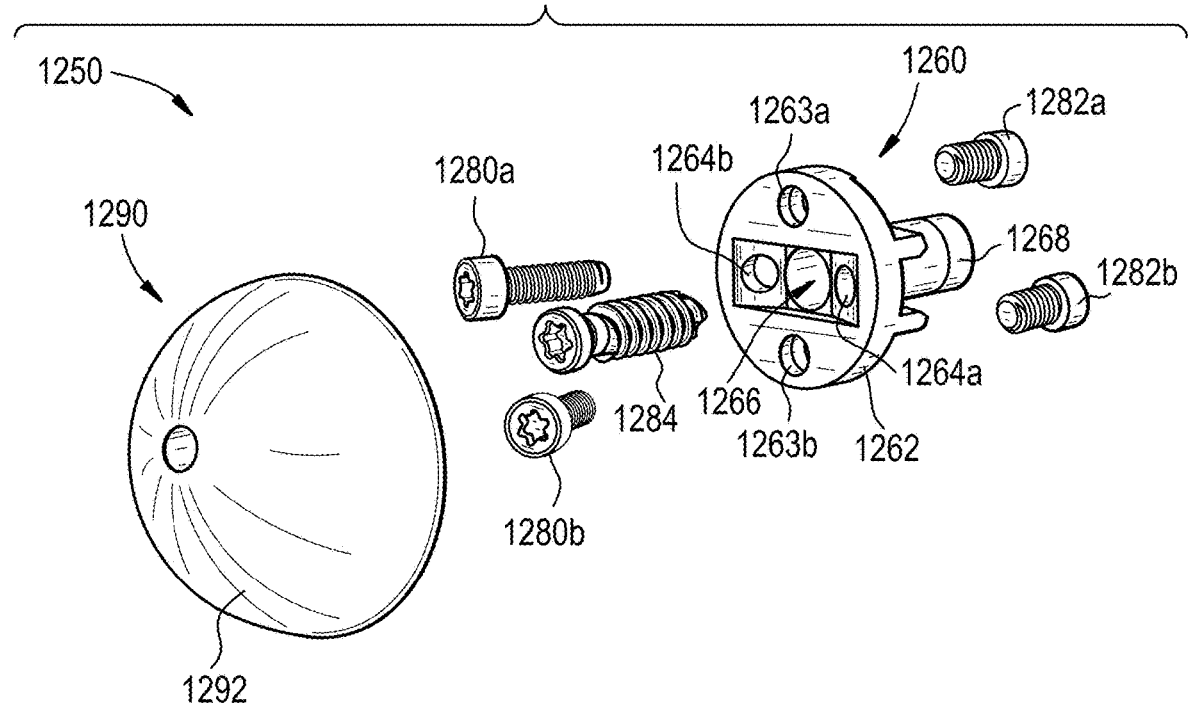
FIG. 15C is a perspective exploded view of components of the reverse glenoid component of FIG. 15A, the components including a glenosphere, a metaglene, a central bone screw, and a plurality of locking screws.

As shown in FIGS. 15A-15C, the reverse glenoid component 1250 can include a baseplate 1260, a prosthetic head 1290, frame locking screws 1280a and 1280b (collectively, 1280), glenosphere locking screws 1282a and 1282b (collectively, 1282), and a central bone screw 1284. In some embodiments, the constituent components 1260, 1290, 1280, 1282, and 1284 of the reverse glenoid component 1250 can be assembled prior to attachment to the frame 1110'.

The baseplate 1260, sometimes referred to herein as a "metaglene," can include a generally disc-shaped platform 1262 and a cylindrical-shaped post 1268 extending outward from the distal surface 1262*d* of the platform. Through holes 1264*a* and 1264*b* (collectively, 1264) can be defined in the metaglene platform 1262 to receive the locking screws 1280 for attaching the reverse glenoid component 1250 to the frame 1110'. The through holes 1264 can be threaded or unthreaded. The through holes 1264 can be oriented such that the locking screws 1280 can be driven, or otherwise inserted, into the locking screw pockets 1140' of the frame 1110' at a normal or oblique angle. In some embodiments, guide rails 1270 can project outward from the distal surface 1262*d* of the metaglene platform 1262. The guide rails 1270 can be configured to align the locking screws 1280 of the reverse glenoid component 1250 with the locking screw pockets 1140' of the frame 1110'.

In some embodiments, the cylindrical-shaped post 1268 can be configured to extend distally from the distal surface 1262*d* of the metaglene platform 1262. The metaglene post 1268 can be configured to be implanted into a hole or void formed in bone, e.g., glenoid bone of patient's scapula. In some embodiments, a central through hole 1266 can be defined to extend through the length of the metaglene platform 1262 and metaglene post 1268. Optionally, the central bone screw 1284 can be driven, or otherwise inserted, through the central hole 1266 and into glenoid bone, e.g., for providing additional anchoring support.

The prosthetic head 1290, sometimes referred to herein as a "glenosphere," can have a substantially hemispherical-shaped body 1292. To form the reverse glenoid component 1250, the glenosphere 1290 can be attached to the metaglene 1260 by driving, or otherwise inserting, the glenosphere locking screws 1282 proximally into glenosphere body 1292 via through holes 1263*a* and 1263*b* (collectively, 1263) defined in the metaglene platform 1262. As described in more detail below, the glenosphere body 1292 can define an open-ended cavity 1294 (see FIG. 16C) that can be configured to mate with the disc-shaped metaglene platform 1262. In some embodiments, the glenosphere 1290 and the metaglene 1260 can be configured to form a taper lock when the metaglene platform 1262 is received within the cavity 1294. Persons skilled in the art will recognize the glenosphere and the metaglene can be attached together using other techniques and/or mechanisms for securing one component with respect to another. As described in more detail below, the reverse glenoid component 1250, formed by the metaglene 1260 and the glenosphere 1290, can be attached to the frame 1110' by mounting the component onto the frame and driving, or otherwise inserting, the locking screws 1280 into the locking screw pockets 1140' of the frame. Further, A person skilled in the art, in view of the present disclosure, will understand the reverse glenoid component 1250 to be a prosthetic component as provided for herein, with the baseplate 1260 being part of, or coupled to, a distal-facing surface of the prosthetic component, and the hemispherical-shaped prosthetic head 1290 being part of, or coupled to, a proximal-bearing surface of the prosthetic component.

FIGS. 16A-16D are schematic illustrations of an exemplary embodiment of a method of deploying the reverse shoulder joint implant 1200 in a patient's scapula. In the illustrated embodiment, the reverse shoulder joint implant 1200 can be deployed as part of anatomic-to-reverse conversion of a total shoulder joint arthroplasty in which the anatomic glenoid component 1150 of the anatomic shoulder joint implant 1100 is removed and replaced with the reverse glenoid component 1250. Although the illustrated embodiment describes an anatomic-to-reverse conversion, a person skilled in the art will recognize that the reverse shoulder implant 1200 provided for herein can be deployed without having to previously deploy the anatomic glenoid implant.

Figure 16A:
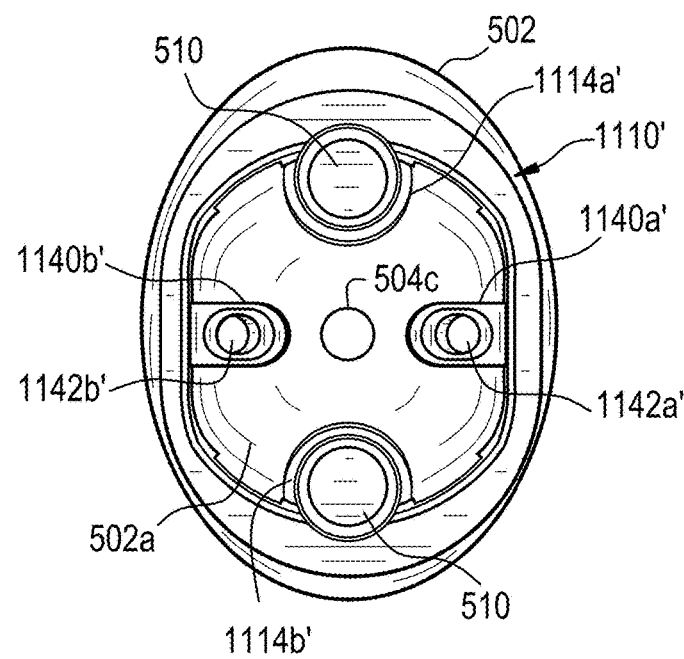
FIGS. 16A, 16B, and 16C are schematic illustrations of one exemplary embodiment of a method of deploying a reverse shoulder joint implant into a patient, like the reverse shoulder joint implant of FIG. 14A.

Referring to FIG. 16A, the frame 1110' is shown anchored to glenoid bone 502 and exposing a concave-shaped portion 502*a* of the glenoid bone, including a drilled hole 504*c'*. In the illustrated embodiment, the frame 1110' is anchored to bone by poly-axial bone screws 510 driven, or otherwise inserted, through the bone anchor pockets 1114*a'*, 1114*b'*. In the illustrated anatomic-to-reverse conversion, the anchored frame 1110' can be the same as the frame (e.g., 1110) previously deployed as part of an anatomic total shoulder arthroplasty described above with respect to FIGS. 11A-11D. An anatomic glenoid component 1150 (not shown) of a previously deployed anatomic glenoid implant can be removed in a prior processing step.

Figure 16B:
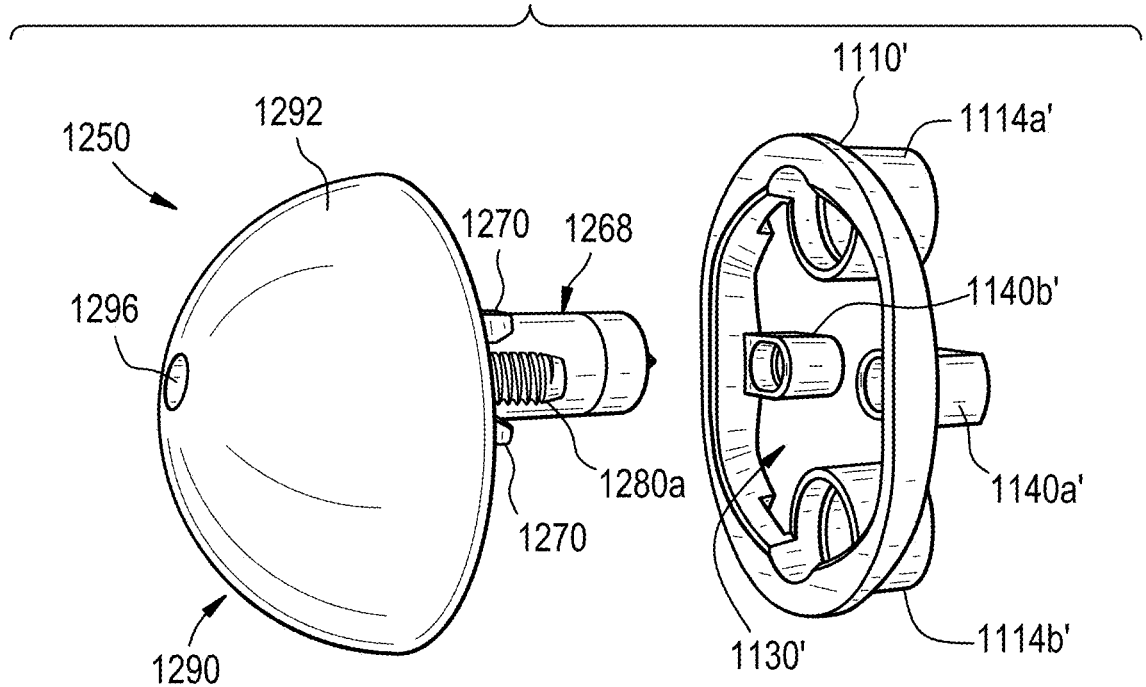

Referring to FIG. 16B, the assembled reverse glenoid component 1250 can be mounted on the frame 1110' such that the post 1268 is inserted distally through the frame aperture 1130' and into the drilled hole 504*c* in the glenoid bone 502*a* (not visible). The reverse glenoid component can be manipulated such that the frame locking screws 1280*a* and 1280*b* that project from the distal surface 1262*d* of the metaglene platform 1262*d* are aligned with the locking screw pockets 1140*a'* and 1140*b'* of the frame 1110'. In some embodiments, the locking screws 1280 can be aligned with the locking screw pockets 1140 by rotating the reverse glenoid component until the pockets are positioned between the guide rails 1290, e.g., as shown in FIG. 14C.

Figure 16C:
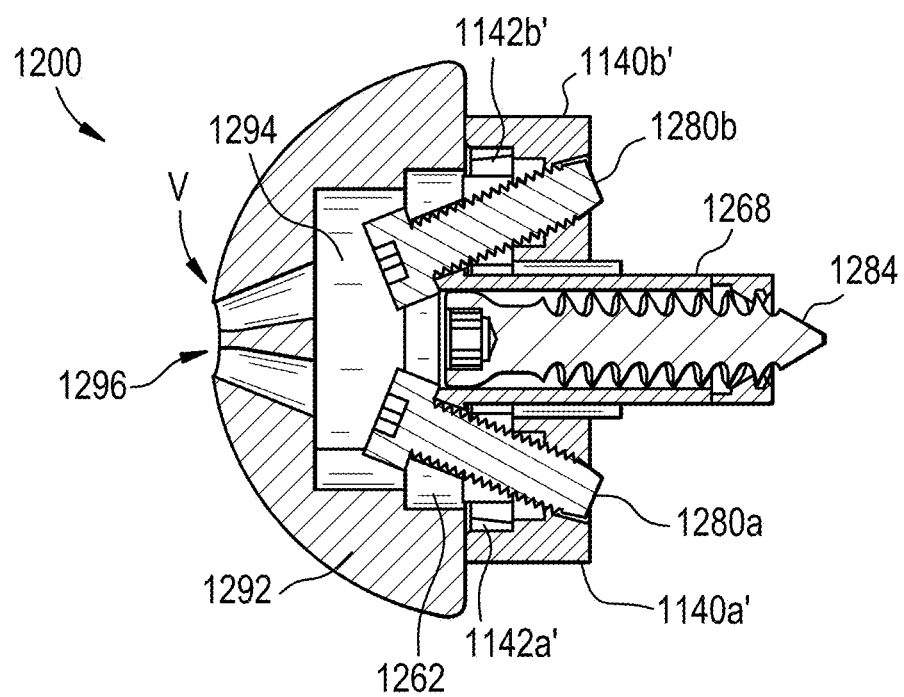
Figure 17A:
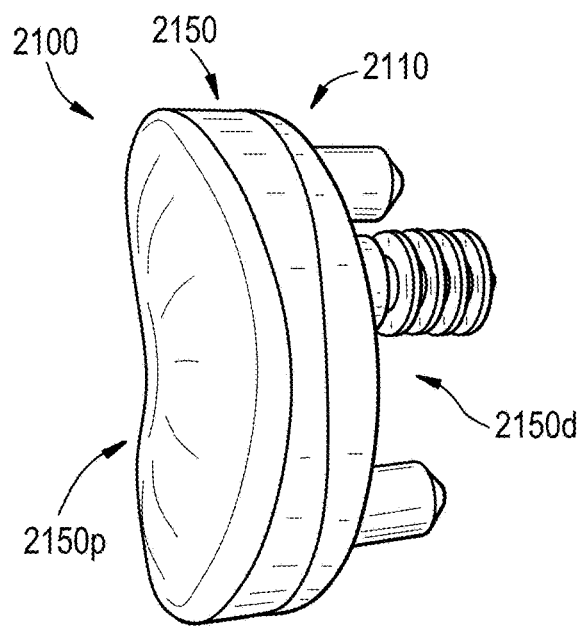
FIG. 17A is front perspective view of yet another exemplary embodiment of an anatomic shoulder joint implant.
Figure 17B:
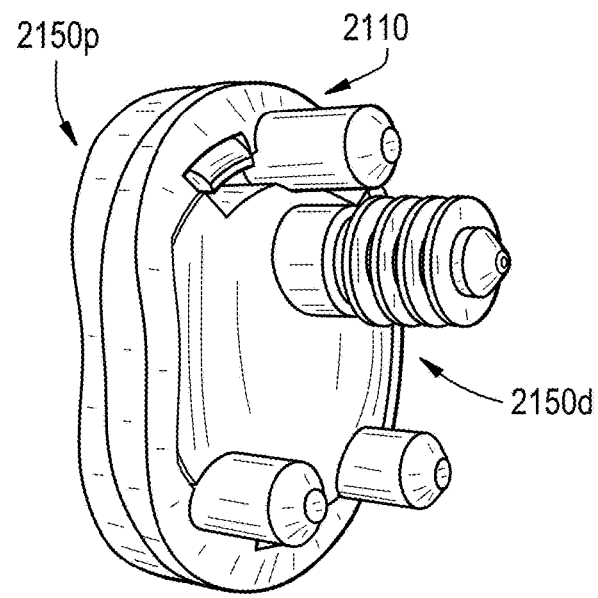
FIG. 17B is rear perspective view of the anatomic shoulder joint implant of FIG. 17A.
Figure 17C:
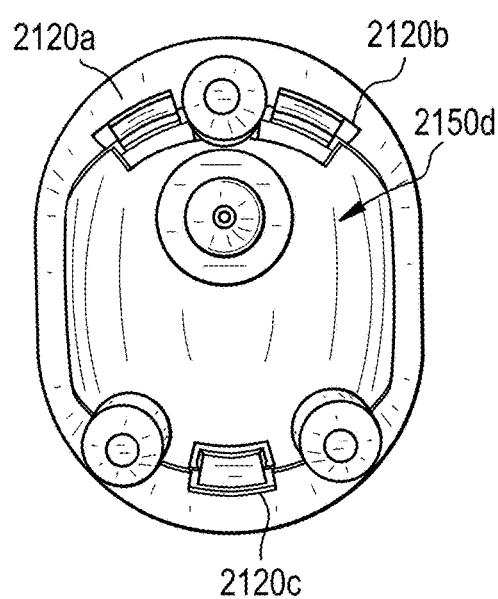
FIG. 17C is rear view of the anatomic shoulder joint implant of FIG. 17A.
Figure 17D:
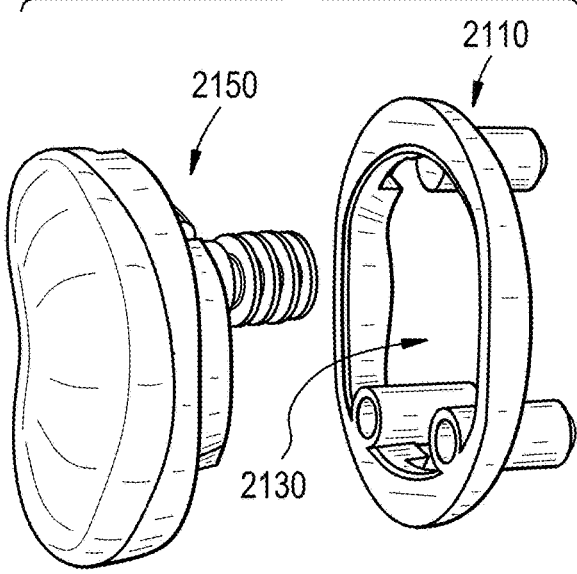
FIG. 17D is a perspective exploded view of components of the anatomic shoulder joint implant of FIG. 17A, the components including an anatomic glenoid component and a frame.
Figure 18A:
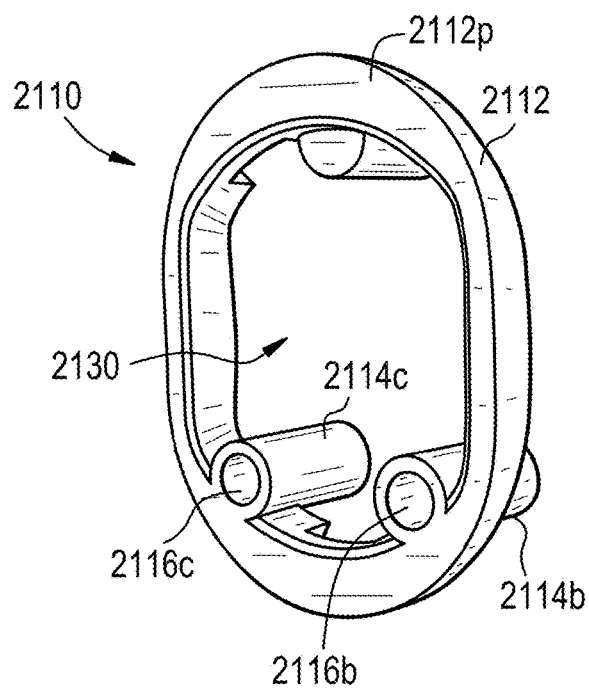
FIG. 18A is a front perspective view of the frame of FIG. 17C.
Figure 18B:
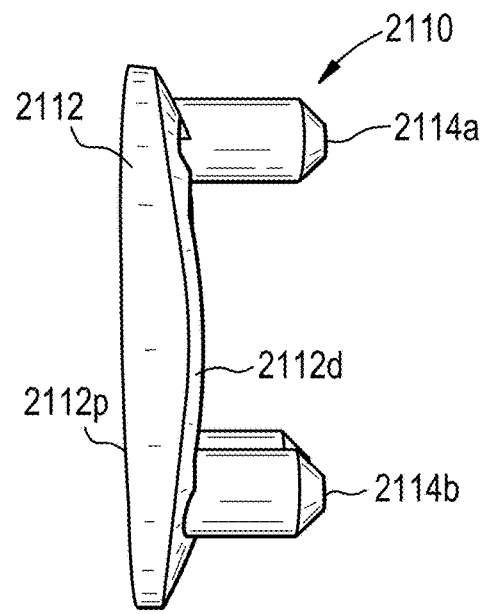
FIG. 18B is a side view of the frame of FIG. 18A.
Figure 18C:
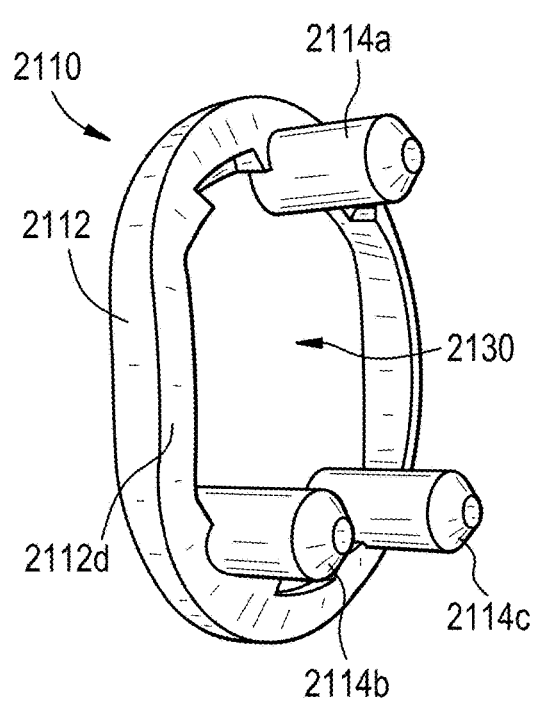
FIG. 18C is a rear perspective view of the frame of FIG. 18A.
Figure 18D:
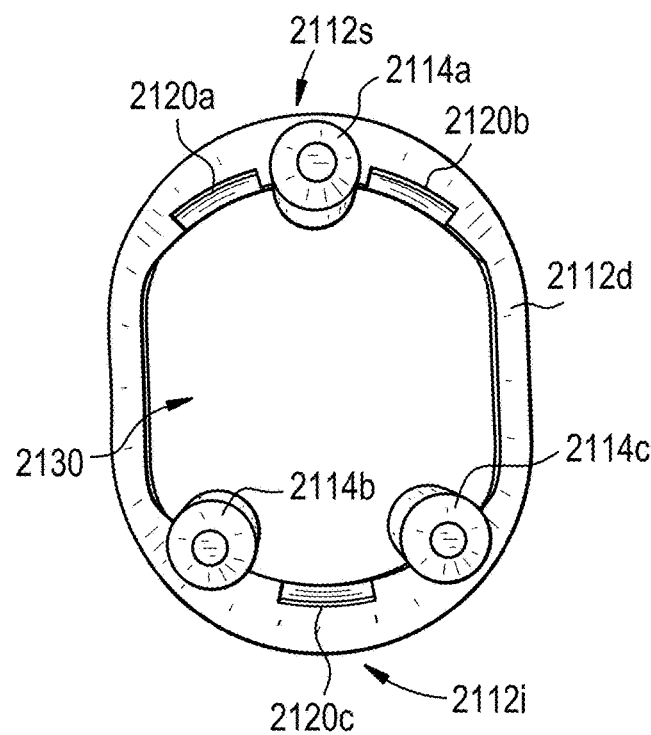
FIG. 18D is a rear view of the frame of FIG. 18A.

Referring to FIG. 16C, the reverse glenoid component 1250 can be secured to the frame 1110' by driving, or otherwise inserting, the frame locking screws 1280 into the threaded holes 1142 defined in the locking screw pockets 1140. In some embodiments, the locking screws 1280 can be accessed through an opening or port 1296 defined at a vertex V of the glenosphere body 1292. The port 1296 can be configured to lead to a cavity 1294 in which the respective heads of the locking screws 1280 can be exposed. For example, a screw driver (not shown) can be inserted through the port 1296 and into the cavity 1294 of the glenosphere body 1292 to drive the locking screws 1280 through the holes 1264 of the metaglene platform 1262 and into the locking screw pockets 1140' of the frame 1110'. Optionally, a screw driver can be inserted through the port 1296 and into the cavity 1294 of the glenosphere body 1292 to drive the central bone screw 1284 through the central hole 1266 of the metaglene 1260 and into glenoid bone, e.g., for providing additional anchoring support.

FIGS. 17A-17D illustrate yet another exemplary embodiment of an anatomic shoulder joint implant 2100. The prosthetic implant 2100 includes a frame 2110 and an anatomic glenoid component 2150. The frame 2110 can be anchored to bone and include multiple attachment interfaces 2120*a*, 2120*b*, and 2120*c* (collectively, 2120) for attaching the anatomic glenoid component 2150 to the frame. In addition, the frame 2110 can define an aperture 2130 through which a distal portion 2150*d* of the glenoid component 2150 can have direct contact with bone when attached to the frame. As described in more detail below, in some embodiments the frame 2110 can be configured to allow the shoulder joint implant 2100 to be converted to a reverse shoulder joint implant.

As shown in FIGS. 18A-18D, the frame 2110 can include an annular shaped body 2112 defining an aperture 2130, anchoring pegs 2114a, 2114b, 2114c (collectively 2114), and snap-fit connector interfaces 2120a, 2120b, and 2120c (collectively 2120). Except as described below or as will be readily appreciated by a person skilled in the art, the frame 2110, the annular shaped frame body 2112, the snap-fit connector interfaces 2120, and the aperture 2130 are the same or substantially the same as the frame 110, annular shaped frame body 112, snap-fit connector interfaces 120, and aperture 130 described above. Thus, a detailed description of the structure and function thereof is omitted for the sake of brevity.

In the illustrated embodiment, the frame 2110 includes three pegs 2114a, 2114b, and 2114c (collectively 2114) configured to anchor the frame to bone. As described in more detail with respect to FIGS. 21A-21C, the anchoring pegs 2114 can also be used to convert the anatomic shoulder implant 1100 into a reverse shoulder implant. The anchoring pegs 2114 can have a substantially cylindrical shape that extends distally from the frame 2110. For example, as shown, the anchoring peg 2114a can be disposed at a superior end 2112s of the frame body 2112, and the anchoring pegs 2114b and 2114c can be disposed at an inferior end 2112i.

Although three bone anchoring pegs 2114 are shown, the frame can include more or less than three pegs for anchoring the frame to bone (e.g., 1, 2, 4, 5, 6 or more pegs). In some embodiments, the outer surface of the anchoring pegs 2114 and the distal surface 2112d of the frame 2110 can be coated with a material that enhances fixation to bone, such as GRIPTION®, a titanium-based material that is available from DePuy Synthes Products, Inc. having a principle place of business in Raynham, Mass. A person skilled in the art will recognize that other materials can be used to enhance fixation of the frame to bone, including but not limited to hydroxyapatite, POROCOAT®, or simply a highly-textured surface. Such materials can be used in conjunction with any of the disclosures provided for here in or otherwise derivable from the present disclosures.

One or more of the anchoring pegs 2114 can define a threaded bore that extends at least partially along the length of the peg. For example, in the illustrated embodiments, the anchoring pegs 2114b and 2114c respectively define threaded bores 2116b and 2116c (collectively 2116). As described in more detail with respect to FIGS. 21A-21C, the threaded bores 2116 of the anchoring pegs can be configured to receive locking screws for attaching another prosthetic component, e.g., a reverse glenoid component, to the frame 2110.

In some embodiments, the snap-fit connector interfaces 2120 can be defined in the distal surface 2112d of the frame 2110. For example, as shown in the illustrated embodiment, the snap-fit connector interfaces 2120a and 2120b can be defined at the superior end 2112s of the frame 2110 on adjacent sides of the anchoring peg 2114a, and the snap-fit connector interface 2120c can be defined at the inferior end 2112i of the frame between the anchoring pegs 2114b and 2114c. Although four snap-fit connector interfaces 2120 are shown, the frame can define more or less than four snap-fit connector interfaces for attaching the anatomic glenoid component 2150 to the frame (e.g., 1, 2, 3, 5, 6, 7, 8 or more snap-fit connector interfaces).

Figure 19A:
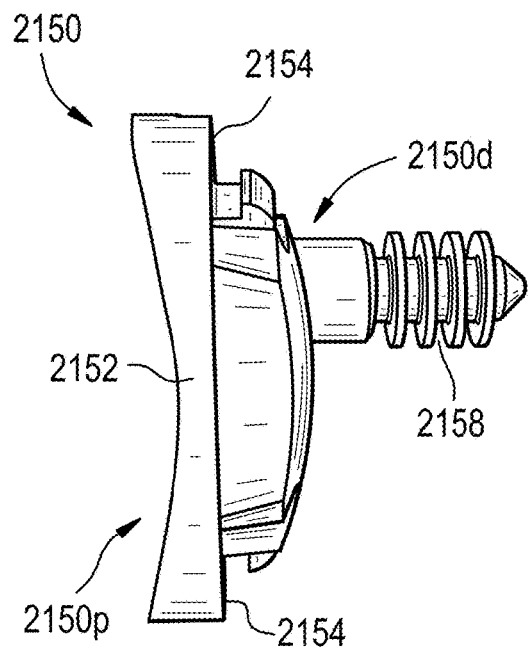
FIG. 19A is a side view of the anatomic glenoid component of FIG. 17C.
Figure 19B:
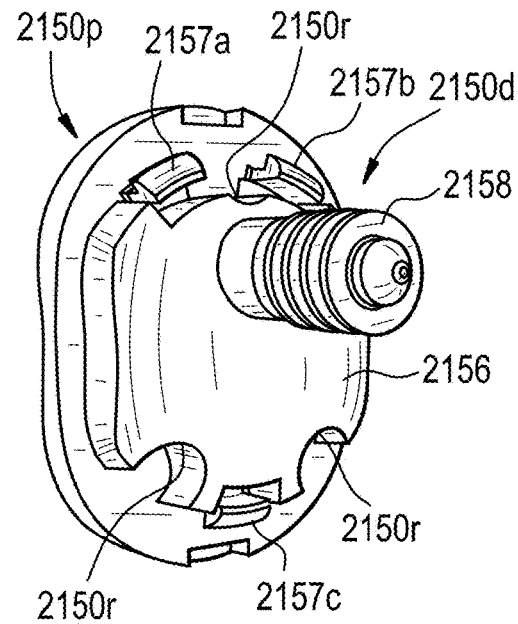
FIG. 19B is a rear perspective view of the anatomic glenoid component of FIG. 19A.
Figure 19C:
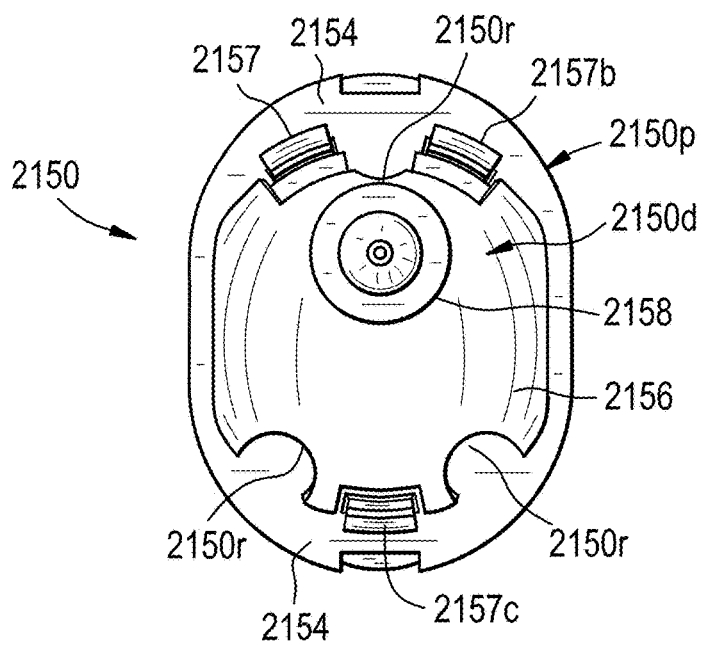
FIG. 19C is a rear view of the anatomic glenoid component of FIG. 19A.

As shown in FIGS. 19A-19C, the anatomic glenoid component 2150 can have a generally disc-shaped body that includes a proximal portion 2150p and a distal portion 2150d. The proximal portion 2150p can include a concave-shaped proximal-bearing surface 2152 and a distal-facing ridge 2154. The distal portion 2150d of the component 2150 can have a convex-shaped distal surface 2156 and a cylindrical-shaped post 2158 that projects substantially normal from the distal surface. Except as described below or as will be readily appreciated by a person skilled in the art, the anatomic glenoid component 2150, including but not limited to its proximal portion 2150p and distal portion 2150d, are the same or substantially the same as the anatomic glenoid component 150, including but not limited to its proximal portion 150p and distal portion 150d, described above. Thus, a detailed description of the structure and function thereof is omitted here for the sake of brevity.

The distal portion 2150d of the anatomic glenoid component 2150 can have a bespoke shape configured for insertion into the aperture 2130 of the frame 2110. For example, in the illustrated embodiment, the bespoke shape of the distal portion 2150d has a cross sectional profile configured to generally form a negative of the cross-sectional profile of the frame aperture 2130. The distal portion 2150 can also define multiple recesses (or cut-away portions) 2150r configured to at least partially circumscribe the anchoring pegs 2114, and thus prevent the pegs from interfering during attachment of the anatomic glenoid component 2150 to the frame. As indicated above, the distal portion 2150d can have a generally convex-shaped distal bearing surface 2156 configured to mate directly with a substantially concave surface of glenoid bone in a patient's scapula and thus can maximize the contact surface area between the glenoid component 2150 and bone.

As discussed above, the frame 2110 can include multiple snap-fit connector interfaces 2120 for attaching the anatomic glenoid component 2150 to the frame. In the illustrated embodiment, the anatomic glenoid component 2150 can include multiple snap-fit connectors 2157a, 2157b, and 2157c (collectively 2157) configured to interlock or otherwise engage the corresponding snap-fit connector interfaces 2120a, 2120b, and 2120c (collectively 2120) of the frame 2110. In the illustrated embodiment, each of the snap-fit connectors 2157 can be shaped like a hook or a clamp that projects distally from the ridge 2154 of the proximal portion 2150p of the glenoid component. In some embodiments, the snap-fit connectors 2157 can be configured to snap onto the frame 2110 at the location of the snap-fit connector interfaces 2120 defined in the annular frame body 2112. Persons skilled in the art will recognize that the snap-fit connectors 2157 can have alternative shapes and/or configurations for engaging the snap-fit connector interfaces 2120 when the anatomic glenoid component 2150 is pressed onto the frame 1110. Likewise, the disclosures more generally applicable to male interfaces (e.g., 157, 1157, 2157) and female interfaces (e.g., 120, 1120, 2120) provided for above with respect to the connectors 157 and interfaces 120 are applicable to the connectors 2157 and interfaces 2120.

Figure 20A:
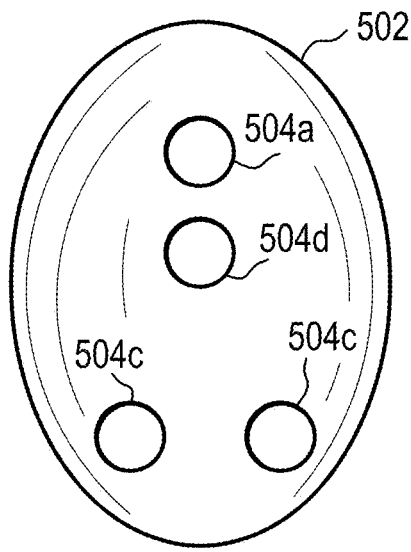
FIGS. 20A, 20B, and 20C are schematic illustrations of one exemplary embodiment of a method of deploying an anatomic shoulder joint implant into a patient, like the anatomic shoulder joint implant of FIG. 17A.
Figure 20B:
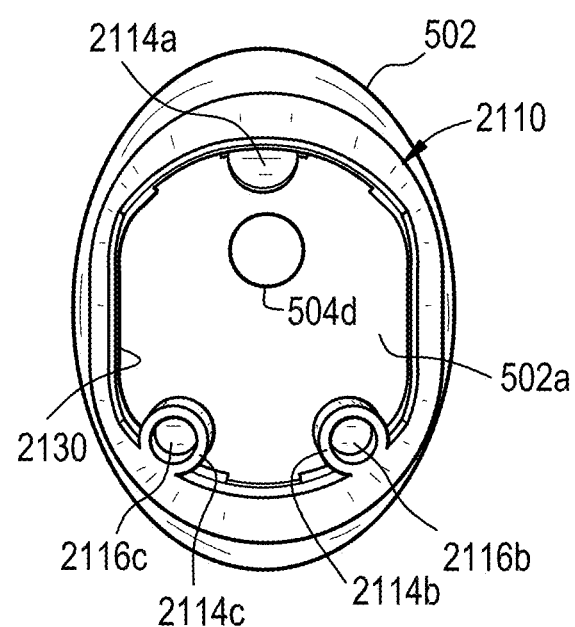
Figure 20C:
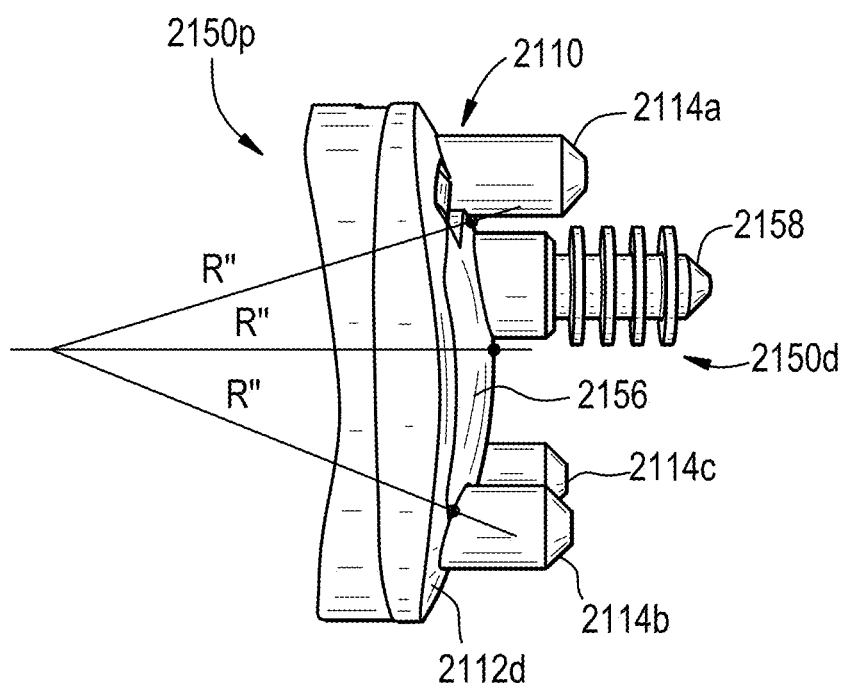

FIGS. 20A-20C are schematic illustrations of an exemplary embodiment of a method of deploying the anatomic shoulder joint implant 2100 in a patient's scapula. In the illustrated embodiment, the anatomic shoulder joint implant 2100 can be implanted as part of anatomic total shoulder joint arthroplasty procedure, such that the implant 2100 is secured to glenoid bone of the patient's scapula to provide a corresponding concave bearing surface for a prosthetic head of a humeral prosthesis (e.g., 14 of FIG. 1A). Although the illustrated configuration uses the implant 2100 described above, at least some of the components associated with or otherwise used in conjunction with the implant 2100 may not be easily visible. In view of the disclosures provided herein, and their related illustrations, a person skilled in the art will understand how the various components of the implant 2100 engage the various portions of the patient's anatomy, and/or the components of the implant 2100 and related tool(s) used in conjunction with the procedures disclosed with respect to FIGS. 20A-20C.

Referring to FIG. 20A, glenoid bone 502 of a patient's scapula can be reamed such that a surface of the glenoid bone 502 substantially conforms to the convex-shaped distal surface 2112d of the frame 2110 and the convex-shaped distal surface 2156 of the anatomic glenoid component 2150. A person skilled in the art will recognize that a reamer (not shown) or other tool(s) can be used to prepare the glenoid bone 502 to have an approximately smooth, concave surface having the same, or substantially the same, radius of curvature as the convex surfaces of the frame 2110 and glenoid component 2150.

Further, as shown in FIG. 20A, one or more holes can be drilled into the glenoid bone 502 for receiving components of the implant 2100 that are configured to project distally into bone. Holes 504a, 504b, and 504c can be drilled with a diameter to receive the bone anchoring pegs 2114a, 2114b, and 2114c of the frame 2110. Additionally, a hole 504d can be drilled to receive the bone engaging post 2158 of the anatomic glenoid component 2150. A person skilled in the art will recognize a stop drill or other bone reaming tool(s) can be used to drill the holes into bone. In some embodiments, one or more guide plates (not shown) and/or other alignment tools can be used to drill the holes at the proper locations.

Referring to FIG. 20B, the frame 2110, which defines an aperture 2130, can be anchored to the glenoid bone 502. For example, in the illustrated embodiment, the frame 2110 can be anchored onto the glenoid bone 502 by inserting the bone anchoring pegs 2114a, 2114b, and 2114c into the respective holes 504a, 504b, and 504c (not visible). The pegs 2114 can be slightly oversized relative to the diameter of the drilled hole 504a, 504b, and 504c, which can enable a press fit. Once the frame 2110 is anchored to bone, the aperture 2130 of the frame 2100 can expose a concave-shaped portion 502a of the glenoid bone 502, including the drilled hole 504d.

Referring to FIG. 20C, the anatomic glenoid component 2150 can be attached to the frame 2100 such that the distal portion 2150d of the component is in direct contact with the glenoid bone 502a through the frame aperture 2130. For example, as shown, the convex-shaped distal surface 2156 and the post 2158 of the glenoid component 2150 can be in direct contact with the glenoid bone 502a through the frame aperture 2130. By configuring the convex-shaped distal surface 2156 of the glenoid component 2150 and the convex-shaped distal surface 2112d of the frame 2110 to have the same, or substantially the same, radius of curvature R'', direct component-to-bone contact surface area can be maximized.

In some embodiments, the anatomic glenoid component 2150 can be attached to the frame 2110 by inserting the post 2158 into the drilled hole 504d through the frame aperture 2130 and distally pressing the component through the aperture until it snaps onto the frame. For example, the anatomic glenoid component 2150 can snap onto the frame when the snap-fit connectors 2157 of the component (not visible) interlock with or otherwise engage the snap-fit connector interfaces 2120 (not visible) of the frame 2110. The post 2158 can be slightly oversized relative to the diameter of the drilled hole 504d', which can enable a press fit.

Figure 21A:
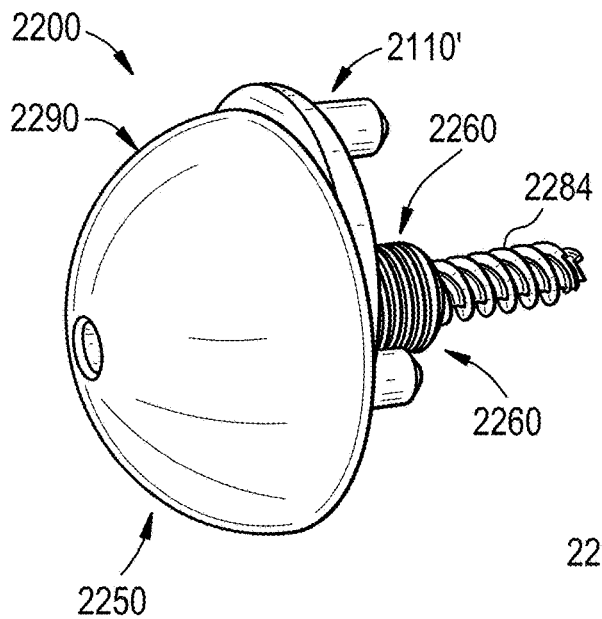
FIG. 21A is a front perspective view of one exemplary embodiment of a reverse shoulder joint implant, the implant including a frame similar to the frame of FIG. 18A.
Figure 21B:
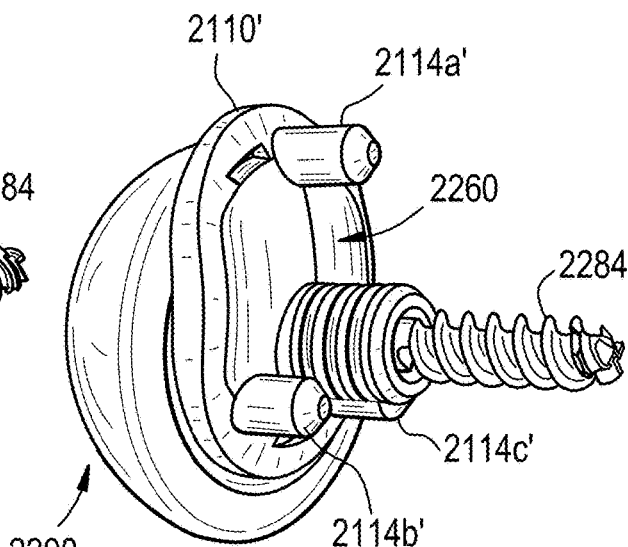
FIG. 21B is a rear perspective view of the reverse shoulder joint implant of FIG. 21A.
Figure 21C:
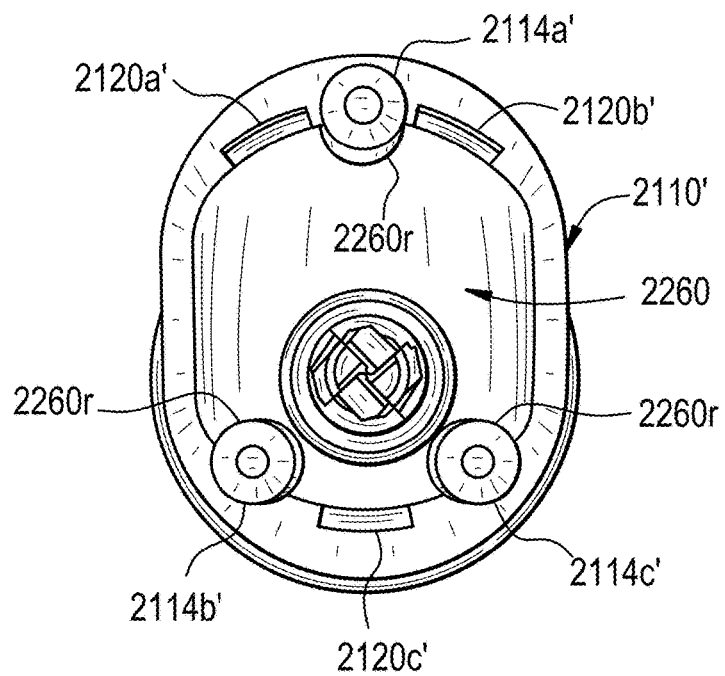
FIG. 21C is a rear view of the reverse shoulder joint implant of FIG. 21A.
Figure 21D:
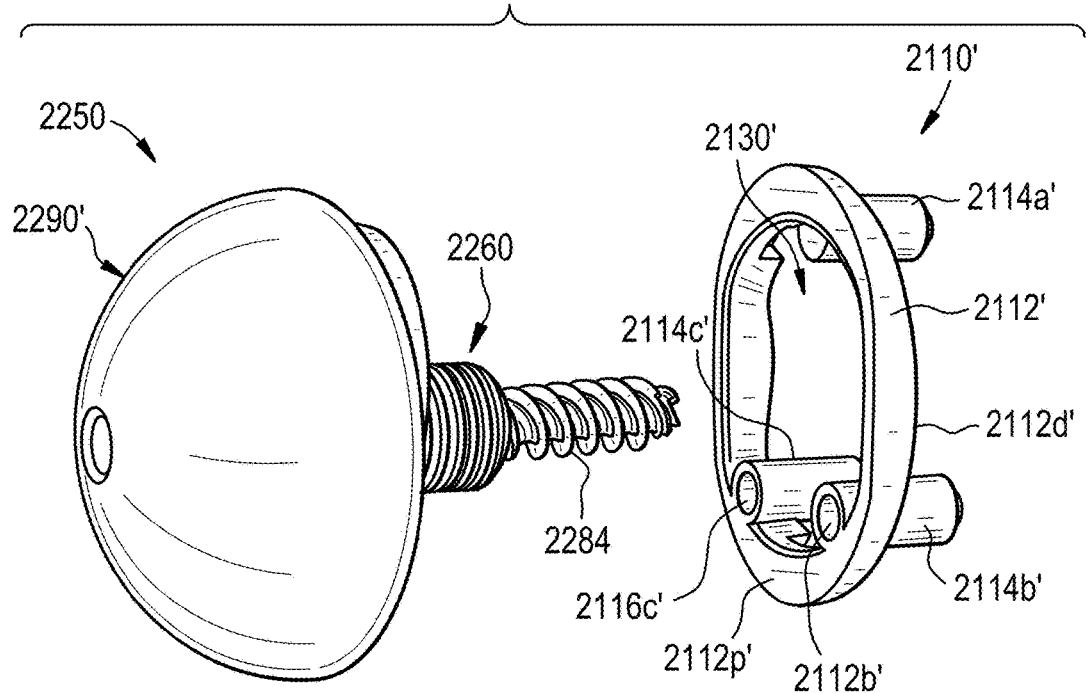
FIG. 21D is a perspective exploded view of components of the reverse shoulder joint implant of FIG. 21A, the components including the frame of FIG. 21A and a reverse glenoid component.
Figure 22A:
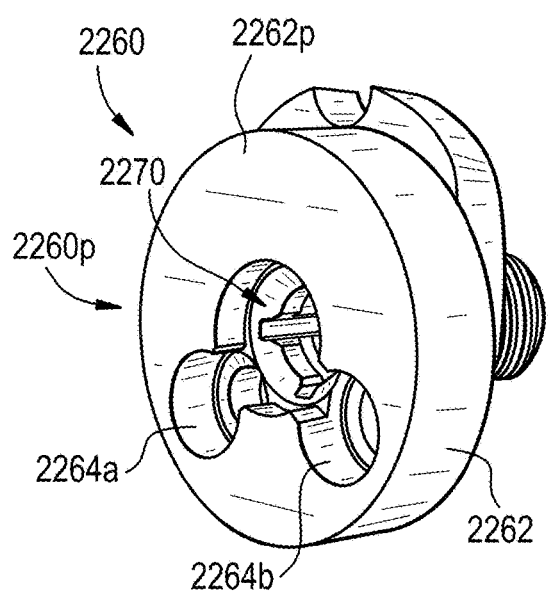
FIG. 22A is a front perspective view of a part of the reverse glenoid component of FIG. 21D, sometimes referred to herein as a metaglene.
Figure 22B:
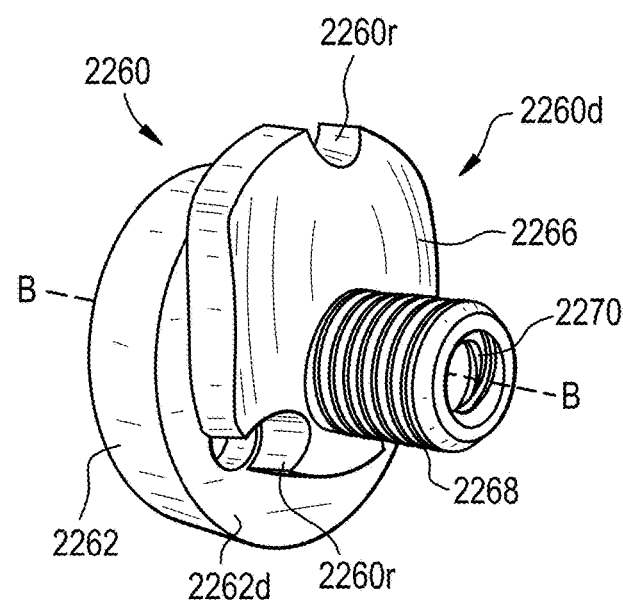
FIG. 22B is a rear perspective view of the metaglene of FIG. 22A.
Figure 22C:
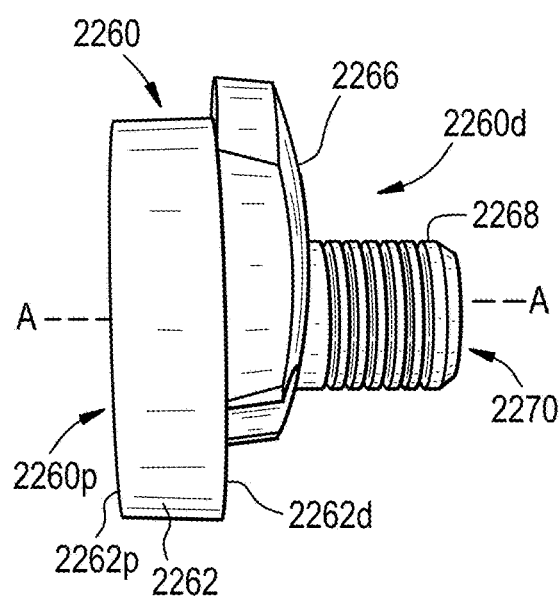
FIG. 22C is a side view of the metaglene of FIG. 22A.
Figure 22D:
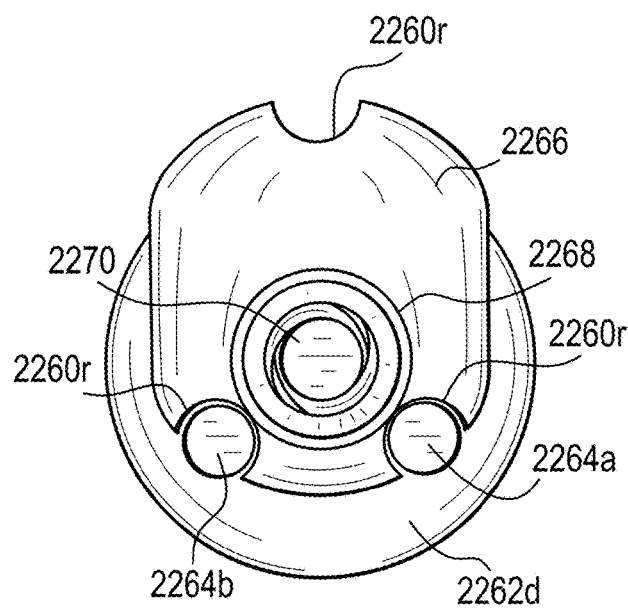
FIG. 22D is a rear view of the metaglene of FIG. 22A.

As described in more detail below with respect to FIGS. 21A-21C, a reverse shoulder joint implant can be configured to re-use the anchored frame 2110 of a previously deployed anatomic shoulder joint implant 2100 to facilitate anatomic-to-reverse conversions. For example, the threaded bores 2116 of one or more anchoring pegs 2114 of the frame 2110 can be can be used to attach a reverse glenoid component to the frame.

FIGS. 21A-21D illustrate an exemplary embodiment of a reverse shoulder joint implant 2200. The prosthetic implant 2200 can include a frame 2110' and a reverse glenoid component 2250. In the illustrated embodiment, the frame 2110' can include an annular shaped body 2112' defining an aperture 2130', anchoring pegs 2114a', 2114b', and 2114c' (collectively 2114'), and snap-fit connector interfaces 2120a', 2120b', and 2120c' (collectively 2120'). Except as described below, or as will be readily appreciated by a person skilled in the art, the frame 2110' is the same or substantially the same as the frame 2110 described above. Thus, a detailed description of the structure and function thereof is omitted for the sake of brevity.

In some embodiments, the reverse glenoid component 2250 can include a baseplate 2260 and a hemispherical-shaped prosthetic head 2290 coupled to the baseplate. A person skilled in the art, in view of the present disclosure, will understand the reverse glenoid component 2250 to be a prosthetic component as provided for herein, with the baseplate 2260 being part of, or coupled to, a distal-facing surface of the prosthetic component, and the hemispherical-shaped prosthetic head 2290 being part of, or coupled to, a proximal-bearing surface of the prosthetic component. As shown in FIGS. 22A-22D, the baseplate 2260, sometimes referred to herein as a "metaglene," can include a proximal portion 2260p and a distal portion 2260d. The proximal portion 2260p of the metaglene 2260 can include a generally disc-shaped platform 2262 having a proximal surface 2262p and a distal surface 2262d. The distal portion 2260d of the metaglene 2260 can have a bespoke shape configured for insertion into the aperture 2130' of the frame 2110'. In the illustrated embodiment, the proximal portion 2260p can be offset in an inferior direction from the distal portion 2260d such that the distal surface 2262d of the metaglene platform 2262 forms a ridge. Thus, the distal surface 2262d can bear against the proximal surface 2112p' of the frame 2110' when the metaglene 2260 is attached to the frame 2100'.

One or more through holes can be defined to extend through the proximal and distal surfaces 2262p and 2262d of the metaglene platform 2262. In the illustrated embodiment, a pair of through holes 2264a and 2264b (collectively 2264) are defined in the metaglene platform 2262 and configured to align with the threaded bores 2116b' and 2116c' defined in the anchoring pegs 2114b' and 2114b' when the metaglene 2260 is mounted on the frame 2110. Although two through holes 2262 are shown in the figures, more or less than two through holes can be defined in the metaglene platform 2262 (e.g., 1, 3, 4, 5, 6 or more through holes).

In some embodiments, the bespoke shape of the distal portion 2260d can have a cross-sectional profile configured to generally form a negative of the cross-sectional profile of the frame aperture 2130'. The distal portion 2260d can also define recesses (or cut-away portions) 2260r configured to circumscribe (or at least partially circumscribe) the anchoring pegs 2114' of the frame 2110' such that the pegs can be prevented from interfering during attachment of the metaglene 2260 to the frame. In some embodiments, the distal portion 2260d of metaglene 2260 can have a generally convex-shaped distal bearing surface 2266 configured to mate directly with a substantially concave surface of glenoid bone in a patient's scapula and thus can maximize the contact surface area between the metaglene 2260 and glenoid bone. One skilled in the art will recognize that the distal bearing surface 2266 of the metaglene 2260 can have a different shape or surface topology, depending, at least in part, on the opposing surface topology of the target bone. This goes for any of the bearing surfaces and complimentary surfaces thereof provided for in the present disclosure.

In some embodiments, the distal portion 2260d of metaglene 2260 can include a cylindrical-shaped post 2268. As shown in the illustrated embodiment, the post 2268 can be configured to project substantially normal to the distal surface 2266 of the metaglene 2260. The post 2268 can be inserted into a hole or void formed in bone, e.g., glenoid bone of a patient's scapula. In some embodiments, a through bore 2270 can be defined to extend through the metaglene 2260 along a central longitudinal axis B-B that extends through the post 2268. As shown in FIGS. 21A-21C, the central bore 2270 can be configured to receive a bone screw 2284, e.g., for anchoring the implant to bone. In other embodiments, the central bone screw can be omitted.

Figure 23A:
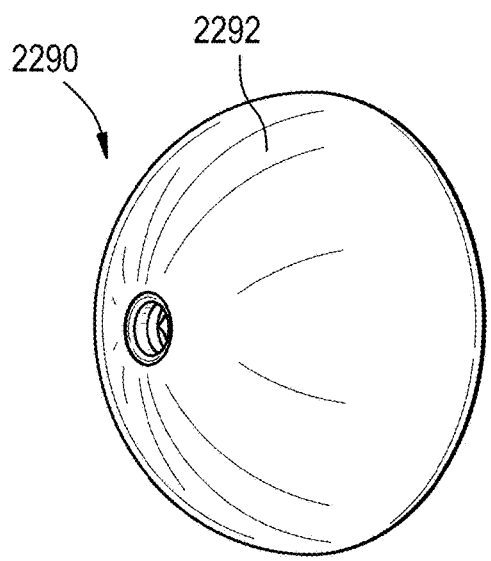
FIG. 23A is a front perspective view of another part of the reverse glenoid component of FIG. 21C, sometimes referred to herein as a glenosphere.
Figure 23B:
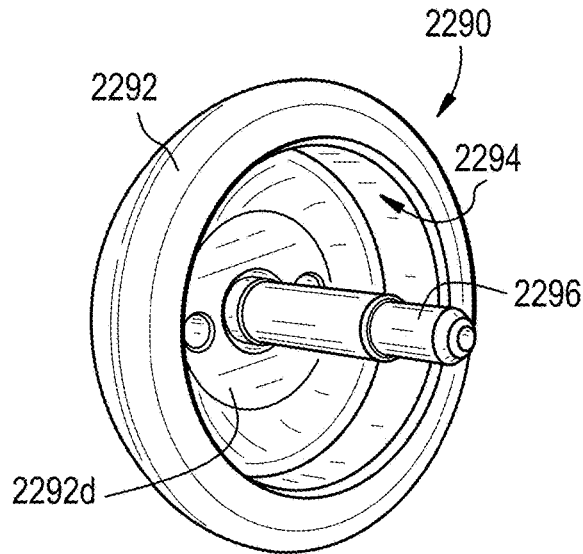
FIG. 23B is a rear perspective view of the glenosphere of FIG. 23A.

As shown in FIGS. 23A and 23B, the prosthetic head 2290, sometimes referred to herein as a "glenosphere," can have a substantially hemispherical-shaped body 2292. To attach the glenosphere 2290 to the metaglene 2260, the glenosphere body 2292 can define an open-ended cavity 2294 that can be configured to mate with the disc-shaped platform 2262 of the metaglene 2260. In some embodiments, the glenosphere 2290 and the metaglene platform 2262 can be configured to form a taper lock when the metaglene platform is received within the glenosphere cavity 2294.

Alternatively, or additionally, a coupling element 2296 can project distally from a distal-facing surface 2294d of the cavity 2294 of the glenosphere body 2292 for attaching the glenosphere 2290 to the metaglene 2260. As shown in the illustrated embodiment, the coupling element 2296 can be a threaded or unthreaded shaft configured to lock within the central through bore 2270 of the metaglene 2260. For example, in some embodiments, the glenosphere 2290 can be manipulated to screw or press-fit the coupling element 2296 into the through bore 2270 of the metaglene 2260. Persons skilled in the art will recognize the glenosphere and the metaglene can be attached together using other techniques and/or mechanisms for securing one component with respect to another.

FIGS. 24A-24D are schematic illustrations of an exemplary embodiment of a method of deploying the reverse shoulder joint implant 2200 in a patient's scapula. In the illustrated embodiment, the reverse shoulder joint implant 2200 can be deployed as part of anatomic-to-reverse conversion of a total shoulder joint arthroplasty in which the anatomic glenoid component of the anatomic shoulder joint implant 1100 is removed and replaced with the reverse glenoid component 1250. Although the illustrated embodiment describes an anatomic-to-reverse conversion, a person skilled in the art will recognize that the reverse shoulder implant 1200 provided for herein can be deployed without having to previously deploy the anatomic implant.

Figure 24A:
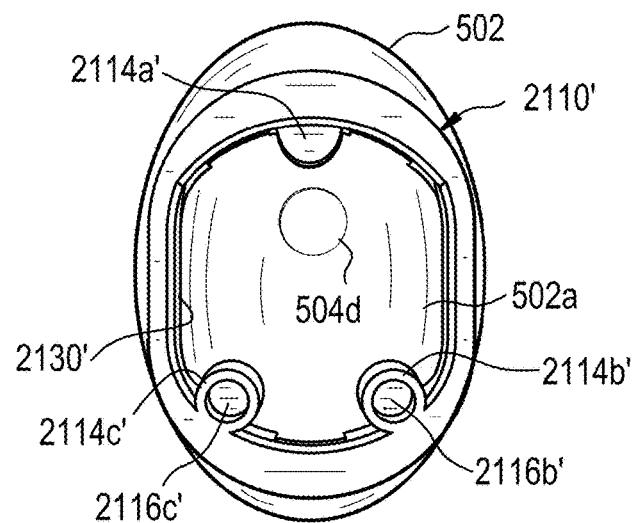
FIGS. 24A, 24B, 24C, and 24D are schematic illustrations of one exemplary embodiment of a method of deploying a reverse shoulder joint implant into a patient, like the reverse shoulder joint implant of FIG. 21A.

Referring to FIG. 24A, the frame 2110' is shown anchored to glenoid bone 502 and exposing a concave-shaped portion 502a of the glenoid bone, including a drilled hole 504d'. In the illustrated embodiment, the frame 2110' is anchored to bone by three anchoring pegs 2114a', 2114b', and 2114c'. As discussed above, the outer surface of the anchoring pegs 2114' and the distal surface 2112d' (not visible) of the frame 2110' can be coated with a material that enhances fixation to bone, such as GRIPTION®. In the illustrated anatomic-to-reverse conversion, the anchored frame 2110' can be the same frame (e.g., 2110) previously deployed as part of an anatomic total shoulder arthroplasty described above with respect to FIGS. 20A-20C. An anatomic glenoid component 2150 (not shown) of a previously deployed anatomic glenoid implant can be removed in a prior processing step.

Figure 24B:
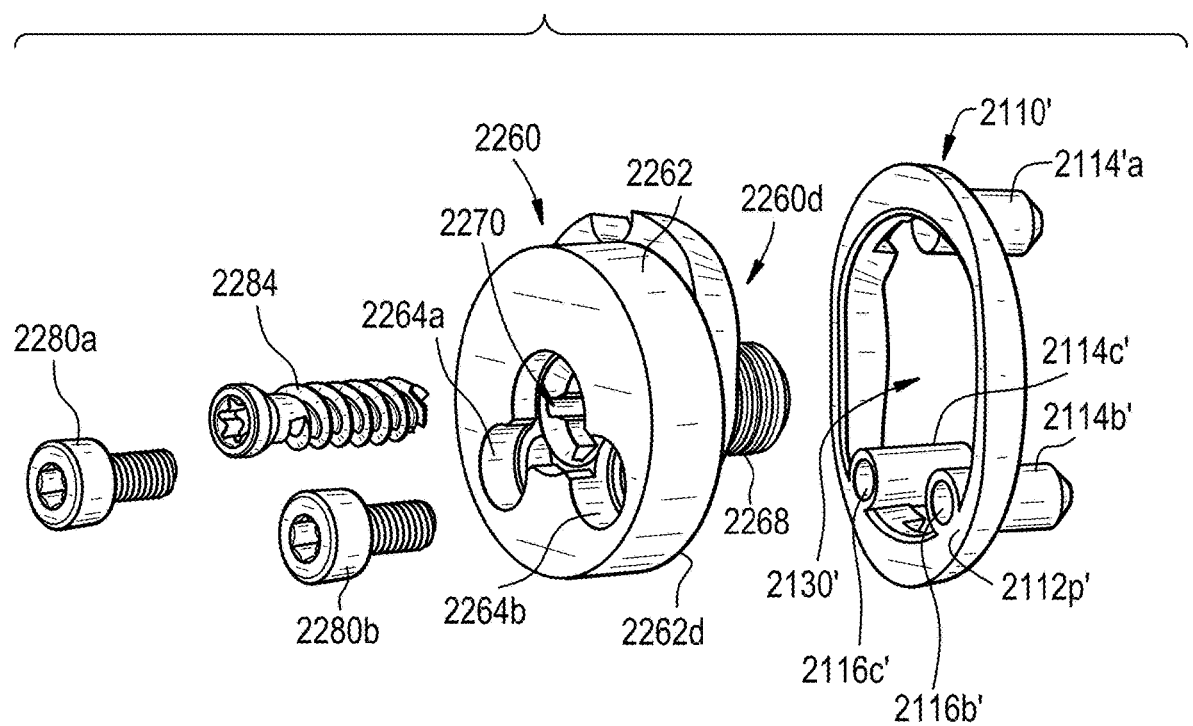

Referring FIG. 24B, the metaglene 2260 can be attached to the frame 2110'. To attach the metaglene 2260 to the frame 2110', the distal portion 2260d of the metaglene 2260 can be distally inserted through the frame aperture 2130' such that the post 2268 is inserted into the previously drilled hole 504d' (not visible). The metaglene 2260 can continue to be inserted distally until the distal surface 2262d of the metaglene platform 2262 bears against the proximal surface 2112p' of the frame 2110'. As the metaglene 2260 is inserted into the frame aperture 2130', the bespoke shape of its distal portion 2260d can serve as a key for aligning the through holes 2264 of the metaglene platform 2262 with the threaded bores 2116' of the anchoring pegs 2114'. To secure the metaglene 2260 to the frame 2110', locking screws 2280a and 2280b (collectively 2280) can be driven, or otherwise inserted, distally into the through holes 2264 of the metaglene 2260 and into the threaded bores 2116' of the respective anchoring pegs 2114'. Optionally, a bone screw 2284 can be driven, or otherwise inserted, distally through the central through bore 2270 of the metaglene 1260 and into bone.

Figure 24C:
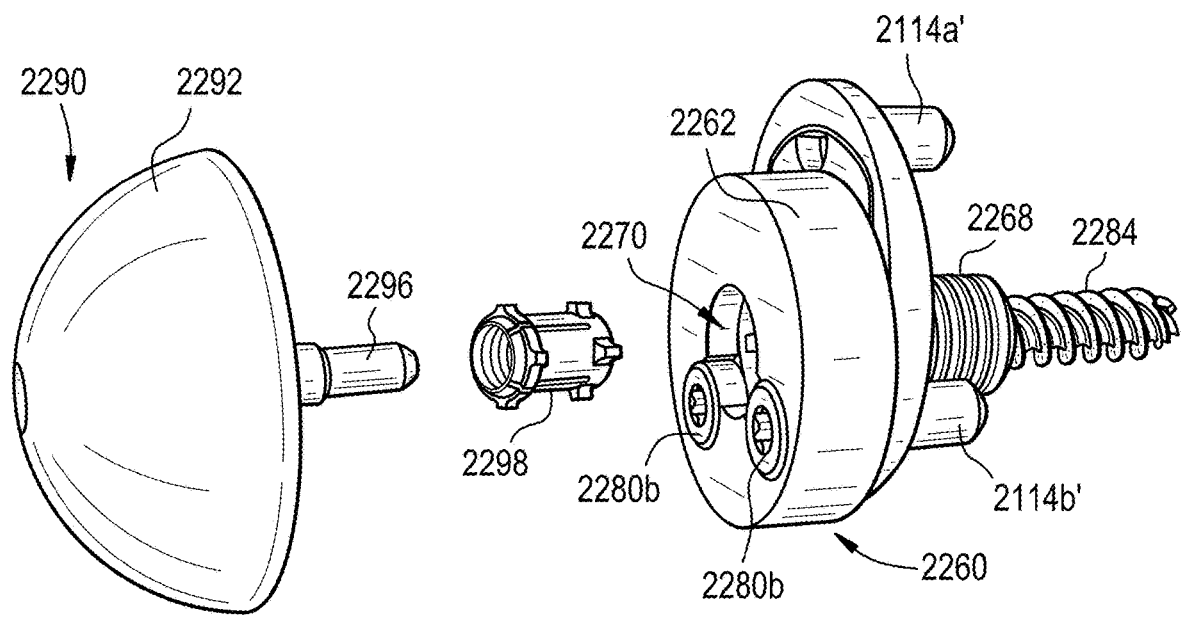

Referring to FIG. 24C, the glenosphere 2290 can be attached to the metaglene 2260. For example, in some embodiments, a coupling element 2296 of the glenosphere body 2292 can be screwed or press fit into a central bore 2270 of the metaglene 2260. Additionally, or alternatively, the glenosphere 2290 and the metaglene 2260 can form a taper lock when the disc-shaped metaglene platform 2262 is received within a cavity 2294 (not visible) defined in the glenosphere body 2292.

In some embodiments, a removable collet 2298 can be disposed within the central through bore 2270 of the metaglene 2260. The collet 2298 can be dimensioned to engage the coupling element 2296 of the glenosphere 2290 when the diameter of the coupling element is less than a diameter of the central through bore 2270. For example, in some embodiments the collet 2298 can be inserted to reduce the diameter of the central through bore 2270 of the metaglene 2260 after distally driving, or otherwise inserting, a bone screw 2284 that has a larger maximum diameter than the coupling element 2296 through the bore 2270 into bone 502a. In some embodiments, the collet 2298 can be implemented as shown and described in U.S. patent application Ser. No. 16/044,473, filed on Jul. 24, 2018, entitled "BASEPLATE OF A MODULAR SHOULDER JOINT PROSTHESIS AND RELATED METHODS FOR IMPLANTING THE SAME," the contents of which is incorporated herein by reference in its entirety.

Figure 24D:
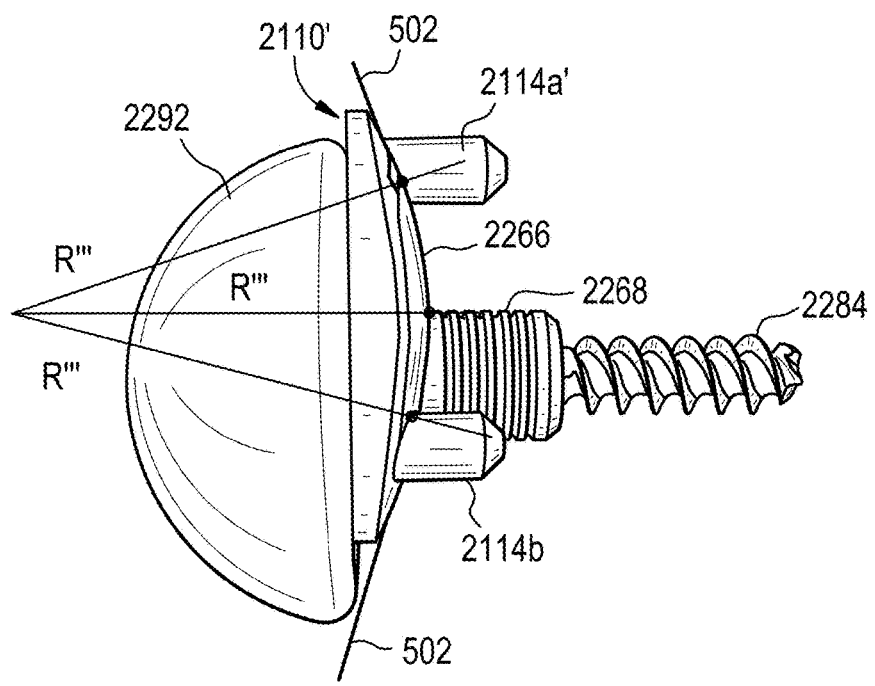

As shown in FIG. 24D, when attachment of the reverse glenoid component 2250 to the frame 2110' is completed, the distal portion 2260d of the metaglene 2260 can be in direct contact with the glenoid bone 502a through the frame aperture 2130'. For example, in the illustrated embodiment, the convex-shaped distal surface 2266 and the post 2268 of the metaglene 2260 can be in direct contact with the glenoid bone 502a through the frame aperture 2130. By configuring the convex-shaped distal surface 2266 of the metaglene 2260 and the convex-shaped distal surface 2112d of the frame 2110' to have the same, or substantially the same, radius of curvature R''', direct component-to-bone contact surface area can be maximized.

Figure 25A:
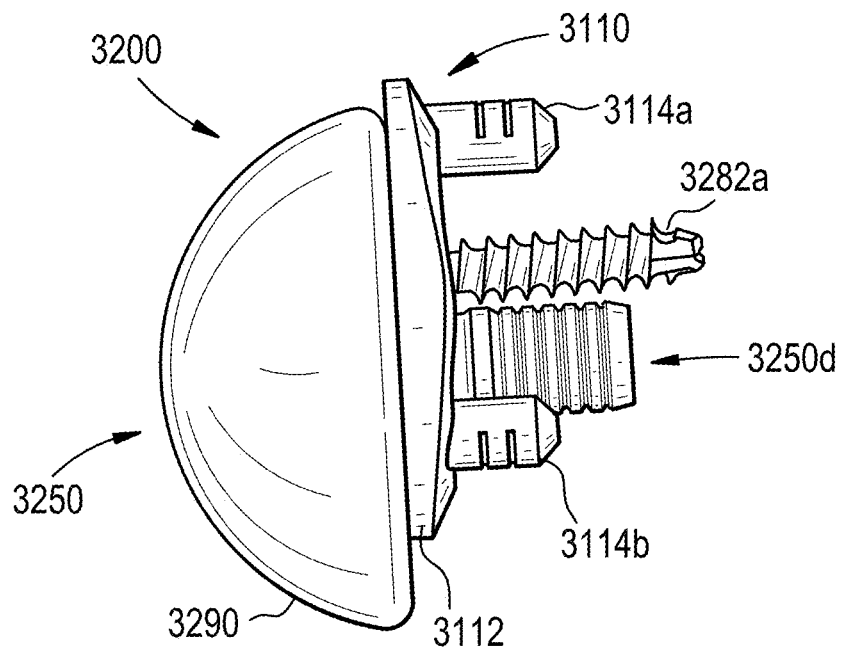
FIG. 25A is side view of yet another exemplary embodiment of a reverse shoulder joint implant.
Figure 25B:
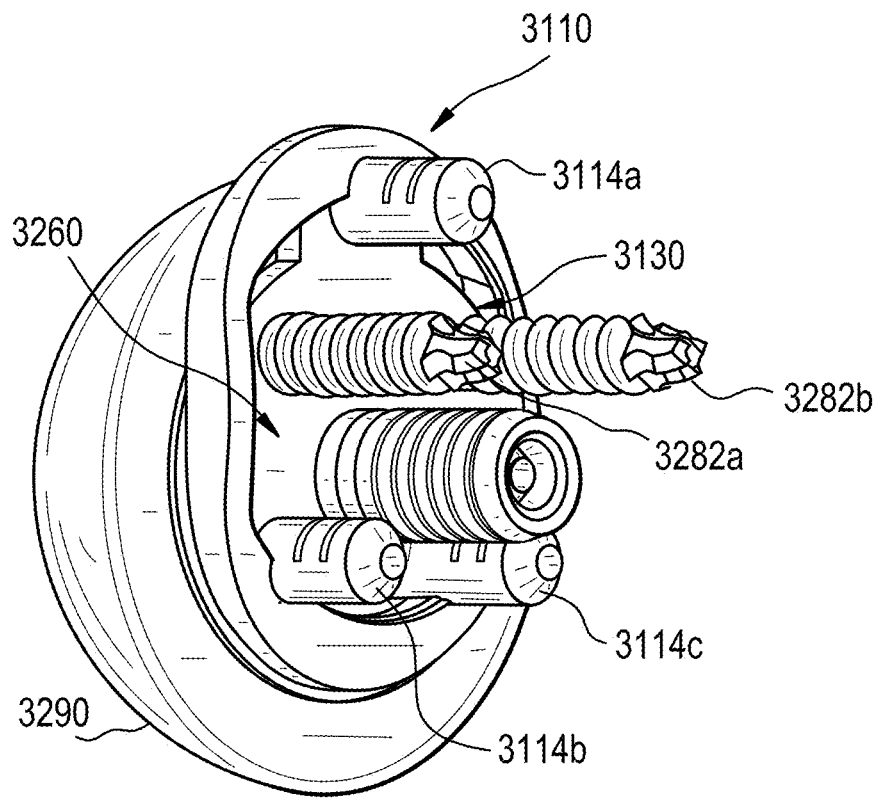
FIG. 25B is rear perspective view of the reverse shoulder joint implant of FIG. 25A.

FIGS. 25A and 25B illustrate another exemplary embodiment of a reverse shoulder joint implant 3200. The prosthetic implant 3200 can include a frame 3110 and a reverse glenoid component 3250. The frame 3110 can define an aperture 3130 through which a distal portion 3250d of the reverse glenoid component 3250 can have direct contact with bone when attached to the frame. In some embodiments, the reverse glenoid component 3250 can include a baseplate 3260 and a hemispherical-shaped prosthetic 3290 coupled to the baseplate. Optionally, peripheral bone screws 3282a and 3282b (collectively, 3282) can be driven, or otherwise inserted, through the baseplate 3260 to further anchor the implant 3200 to bone.

Except as described below or as will be readily appreciated by a person skilled in the art, the frame 3110 can be the same, or substantially the same, as the frame 2110 described above. For example, in the illustrated embodiment, the frame 3110 can include an annular shaped body 3112 defining an aperture 3130, and anchoring pegs 3114a, 3114b, and 3114c (collectively 3114). Thus, a detailed description of the structure and function of the frame 3110 is omitted here for the sake of brevity.

Figure 26:
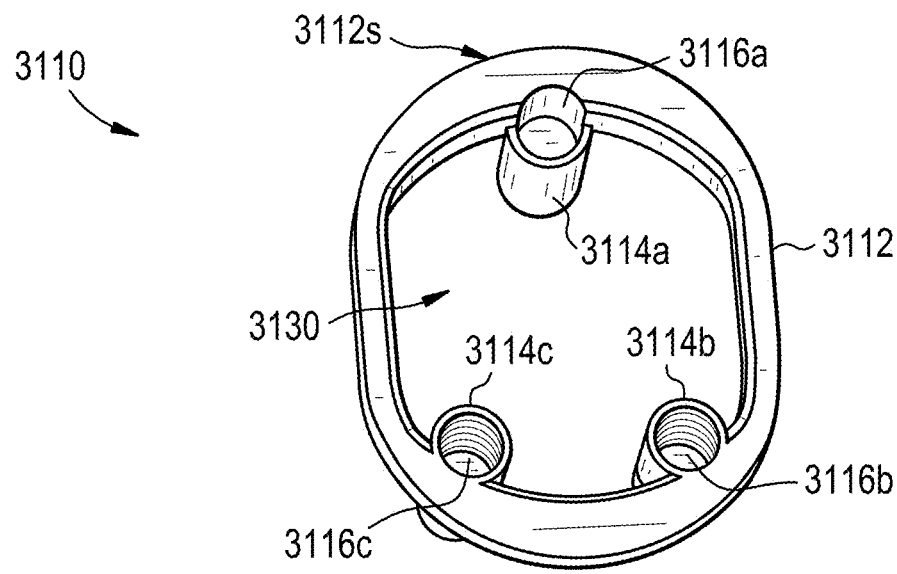
FIG. 26 is a front perspective view of a frame included in the reverse shoulder joint implant of FIG. 25A.

As shown in FIG. 26, each of the anchoring pegs 3114 of the frame 3110 can have a substantially cylindrical shape and extend distally from the frame. For example, in the illustrated embodiment, the anchoring peg 3114a can be disposed at a superior end 3112s of the frame body 3112 and the anchoring pegs 3114b and 3114c can be disposed at an inferior end 3112i. Each of the anchoring pegs 3114a, 3114b, and 3114c can define a corresponding bore 3116a, 3116b, and 3116c (collectively 3116) that extends at least partially along the length of the peg. The bores 3116 defined within the anchoring pegs 3114 can be threaded or unthreaded. By way of non-limiting example, in the illustrated embodiment, the bore 3116a of the anchoring peg 3114a can be an unthreaded bore, and the bores 3116b and 3116c of the respective anchoring pegs 3114b and 3114c can be threaded bores.

Figure 27:
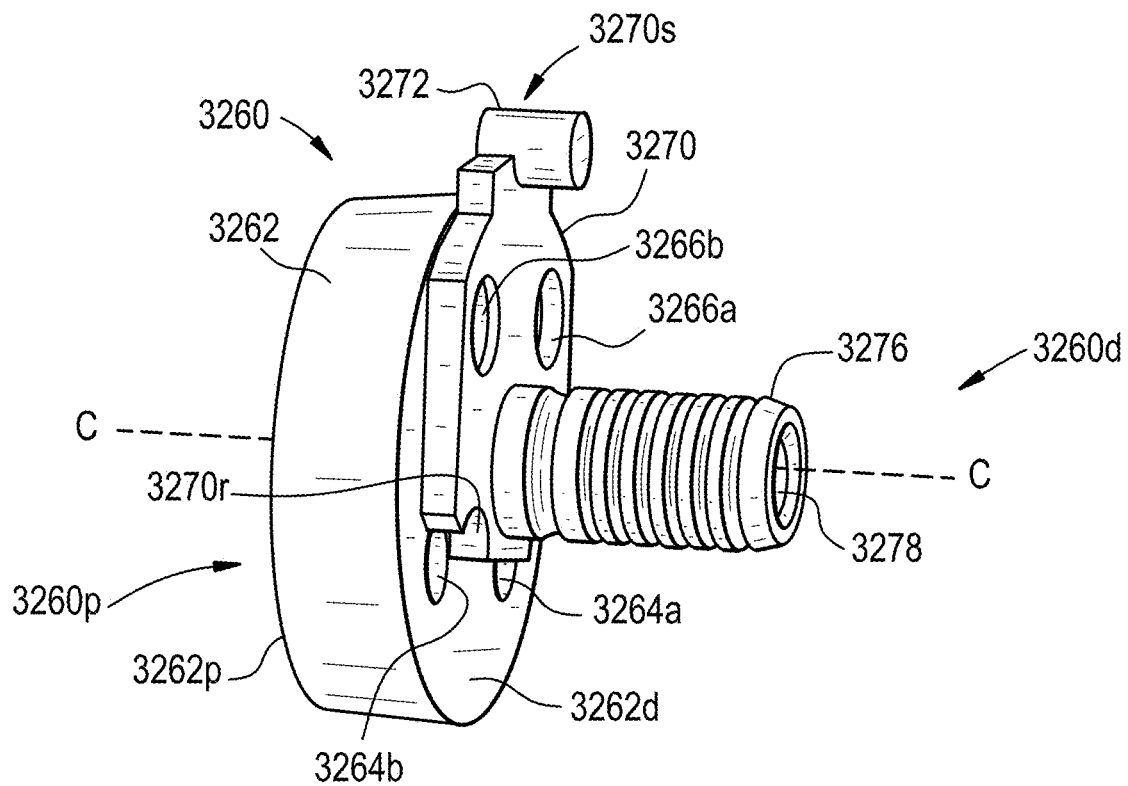
FIG. 27 is a rear perspective view of a metaglene included in the reverse shoulder implant of FIG. 25A.
Figure 28A:
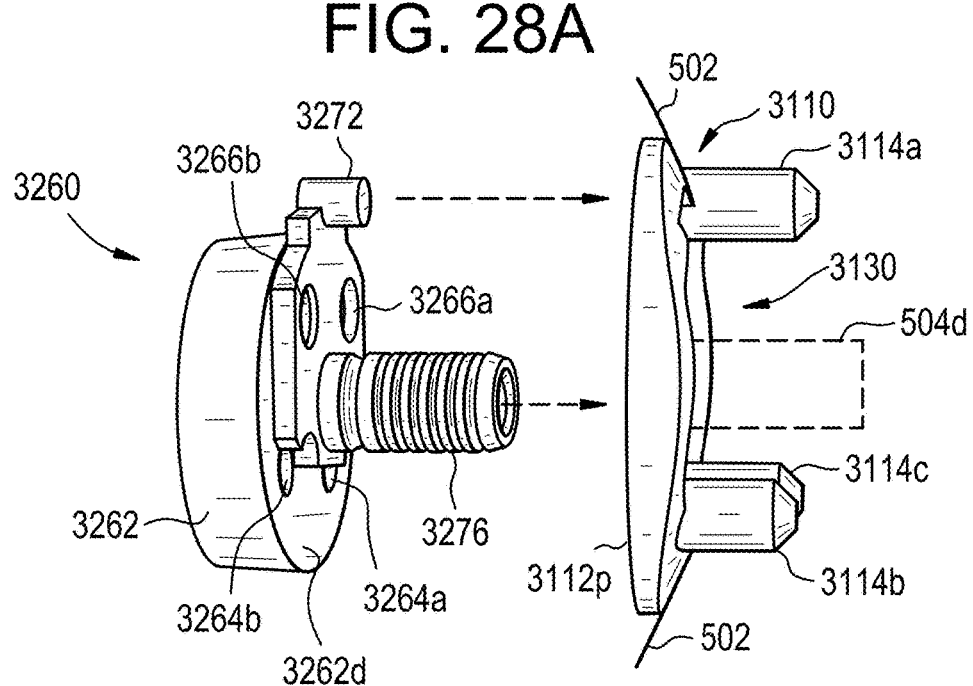
FIGS. 28A, 28B, and 28C are schematic illustrations of one exemplary embodiment of a method of deploying a reverse shoulder joint implant into a patient, like the reverse shoulder joint implant of FIG. 25A.
Figure 28B:
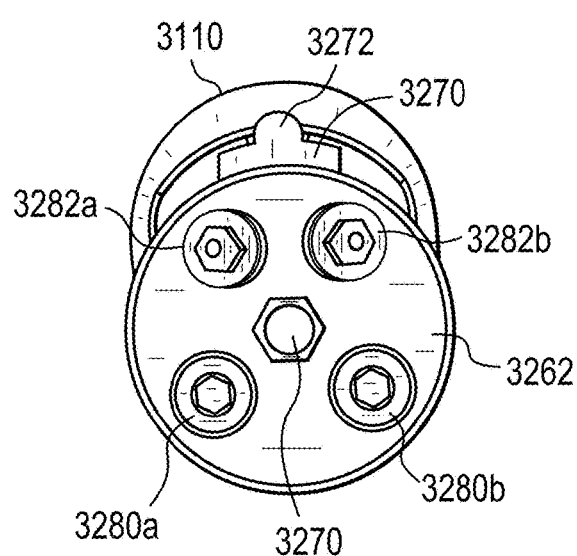
Figure 28C:
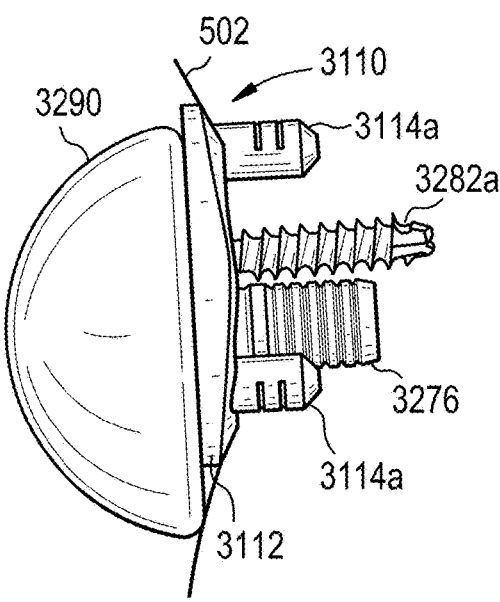

As described in more detail with respect to FIGS. 28A-28C, the bores 3116 of the anchoring pegs 3114 can be configured to attach the reverse glenoid component 3250 to the frame 3110. As indicated above, in some embodiments, the reverse glenoid component 3250 can include a baseplate 3260 and a hemispherical-shaped prosthetic head 3290 coupled to the baseplate. A person skilled in the art, in view of the present disclosure, will understand the reverse glenoid component 3250 to be a prosthetic component as provided for herein, with the baseplate 3260 being part of, or coupled to, a distal-facing surface of the prosthetic component, and the hemispherical-shaped prosthetic head 3290 being part of, or coupled to, a proximal-bearing surface of the prosthetic component. As shown in FIG. 27, the baseplate 3260, sometimes referred to herein as a "metaglene," can include a proximal portion 3260p and a distal portion 3260d.

In some embodiments, the proximal portion 3260p of the metaglene 3260 can include a generally disc-shaped platform 3262 having a proximal surface 3262p and a distal surface 3262d. In some embodiments, one or more through holes can be defined to extend through the proximal and distal surfaces 3262p and 3262d of the metaglene platform 3262 to receive locking screws (not shown) for attaching the metaglene to the frame. For example, in the illustrated embodiment, a pair of through holes 3264a and 3264b (collectively 3264) are defined in the metaglene platform 3262 and can be configured to align with the threaded bores 3116b and 3116c defined in the anchoring pegs 3114b and 3114c when the metaglene 3260 is mounted on the frame 3110. Although two through holes and are shown in the figures, more or less than two through holes can be defined in the metaglene platform 3262 for attaching the metaglene to the frame (e.g., 1, 3, 4, 5, 6 or more through holes).

In some embodiments, the distal portion 3260d of the metaglene 3260 can include a plate-shaped flange 3270 and an unthreaded peg 3272 disposed at a superior end 3270s of the flange. The peg 3272 can be configured to be inserted into the unthreaded bore 3116a of the anchoring peg 3114a at the superior end 3112s of the frame 3110. In some embodiments, the flange 3270 can have a cross-sectional profile configured for insertion into the aperture 3130 of the frame 3110. For example, the cross-sectional profile of the flange 3270 can be configured to generally form a negative of the cross-sectional profile of the frame aperture 3130. The flange 3270 can also define recesses (or cut-away portions) 3270r configured to circumscribe (or at least partially circumscribe) the anchoring pegs 3114b and 3114c of the frame 3110 such that the pegs can be prevented from interfering during attachment of the metaglene 3260 to the frame. Additionally, as shown in the illustrated embodiment, through holes 3266a and 3266b (collectively 3266) can be defined to extend through the metaglene platform 3262 and the flange 3270. Thus, in some embodiments, the through holes 3266 can be used to allow bone screws or the like to be driven, or otherwise inserted, distally through the metaglene 3260, into bone.

In some embodiments, the distal portion 3260d of metaglene 3260 can include a cylindrical-shaped post 3276. As shown in the illustrated embodiment, the post 3276 can be configured to project substantially normal to the flange 3270 of the metaglene 3260. The post 3276 can be inserted into a hole or void formed in bone, e.g., glenoid bone of a patient's scapula. In some embodiments, a through bore 3278 can be defined to extend through the metaglene 3260 along a central longitudinal axis C-C that extends through the post 3276. In some embodiments, the central bore 3278 can be configured to receive a bone screw or other anchor (not shown) for securing the implant to bone. In some embodiments, the central bore 3278 of the metaglene 3260 can be configured to receive a coupling element of the prosthetic head 3290 (not visible).

FIGS. 28A-28C are schematic illustrations of an exemplary embodiment of a method of deploying the reverse shoulder joint implant 3200 in a patient's scapula. In the illustrated embodiment, the reverse shoulder joint implant 3200 can be deployed as part of anatomic-to-reverse conversion of a total shoulder joint arthroplasty in which the anatomic glenoid component of a previously deployed anatomic shoulder joint implant is removed and replaced with the reverse glenoid component 3250. Although the illustrated embodiment describes an anatomic-to-reverse conversion, a person skilled in the art will recognize that the reverse shoulder implant 3200 provided for herein can be deployed without having to previously deploy the anatomic implant.

Referring to FIG. 28A, the frame 3110 is shown anchored to glenoid bone 502 and exposing a concave-shaped portion of the glenoid bone, including a drilled hole 504d. In the illustrated embodiment, the frame 3110 is anchored to bone by three anchoring pegs 3114a, 3114b, and 3114c. In the illustrated anatomic-to-reverse conversion, the anchored frame 3110 can be previously deployed as part of an anatomic total shoulder arthroplasty. An anatomic glenoid component (e.g., 2150 (not shown)) of a previously deployed anatomic glenoid implant can be removed in a prior processing step.

To attach the metaglene 3260 to the frame 3110, the distal portion 3260d of the metaglene 3260 can be distally inserted through the frame aperture 3130 such that the post 3276 is inserted into the previously drilled hole 504d. The metaglene 3260 can continue to be inserted distally until the distal surface 3262d of the metaglene platform 3262 bears against the proximal surface 3112p of the frame 3110. The metaglene 3260 can be manipulated such that the anti-rotation peg 3272 that projects distally from the flange 3270 is inserted into the unthreaded bore 3116a of the anchor peg 3114a. As the metaglene 3260 is inserted into the frame aperture 2130', the bespoke shape of the distal flange 3270 can serve as a key for aligning the through holes 3264 of the metaglene platform 3262 with the threaded bores 3116b and 3116c of the anchoring pegs 3114b and 3114c.

Referring to FIG. 28B, in some embodiments, to secure the metaglene 3260 to the frame 3110, locking screws 3280a and 3280b (collectively 3280) can be driven, or otherwise inserted, distally into the through holes 3264 (not visible) of the metaglene 3260 and into the threaded bores 3116b and 3116c (not visible) of the respective anchoring pegs 3114b and 3114c. Optionally, peripheral bone screws 3282a and 3282b (collectively 3282) can be driven, or otherwise inserted, distally through the respective through holes 3266 of the metaglene 3260 into bone.

Referring to FIG. 28C, the prosthetic head 3290, sometimes referred to herein as a "glenosphere," can be attached to the metaglene 3260. In the illustrated embodiment, the glenosphere 3290 can have a substantially hemispherical-shaped body 3292. Except as described below or as will be readily appreciated by a person skilled in the art, the glenosphere 3290 can be the same, or substantially the same, as the glenosphere 2290 described above. Thus, a detailed description of the structure and function of the glenosphere 3290 is omitted here for the sake of brevity.

For example, as described above with respect to FIGS. 24A-24D, the glenosphere 3290 can be attached to the metaglene 3260 by forming form a taper lock when the metaglene platform 3262 is received within an open-ended cavity (not visible) of the glenosphere body 3292. Alternatively, or additionally, a coupling element (not visible) of the glenosphere 3290 can be configured to lock within the central through bore 3278 of the metaglene 3260. For example, in some embodiments the glenosphere 3290 can be manipulated to screw or press-fit the coupling element into the through bore 3270 of the metaglene 3260. Persons skilled in the art will recognize the glenosphere and the metaglene can be attached together using other techniques and/or mechanisms for securing one component with respect to another.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein. All publications and references cited herein are expressly incorporated herein by reference in their entirety.

The invention claimed is:

1. A method of inserting a prosthetic implant into a patient, comprising:
    anchoring a frame of the implant to a glenoid bone, the frame defining an aperture to the glenoid bone; and
    coupling a prosthetic component of the implant, the prosthetic component including a distal bearing surface and one or more posts projecting outward from the distal bearing surface, to the frame such that at least a portion of the distal bearing surface of the prosthetic component extends through the aperture of the frame to be in direct contact with the glenoid bone,
    wherein the distal bearing surface does not extend along the one or more posts.

2. The method of claim 1, further comprising:
    removing the prosthetic component from the frame; and
    coupling a different prosthetic component to the frame while the frame remains anchored to the glenoid bone.

3. The method of claim 1, wherein coupling a prosthetic component to the frame comprises pressing the prosthetic component into the aperture of the frame such that the prosthetic component snaps onto one or more snap-fit connector interfaces of the frame.

4. The method of claim 1, wherein the prosthetic component is one of an anatomic glenoid component and a reverse glenoid component.

5. A method of inserting a prosthetic implant into a patient, comprising:
    anchoring a frame of the implant to a glenoid bone, the implant including the frame and a prosthetic component, the frame having an inner perimeter that defines an aperture for receiving a distal bearing surface of the prosthetic component, and the prosthetic component having an outer perimeter that defines the distal bearing surface of the prosthetic component; and
    coupling the prosthetic component to the frame such that a majority of the outer perimeter of the prosthetic component is in direct contact with the inner perimeter of the frame and the distal bearing surface of the prosthetic component is in direct contact with the glenoid bone through the aperture of the frame.

6. The method of claim 5, wherein the distal bearing surface of the prosthetic component defined by the outer perimeter of the prosthetic component forms a negative of a cross-sectional profile of the aperture defined by the inner perimeter of the frame.

7. The method of claim 5 further comprising:
    forming a plurality of holes in the glenoid bone,
    wherein anchoring the frame of the implant to the glenoid bone further comprises disposing a plurality of anchor pockets extending from the frame into the plurality of holes formed in the glenoid bone,
    wherein the plurality of anchor pockets is each configured to receive a bone anchor that helps anchor the implant to the glenoid bone.

8. The method of claim 5, wherein coupling the prosthetic component to the frame comprises pressing the prosthetic component into the aperture of the frame such that the prosthetic component snaps onto one or more snap-fit connector interfaces of the frame.

9. The method of claim 5, wherein the distal bearing surface of the prosthetic component comprises a substantially convex-shape configured to fill the aperture defined by the inner perimeter of the frame and further configured to fit into the glenoid bone.

* * * * *